(12) United States Patent
Marrouche et al.

(10) Patent No.: US 10,726,545 B2
(45) Date of Patent: Jul. 28, 2020

(54) SYSTEMS AND METHODS FOR ADMINISTERING TREATMENT OF ATRIAL FIBRILLATION

(71) Applicant: UNIVERSITY OF UTAH RESEARCH FOUNDATION, Salt Lake City, UT (US)

(72) Inventors: Nassir F. Marrouche, Salt Lake City, UT (US); Rob MacLeod, Salt Lake City, UT (US); Evgueni Kholmovski, Salt Lake City, UT (US); Christopher McGann, Salt Lake City, UT (US); Joshua Blauer, Salt Lake City, UT (US); Troy Badger, Salt Lake City, UT (US); Robert Sillman Oakes, Salt Lake City, UT (US); Nathan Burgon, Salt Lake City, UT (US); Marcos Daccarett, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 364 days.

(21) Appl. No.: 15/876,944

(22) Filed: Jan. 22, 2018

(65) Prior Publication Data

US 2018/0240234 A1 Aug. 23, 2018

Related U.S. Application Data

(63) Continuation of application No. 12/784,487, filed on May 20, 2010, now abandoned, and a continuation-in-part of application No. 12/344,164, filed on Dec. 24, 2008, now abandoned, and a continuation-in-part of application No. 12/344,169, filed on Dec. 24, 2008, now abandoned.

(51) Int. Cl.
 *G06T 7/12* (2017.01)
 *G06T 7/00* (2017.01)
 (Continued)

(52) U.S. Cl.
 CPC ............ *G06T 7/0012* (2013.01); *A61B 5/055* (2013.01); *A61B 5/7207* (2013.01);
 (Continued)

(58) Field of Classification Search
 CPC ..... A61B 5/055; A61B 5/7275; A61B 5/7207; A61B 6/037; A61B 5/7285; A61B 6/03;
 (Continued)

(56) References Cited

U.S. PATENT DOCUMENTS 5,687,737 A 11/1997 Branham et al.
5,776,063 A 7/1998 Dittrich et al.
(Continued)

FOREIGN PATENT DOCUMENTS

JP 2001-149340 6/2001
JP 2005-185732 7/2005
(Continued)

OTHER PUBLICATIONS

"Moderate Poster MP01-1 ED—Fogel Richard", Heart Rhythm, Elsevier, US, vol. 7, No. 5, May 1, 2010 (May 1, 2010), pp. S446-S458.
(Continued)

*Primary Examiner* — Sanjay Cattungal
(74) *Attorney, Agent, or Firm* — Michael Best & Friedrich LLP

(57) ABSTRACT

Methods and systems are described for treatment of atrial fibrillation. Certain embodiments provide methods of assessing a risk of thromboembolic stroke in a patient. The method comprises acquiring image data and determining an indicator of a degree of fibrosis of a patient's left atrium (LA) based on the image data. A treatment modality is then determined and administered to the patient based on the analysis of the image data.

34 Claims, 22 Drawing Sheets

(51) Int. Cl.
| | |
|---|---|
| A61B 5/055 | (2006.01) |
| A61B 5/00 | (2006.01) |
| A61B 6/03 | (2006.01) |
| A61B 6/00 | (2006.01) |
| G16H 50/30 | (2018.01) |
| G16H 50/20 | (2018.01) |
| G06F 19/00 | (2018.01) |

(52) U.S. Cl.
CPC .......... *A61B 5/7275* (2013.01); *A61B 5/7285* (2013.01); *A61B 6/03* (2013.01); *A61B 6/037* (2013.01); *A61B 6/481* (2013.01); *A61B 6/486* (2013.01); *G06F 19/321* (2013.01); *G06T 2207/10088* (2013.01); *G06T 2207/20108* (2013.01); *G06T 2207/30048* (2013.01); *G16H 50/20* (2018.01); *G16H 50/30* (2018.01)

(58) Field of Classification Search
CPC ....... A61B 6/481; A61B 6/486; G06F 19/321; G16H 50/30; G16H 50/20; G06T 2207/10088; G06T 2207/20108; G06T 2207/30048
See application file for complete search history.

(56) References Cited

U.S. PATENT DOCUMENTS

| | | |
|---|---|---|
| 6,064,906 A | 5/2000 | Lanberg et al. |
| 9,713,436 B2 | 7/2017 | Marrouche et al. |
| 2002/0049384 A1 | 4/2002 | Davidson et al. |
| 2002/0072490 A1 | 6/2002 | Kapeller-Libermann et al. |
| 2003/0042905 A1 | 3/2003 | Miyazaki et al. |
| 2003/0176782 A1 | 9/2003 | Graessner |
| 2004/0167510 A1 | 8/2004 | Feld et al. |
| 2005/0242973 A1 | 11/2005 | Liebl et al. |
| 2005/0245812 A1 | 11/2005 | Kim et al. |
| 2007/0236491 A1 | 10/2007 | Hundley |
| 2008/0031506 A1 | 2/2008 | Agatheeswaran |
| 2008/0214931 A1 | 9/2008 | Dickfeld |
| 2008/0214945 A1 | 9/2008 | Koertge et al. |
| 2008/0242973 A1 | 10/2008 | Warmuth |
| 2009/0182287 A1 | 7/2009 | Kassab |
| 2010/0160765 A1 | 6/2010 | Marrouche |
| 2010/0160768 A1 | 6/2010 | Marrouche |
| 2010/0292561 A1 | 11/2010 | Greiser |
| 2010/0298694 A1 | 11/2010 | Marrouche et al. |
| 2011/0009861 A1 | 1/2011 | Mukherjee et al. |
| 2014/0378822 A1 | 12/2014 | Marrouche et al. |
| 2017/0332940 A1 | 11/2017 | Marrouche et al. |

FOREIGN PATENT DOCUMENTS

| | | |
|---|---|---|
| WO | WO 2010/075450 | 7/2010 |
| WO | WO 2010/075468 | 7/2010 |
| WO | WO 2011/146779 | 11/2011 |

OTHER PUBLICATIONS

"Sixteenth Meeting of the European Neurological Society May 27-31, 2006, Lausanne, Switzerland; Symposia and Free Communications", Journal of Neurology, Steinkopff-Verlag, DA, vol. 253, No. 2, May 1, 2006, pp. iii-ii170.

Aime-Sempe, C. et al., "Correlation between Left Atrial Structural Remodeling with Persistence and Recurrence in Patients with Atrial Fibrillation" AB30-2 (May 14, 2008) <http://www.abstracts2view.com/hrs/view.php?nu+HRS08L_5375>.

Aime-Sempe, C. et al., "Myocardial cell death in fibrillating and dilated human right atria," J. Am Coll Cardiol, 1999, 34:1577-86.

Akoum NW, Daccarett M, McGann CJ, Segerson N, Vergara G, Kuppahally S, et al. "Atrial fibrosis helps select the appropriate patient and strategy in catheter ablation of atrial fibrillation: A DE-MRI guided approach," J Cardiovasc Electrophys 2011;22:16-22.

Akoum, N. et al., "Correlation between Left Atrial Structural Remodeling with Persistence and Recurrence in Patients with Atrial Fibrillation" AB30-2 (May 14, 2008) <http://www.abstracts2view.com/hrs/view.php?nu+HRS08L_5375>.

Allessie M, Ausma J, Schotten U. Electrical, contractile and structural remodeling during atrial fibrillation. Cardiovasc Res 2002;54:230-246.

Anne et al., "Matrix metalloproteinases and atrial remodeling in patients with mitral valve disease and atrial fibrillation" Cardiovascular Research, 2005, 655-666, vol. 67.

Aronow, W. S. et al., "Risk factors for new thromboembolic stroke inpatients > or = 62 years of age with chronic atrial fibrillation" Am J Cardiol 1998, 82:119-21.

Aronow, W. S. et al., "Risk factors for thromboembolic stroke in elderly patients with chronic atrial fibrillation" Am J Cardiol 1989, 63:366-7.

Atrial Fibrillation Investigators. Risk factors for stroke and efficacy of antithrombotic therapy in atrial fibrillation. Arch Intern Med 1994, 154:1449-57.

Badger TJ, Daccarett M, Akoum NW, Adjei-Poku YA, Burgon NS, Haslam TS, et al. Evaluation of left atrial lesions after initial and repeat atrial fibrillation ablation: Lessons learned from delayed-enhancement MRI in repeat ablation procedures. Circulation: Arrhythm and Electrophysiol 2010;3:249-259.

Badger, T. J. et al., "Catheter Ablation of Atrial Fibrillation Abstract 2753: The Relationship Between Pulmonary Vein Antrum Scarring Following Atrial Fibrillation Ablation and Procedural Success: Does Pulmonary vein Isolation Matter?" Circulation 2008, 118: S_771.

Badger, T. J. et al., "Temporal left atrial lesion formation after ablation of atrial fibrillation" Heart Rhythm 2009, 6:161-8.

Berruezo et al., "Pre-Procedural Predicators of Atrial Fibrillation Recurrence After Circumferential Pulmonary vein Ablation" European Heart Journal, 2007, vol. 28, pp. 836-841.

Cabin, H. S. et al., "Risk for systemic embolization of atrial fibrillation without mitral stenosis", Am J Cardiol 1990, 65:1112-6.

Calo, L. et al., "Left atrial ablation versus biatrial ablation for persistent and permanent atrial fibrillation: a prospective randomized study" J Am Coll Cardiol 2006, 47:2504-12.

Caplan, L. R. et al., "Atrial size, atrial fibrillation, and stroke" Ann Neurol 1986, 19:158-61.

Chugh, A. et al., "Prevalence, mechanisms, and clinical significance of macroreentrant atrial tachycardia during and following left atrial ablation for atrial fibrillation", Heart Rhythm 2005, 2:464-71.

Corbalan, R. et al., "Risk factors for systemic embolism in patients with paroxysmal atrial fibrillation", Am Heart J 1992, 124:149-53.

Corradi D, Callegari S, Benussi S, et al. Myocyte changes and their left atrial distribution in patients with chronic atrial fibrillation related to mitral valve disease. Hum Pathol 2005;36:1080-1089.

Daccarett M, Badger TJ, Akoum NW, Burgon NS, Mahnkopf C, Vergara G, et al. Association of left atrial structural remodeling detected by delayed-enhancement MRI and the risk of stroke in patients with atrial fibrillation. J Am Coll Cardiol 2011;57:831-838.

De Cobelli, F. et al., "Delayed gadolinium-enhanced cardiac magnetic resonance in patients with chronic myocarditis presenting with heart failure or recurrent arrhythmias", J Am Coll Cardiol 2006, 47:1649-54.

Dearborn, J. L. et al., "Perception of risk and knowledge of risk factors in women at high risk for stroke", Stroke 2009, 40:1181-6.

Dickfield, T. et al., "Characterization of radiofrequency ablation lessions with gadolinium-enhanced cardiovascular magnetic resonance imaging" J Am Coll Cardiol 2006, 47:370-8.

Echocardiographic Predictors of Stroke in Patients With Atrial Fibrillation. A prospective study of 1,066 Patients from 3 clinical trials, Arch Intern Med 1998, 158:1316-20.

Ezekowitz et al., "Echocardiographic Predictors of Stroke in Patients With Atrial Fibrillation" Arch Intern Med., 1998, 1316-1320, vol. 158.

(56) References Cited

OTHER PUBLICATIONS

Fang et al., "Comparison of Risk Stratification Schemes to Predict Thromboembolism in People With Nonvalvular Atrial Fibrillation" J. of the American College of Cardiology, 2008, 810-815, vol. 51, No. 8.
Fatema, K. et al., "Increased left atrial volume index: potent biomarker for first-ever ischemic stroke" Mayo Clin Proc 2008, 83:1107-15.
Fuster V RL, Cannom DS, Crijns HJ, Curtis AB, Ellenbogen KA, Halperin JL, Le Heuzey JY, Kay GN, Lowe JE, Olsson SB, Prystowsky EN, Tamargo JL, Wann S, Smith SC Jr, Jacobs AK, Adams CD, Anderson JL, Antman EM, Halperin JL, Hunt SA, Nishimura R, Ornato JP, Page RL, Riegel B, Priori SG, Blanc JJ, Budaj A, Camm AJ, Dean V, Deckers JW, Despres C, Dickstein K, Lekakis J, McGregor K, Metra M, Morais J, Osterspey A, Tamargo JL, Zamorano JL; American College of Cardiology; American Heart Association Task Force; European Society of Cardiology Committee for Practice Guidelines; European Heart Rhythm Association; Heart Rhythm Society. ACC/AHA/ESC 2006 Guidelines for the Management of Patients with Atrial Fibrillation: a report of the American College of Cardiology/American Heart Association Task Force on Practice Guidelines and the European Society of Cardiology Committee for Practice Guidelines (Writing Committee to Revise the 2001 Guidelines for the Management of Patients With Atrial Fibrillation): developed in collaboration with the European Heart Rhythm Association and the Heart Rhythm Society. Circulation 2007;114:98.
Gage et al., "Selecting Patients With Atrial Fibrillation for Anticoagulation: Stroke Risk Stratification in Patients Taking Aspirin" Circulation, 2004, 2287-2292, vol. 110.
Gage et al., "Validation of Clinical Classification Schemes for Predicting Stroke: Results From the National Registry of Atrial Fibrillation" J American Medical Association, 2001, 2864-2870, vol. 285, No. 22.
Gage, B. F. et al., "Cost-effectiveness of preference-based antithrombotic therapy for patients with nonvalvular atrial fibrillation" Stroke 1998, 29:1083-91.
Gaita, F. et al., "Linear cryoablation of the left atrium versus pulmonary vein cryoisolation in patients with permanent atrial fibrillation and valvular heart disease: correlation of electroanatomic mapping and long-term clinical results" Circulation 2005, 111:136-42.
Gerstenfeld, E. P et al., "Utility of exit block for identifying electrical isolation of the pulmonary veins", J Cardiovasc Electrophysiol 2002, 13:971-9.
Goldman, M. E. et al., "Transesophageal echocardiographic correlates of a clinical risk of thromboembolism in nonvascular atrial fibrillation. Reduced flow velocity in the left atrial appendage", J Am Soc Echo 1999, 12:1080-7.
Haissaguerre, M. et al., "Catheter ablation of long-lasting persistent atrial fibrillation: clinical outcome and mechanisms of subsequent arrythmias" J Cardiovasc Electrophysiol 2005, 16:1138-47.
Haissaguerre, M. et al., "Catheter ablation of long-lasting persistent atrial fibrillation: clinical structures for termination" J Cardiovasc Electrophysiol 2005, 16:1125-37.
Haissaguerre, M. et al., "Spontaneous initiation of atrial fibrillation by ectopic beats originating in the pulmonary veins", N Engl J Med 1998, 339:659-66.
Halperin et al., "Damage Assessment after Ablation", Journal of the American College of Cardiology, 2008, pp. 1272-1273, vol. 52, No. 15, Elsevier Inc.
Hart, "Independent predictors of stroke in patients with atrial fibrillation: A systematic review" Neurology, 2007, 546-554, vol. 69.
Hart, R. G. et al., "Antithrombotic therapy to prevent stroke in patients with atrial fibrillation: a meta-analysis", Ann Intern Med 1999, 131:492-501.
Hsu, L. Y. et al., "Quantitative myocardial infarction on delayed enhancement MRI. Part I: animal validation of an automated feature analysis and combined thresholding infarct sizing algorithm", J Magn Reson Imaging 2006, 23:298-308.
Hsu, L. Y. et al., "Quantitative myocardial infarction on delayed enhancement MRI. Part II: clinical application of an automated feature analysis and combined thresholding infarct sizing algorithm", J Magn Reson Imaging 2006, 23:309-14.
Karch, M. R. et al., "Freedom from atrial tachyarrhythmias after catheter ablation of atrial fibrillation: a randomized comparison between 2 current ablation strategies", Circulation 2005, 111:2875-80.
Kholmovski et al., "Calculation of Optimal TI Value t'or 3D LGE-MRI of the Let't Atrium," Proc. Intl. Soc. Mag. Reson. Med. 21 (2013) p. 4562.
Kim, R. J. et al., "Relationship of MRI delayed contrast enhancement to irreversible injury, infarct age, and contractile function", Circulation 1999, 100:1992-2002.
Kim, R. J., "The use of contrast-enhanced magnetic resonance imaging to identify reversible myocardial dysfunction" N Engl J Med 2000, 343:1445-53.
Kistler, P. M. et al., "Electrophysiologic and anatomic characterization of sites resistant to electrical isolation during circumferential pulmonary vein ablation for atrial fibrillation: a prospective study", J Cardiovasc Electrophysiol 2007, 18:1282-8.
Kistler, P. M. et al., "The impact of CT image integration into an electroanatomic mapping system on clinical outcomes of catheter ablation of atrial fibrillation", J cardiovasc Electropysiol 2006, 17:1093-101.
Klein, C. et al., "Assessment of myocardial viability with contrast-enhanced magnetic resonance imaging: comparison with positron emission tomography", Circulation 2002, 105:162-7.
Knuesel, P. R. et al., "Characterization of dysfunctional myocardium by positron emission tomograpgy and magnetic resonance: relation to functional outcome after revascularization", Circulation 2003, 108:1095-100.
Laissy, J. P. et al., "Differentiating acute myocardial infarction from myocarditis: diagnostic value of early- and delayed-perfusion cardiac MR imaging", Radiology 2005, 237:75-82.
Lardo, A. C. et al., "Visualization and temporal/spatial characterization of cardiac radiofrequency ablation lesions using magnetic resonance imaging", Circulation 2000, 102:698-705.
Levitt et al., "NMR Population Inversion Using a Composite Pulse," Journal of Magnetic Resonance 33, 473-476 (1979).
Lewsey, J. D. et al., "Sex differences in incidence, mortality, and survival in individuals with stroke in Scotland, 1986 to 2005", Stroke 2009, 40:1038-43.
Li D, Fareh S, Leung T, Nattel S. Promotion of atrial fibrillation by heart failure in dogs: Atrial remodeling of a different sort. Circulation 1999;100:87-95.
Li, D. et al., "Effects of angiotensin-converting enzyme inhibition on the development of the atrial fibrillation substrate in dogs with ventricular tachypacing-induced congestive heart failure", Circulation 2001, 104:2608-14.
Lip et al., "Additive Role of Plasma von Willebrand Factor Levels to Clinical Factors for Risk Stratification of Patients With Atrial Fibrillation" Stroke, 2006, 2294-2300 and 2444, vol. 37.
Look DC, Locker DR. Time saving in measurement of NMR and EPR relaxation times. Rev Sci Instrum 1970;41:250-251.
Mahrholdt, H. et al., "Cardiovascular magnetic resonance assessment of human myocarditis: a comparison to histology and molecular pathology", Circulation 2004, 109:1250-8.
Marrouche, N. F. et al., "Circular mapping and ablation of the pulmonary vein for treatment of atrial fibrillation: impact of different catheter technologies," J Am Coll Cardiol 2002, 40:464-74.
Marrouche, N. F. et al., "Phase-array intracardiac ecocardiography monotoring during pulmonary vein isolation in patients in patients with atrial fibrillation: impact on outcome and complications", Ciculation 2003, 107:2710-6.
McGann CJ, Kholmovski EG, Oakes RS, Blauer JJE, Daccarett M, Segerson N, et al. New magnetic resonance imaging-based method for defining the extent of left atrial wall injury after the ablation of atrial fibrillation. J Am Coll Cardiol 2008;52:1263-1271.

(56) References Cited

OTHER PUBLICATIONS

Menon, S. C. et al., "Critical factors determining access to acute stroke care", Neurology 1998, 51:427-32.
Nademanee, K. et al., "A new approach for catheter ablation of atrial fibrillation: mapping of the electrophysiologic substrate", J Am Coll Cardiol 2004, 43:2044-53.
Naganawa et al., "Estimation of Gadolinium-induced T1-shortening with Measurement of Simple Signal Intensity Ratio between the Cochlea and Brain Parenchyma on 3D-FLAIR: Correlation with T1 Measurement by TI Scout Sequence," Magn Reson Med Sci, vol. 9, No. 1, pp. 17-22, 2010.
Natale, A. et al., "Prospective randomized comparison of antiarrhythmic therapy versus first-line radiofrequency ablation in patients with atrial flutter", J Am Coll Cardiol 2000, 35:1898-904.
Oakes RS, Badger TJ, Kholmovski EG, et al. Detection and quantification of left atrial structural remodeling with delayed-enhancement magnetic resonance imaging in patients with atrial fibrillation. Circulation. 2009;119:1758-1767.
Oh, S. et al., "Avoiding microbubbles formation during radiofrequency left atrial ablation versus continuous microbubbules formation and standard radiofrequency ablation protocols: comparison of energy profiles and chronic lesion characteristics" J Cardiovasc Electrophysiol 2006, 17:72-7.
Okuyama et al., "Usefulness of Intensity Varation in the Left Atrial Appendage With Contrast Echocardiology to Predict Ischemic Stroke Recurrence in Patients With Atrial Fibrillation", The American Journal of Cardiology, 2008, vol. 101, pp. 1630-1637.
Olshansky et al., "Fibrillation recurrence or Stroke?: Results From the Atrial Fibrillation Are Transthoracic Echocardiographic Parameters Associate With Atrial Follow-Up Investigation of Rhythm Management (AFFIRM) Study", Journal of the American College of Cardiology, 2005, vol. 45, No. 12, pp. 2026-2033.
Oral, H. et al., "Circumferential pulmonary-vein ablation for chronic atrial fibrillation" N Engl J Med 2006, 354:934-41.
Oshinski, J. N. et al., "Quantitative prediction of improvement in cardiac function after revascularization with MR imaging and modeling: initial results", Radiology 2001, 221:515-22.
Ouyang, F. et al., "Electrophysiological findings during ablation of persistent atrial fibrillation with electroanatomic mapping and double Lasso catheter technique", Circulation 2005, 112:3038-48.
Ouyang, F. et al., "Recovered pulmonary vein conduction as a dominant factor for recurrent atrial tachyarrhythmias after complete circular isolation of the pulmonary veins: lessons from double Lasso technique", Circulation 2005, 111:127-35.
Pan et al., "Aging Dilates Atrium and Pulmonary Veins Implications for the Genesis of Atrial Fibrillation" Chest, 2008, 190-196, vol. 133.
Parkash et al., "The Association of Left Atrial Size and Occurrence of Atrial Fibrillation: A Prospective cohort Study From the Canadian Registry of a Atrial Fibrillation", American Heart Journal, 2004, vol. 148, pp. 649-654.
Peters DC, Wylie JV, Hauser TH, Kissinger KV, Botnar RM, Essebag V, et al. Detection of pulmonary vein and left atrial scar after catheter ablation with three-dimensional navigator-gated delayed enhancement MR imaging: Initial experience. Radiology 2007;243:690-695.
Peters, et al., "Recurrence of Atrial Fibrillation Following RF Ablation Correlates with the Extent of Post-procedural Left Atrial Scarring on Delayed-Enhancement CMR", Circulation, 2007, pp. 1-3, American Heart Association, Abstract 3371, <http://circ.ahajournals.org/cgi/content/meeting_abstract/116/16_MettingAbstracts/II_760-d>.
Petersen, P. et al., "Risk factors for thromboembolic complications in chronic atrial fibrillation The Copenhagen AFASAK study", Arch Intern Med 1990, 150:819-21.
Pritchett, A. M. et al., "Left atrial volume as an index of left atrial size: a population-based study", J Am Coll Cardiol 2003, 41:1036-43.
Rochitte, C. E. et al., "The emerging role of MRI in the diagnosis and management of cardiomyopathies", Curr Cardiol Rep 2006, 8:44-52.
Sanders, P. et al., "Electrical remodeling of the atria in congestive heart failure: electrophysiological and electronatomic mapping in humans", Circulation 2003, 108:1461-8.
Sauer, W. H. et al., "Clinical predictors and outcomes associated with accute return of pulmonary vein conduction during pulmonary vein isolation for treatment of atrial fibrillation", Heart Rhythm 2006, 3:1024-8.
Schoonderwoerd BA, Van Gelder IC, Van Veldhuisen DJ, Van den Berg MP, Crijns HJ. Electrical and structural remodeling: Role in the genesis and maintenance of atrial fibrillation Prog Cardiovasc Dis 2005;48:153-168.
Segerson NM, Daccarett M, Badger TJ, Shabaan A, Akoum N, Fish EN et al. Magnetic resonance imaging-confirmed ablative debulking of the left atrial posterior wall and septum for treatment of persistent atrial fibrillation: Rationale and initial experience. J Cardiovasc Electrophysiol 2010;21:126-132.
Seneviratne, B. I. et al., "Nonvalvular atrial fibrillation associated with cardioembolic stroke: the role of hypertensive heart disease", Aust N Z J Med 1990, 20:127-34.
Shin, S. H. et al., "Left Atrial Volume Is a Predictor of Atrial Fibrillation Recurrence After Catheter Ablation", Journal of the American Society of Echocardiography, 2008, vol. 21, issue 6, pp. 697-702.
Sievers, B. et al., "Cardiovascular magnetic resonance of iatrogenic ventricular scarring due to catheter ablation for left ventricular tachycardia", Int J Cardiol 2003, 91:249-50.
Spach, M. et al., "The functional role of structural complexities in the propagation of depolarization in the atrium of the dog. Cardiac conduction disturbances due to discontinuities of effective axial resistivity", Circ Res 1982, 50:175-91.
Stollberger et al., "Transesophageal Echocardiography to Assess Embolic Risk in Patients with Atrial Fibrillation" Annals of Internal Medicine, 1998, 630-638, vol. 128.
Suranyi et al., "Equilibrium signal intensity mapping an MRI method for fast mapping of longitudinal relaxation rates and for image enhancement" Magnetic Resonance Imaging 25 (2007) 641-651.
Tanaka et al., "Spatial Distribution of Fibrosis Governs Fibrillation Wave Dynamic in the Posterior Left Atrium During Heart Failure" Circulation research, 2007, 839-847 and online supplement pp. 1-33, vol. 101.
The SPAF III Writing Committee for the Stroke Prevention in Atrial Fibrillation Investigators. Patients with nonvalvular atrial fibrillation at low risk of stroke during treatment with aspirin: Stroke Prevention in Atrial Fibrillation III study, JAMA 1998, 279:1273-7.
The Stroke Prevention in Atrial Fibrillation Investigators. Predictors of thromboembolism in atrial fibrillation: II. Echocardiographic features of patients at risk Ann Intern Med 1992, 116:6-12.
The Stroke Risk in Atrial Fibrillation Working Group. Independent predictors of stroke in patients with atrial fibrillation: a systematic review, Neurology 2007, 69:546-54.
Verma, A. et al, "Response of atrial fibrillation to pulmonary vein antrum isolation is directly related to resumption and delay of pulmonary vein conduction", Circulation 2005, 112:627-35.
Vijayakumar et al., "Contrast Optimization for LGE imaging of Left Atrium," Proceedings of the International Society for Magnetic Resonance in Medicine, ISMRM, 18th Scientific Meeting and Exhibition, Stockholm, Sweden, May 1-7, 2010.
Wazni, O. M. et al., "Radiofrequency ablation vs antiarrhythmic drugs as first-line treatment of symptomatic atrial fibrillation: a randomized trial" JAMA 2005, 293:2634-40.
Wijffels MC, Kirchhof CJ, Dorland R, Allessie MA. Atrial fibrillation begets atrial fibrillation. A study in awake chronically instrumented goats. Circulation 1995;92:1954-1968.
Willems, S. et al., "Substrate modification combined with pulmonary vein isolation improves outcome of catheter ablation in patients with persistent atrial fibrillation: a prospective randomized comparison" Eur Heart J 2006, 27:2871-8.

(56) References Cited

OTHER PUBLICATIONS

Wolf, P. A. et al., "Atrial fibrillation: a major contributor to stroke in the elderly. The Framingham Study", Arch Intern Med 1987, 147:1561-4.
Wongcharoen, W. et al., "Effects of aging and ouabain on left atrial arrhythmogenicity", J Cardiovasc Electrophysiol 2007, 18:526-31.
Zabalgoitia et al., "Transesophageal echocardiographic correlates of clinical risk of thromboembolism in nonvalvular atrial fibrillation. Stroke Prevention in Atrial Fibrillation III Investigators" J. of the American College of Cardiology, 1998, 1622-1626, vol. 31.
Australian Patent Office Action for Application No. 2012332703 dated Aug. 5, 2016 (3 pages).
European Patent Office Action for Application No. 09835812.0 dated Jan. 31, 2014 (6 pages).
European Patent Office Extended Search Report for Application No. 09835801.3 dated Jul. 2, 2014 (13 pages).
European Patent Office Extended Search Report for Application No. 12846149.8 dated May 29, 2015 (10 pages).
Extended European Patent Office Search Report for Application No. 11784282 dated Sep. 21, 2015 (9 pages).
International Search Report and Written Opinion for Application No. PCT/US2009/069306 dated Jul. 21, 2010 (6 pages).
International Search Report and Written Opinion for Application No. PCT/US2009/069330 dated Jul. 21, 2010 (6 pages).
International Search Report and Written Opinion for Application No. PCT/US2011/037251 dated Aug. 24, 2011 (8 pages).
International Search Report and Written Opinion for Application No. PCT/US2012/062616 dated Feb. 7, 2013 (9 pages).
United States Patent Office Action for U.S. Appl. No. 12/344,164 dated Dec. 5, 2014 (15 pages).
United States Patent Office Action for U.S. Appl. No. 12/344,164 dated Oct. 19, 2015 (17 pages).
United States Patent Office Action for U.S. Appl. No. 12/344,164 dated Sep. 15, 2016 (21 pages).
United States Patent Office Action for U.S. Appl. No. 12/344,164 dated Jun. 1, 2017 (15 pages).
United States Patent Office Action for U.S. Appl. No. 12/344,169 dated Feb. 20, 2015 (15 pages).
United States Patent Office Action for U.S. Appl. No. 12/344,169 dated Oct. 19, 2015 (18 pages).
United States Patent Office Action for U.S. Appl. No. 12/344,169 dated Sep. 8, 2016 (27 pages).
United States Patent Office Action for U.S. Appl. No. 12/344,169 dated May 16, 2017 (15 pages).
United States Patent Office Action for U.S. Appl. No. 12/784,487 dated Jan. 13, 2015 (18 pages).
United States Patent Office Action for U.S. Appl. No. 12/784,487 dated Oct. 23, 2015 (27 pages).
United States Patent Office Action for U.S. Appl. No. 12/784,487 dated Sep. 20, 2016 (25 pages).
United States Patent Office Action for U.S. Appl. No. 12/784,487 dated May 19, 2017 (14 pages).
United States Patent Office Action for U.S. Appl. No. 14/355,201 dated Sep. 2, 2016 (7 pages).
United States Patent Office Notice of Allowance for U.S. Appl. No. 14/355,201 dated Mar. 21, 2017 (8 pages).
United States Patent Office Action for U.S. Appl. No. 15/658,741 dated Nov. 1, 2017 (7 pages).
United States Patent Office Notice of Allowance for U.S. Appl. No. 15/658,741 dated Feb. 27, 2018 (8 pages).

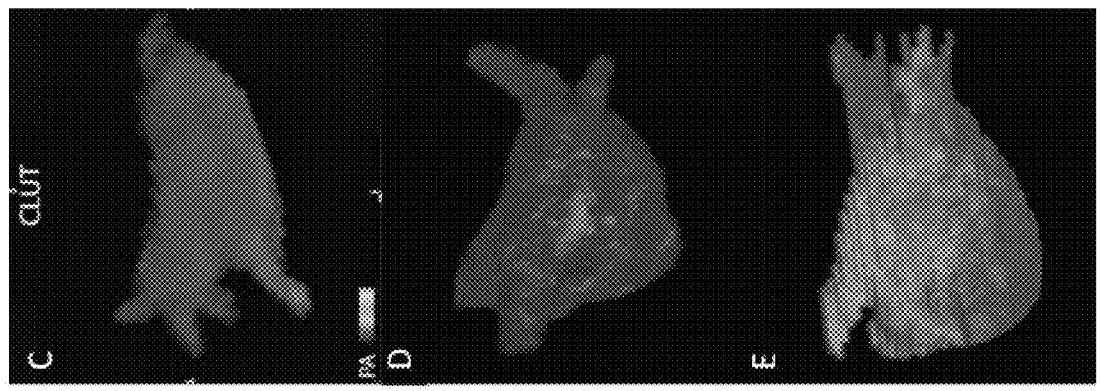
FIG. 21C
FIG. 21D
FIG. 21E
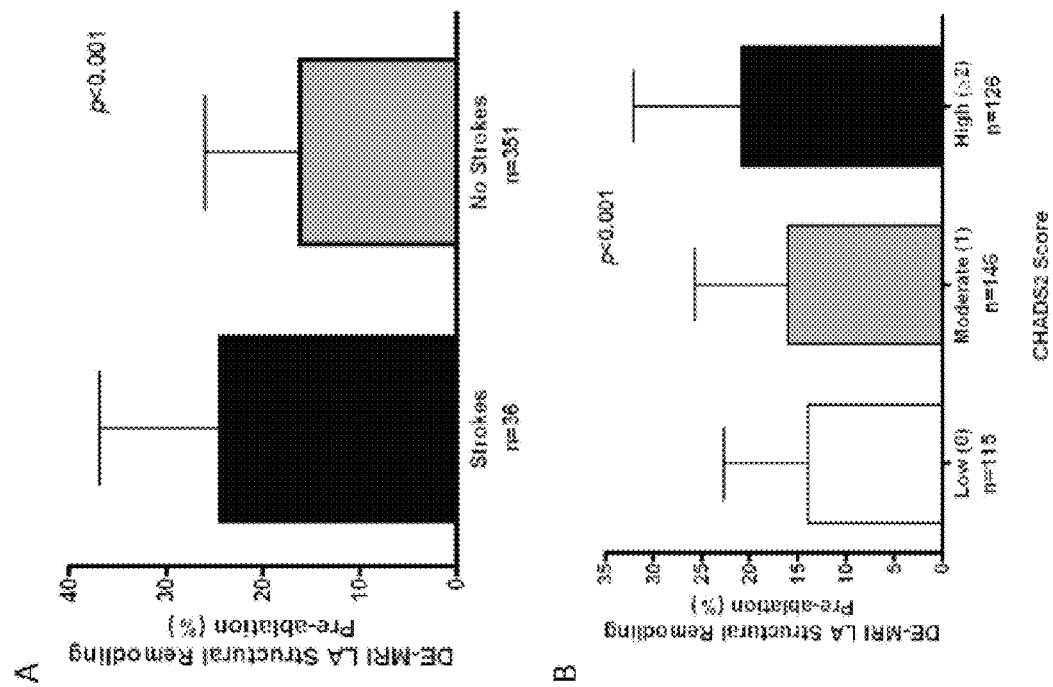
FIG. 21A
FIG. 21B

SYSTEMS AND METHODS FOR ADMINISTERING TREATMENT OF ATRIAL FIBRILLATION

CROSS-REFERENCE TO RELATED APPLICATIONS

This application is a continuation of U.S. patent application Ser. No. 12/784,487, filed on May 20, 2010, entitled "STROKE RISK ASSESSMENT," which is a continuation-in-part of U.S. patent application Ser. No. 12/344,164, filed Dec. 24, 2008, entitled "THERAPEUTIC SUCCESS PREDICTION FOR ATRIAL FIBRILLATION" and is also a continuation-in-part of U.S. application Ser. No. 12/344,169, filed Dec. 24, 2008, entitled "THERAPEUTIC OUTCOME ASSESSMENT FOR ATRIAL FIBRILLATION," the entire contents of all of which are incorporated herein by reference.

FIELD

The present invention generally relates to stroke risk assessment and, in particular, relates to thromboembolic stroke risk assessment for patients with a history of atrial fibrillation.

BACKGROUND

Atrial fibrillation (AF) is a cardiac disorder involving an irregular, and often ineffective, quiver-type beating of the heart's two upper chambers (the atria). In certain forms of AF, blood may not be pumped completely out of the atria, pool along the atrial walls, and eventually clot. If a blood clot in the atria leaves the heart and becomes lodged in a brain artery, stroke can result.

AF may be associated with significant morbidity and mortality, primarily due to the increased risk of ischemic stroke. Patients who suffer from this arrhythmia have about a 3% to 4% absolute risk of stroke per year, but this varies significantly based on individual clinical features. Antithrombotic therapy with the vitamin K antagonist warfarin may be highly effective in stroke prevention and in improving survival. However, it may be associated with life threatening hemorrhage and may require intensive dosage monitoring.

AF affects more than 2.2 million people in the United States, and the prevalence of AF increases with age. Approximately 4% of people over age 60 have experienced an episode of AF. AF can occur in healthy people, but more often is associated with an underlying condition such as coronary heart disease, hypertension, valvular heart disease, and rheumatic heart disease. AF may also develop after cardiac or pulmonary surgery.

Treatments for AF include medications to decrease blood clotting, medications to slow down rapid heart rate, electric shock to restore normal heart rhythm (cardioversion), pulmonary vein antrum isolation (PVAI), and use of pacemakers to regulate heart beat rhythm.

Normally, a mammalian heart beat comprises phases called "diastole," in which the heart relaxes and fills with blood, and "systole," in which the heart contracts and pumps out the blood. An electrical wavefront typically starts in the "sinoatrial" (SA) node of the atrium, spreads over the two atria, and leads to contraction of cardiac muscle. When such an electrical wavefront reaches the "atrioventricular" (AV) node, the wavefront is delayed, which allows the atria to finish contracting, moving blood from the atria to the ventricles.

From the AV node, the electrical wavefront spreads through the His-Purkinje system, which comprises fibers that form a specialized conduction system that quickly propagates the wavefront throughout the ventricles, resulting in ventricular contraction. Contraction of the ventricles pumps blood into the lungs and body. At the end of contracting, the ventricles relax and the process repeats.

An electrocardiogram (ECG) can be used to assess heart rhythm and disturbances therein by measuring electrical activities of the heart that are detectable at surfaces of the body. An ECG typically comprises a repeated pattern of three measured electrical waveform components of a heartbeat: the "P wave," the "Q wave," and the "T wave." The P wave results from atrial depolarization, i.e., the wavefront generated as electrical impulses from the SA node spread throughout the atrial musculature. The Q wave occurs at the beginning of a "QRS complex," but may not always be present. The T wave involves electrical recovery of the ventricles.

The P wave precedes the QRS complex, which occurs as a result of ventricular depolarization. The QRS complex, a large waveform, typically comprises three waves, the "Q wave," the "R wave," and the "S wave," but not every QRS complex contains a Q wave, an R wave, and an S wave. By convention, any combination of these waves can be referred to as a QRS complex. The Q wave represents depolarization of the interventricular septum. The R wave is typically the first positive deflection, and the S wave is the negative deflection that follows the R wave. The time interval between two consecutive beats, the so-called "beat interval," is often measured from the R-wave of one beat to the R-wave of the following beat, and the time between two consecutive R waves is called the RR interval. A "PR interval" comprises the time it takes an electrical impulse to travel from the atria through the AV node, bundle of His, and bundle branches to the Purkinje's fibers; and the PR interval extends from the beginning of the P wave to the beginning of the QRS complex.

The QRS complex is usually the dominant feature of an ECG. The P wave is much smaller than the QRS complex because the atria generate less electrical activity than the larger ventricles. Other components of an ECG include the "Q-T Interval," which represents the time necessary for ventricular depolarization and repolarization, and extends from the beginning of the QRS complex to the end of a T wave. By analyzing patterns of an ECG, insights into the condition of the heart can be obtained.

In an ECG from a heart with normal rhythm, large QRS complexes are separated by a fairly flat signal, except for a small upright bump (the P wave) about 120-200 ms before the QRS complex. A P wave is conducted when atrial electrical activity conducts through the AV node, causing electrical activation of the ventricles and the QRS complex. At most one P wave in an RR interval is conducted, and any other P waves in the same RR interval are non-conducted. A P wave is non-conducted when it fails to lead to a QRS complex. Non-conducted P waves can result from a premature P wave, a condition called AV block, and other reasons. P waves non-conducted as a result of AV block are said to be blocked P waves.

In atrial flutter, the atrial rhythm can increase to approximately 250-350 beats per minute. Increased atrial rhythms are sometimes detected as continuous waves in an ECG, with several waves appearing in a continuous, connected pattern in each RR interval: a pattern substantially different from the normal pattern of a single P wave in each RR interval. Such waves of continuous, cyclic atrial activity are called flutter waves or F-waves, and may form a sawtooth pattern in an ECG. During atrial flutter, the ventricular response can become locked into a regular pattern with the atrial activity, so that, for instance, every third flutter wave results in a QRS complex while the other flutter waves are non-conducted. In other cases, conduction of the flutter waves can be more random, resulting in an irregular ventricular rhythm.

Rapid atrial rhythm rates, generally over 350-400 beats per minute, are called AF. Such atrial activity can be visible in the RR interval as continuous, cyclic activity referred to as "f waves," or coarse AF. Typically, the f waves are cyclic, but not as organized or consistent in shape as the F waves of atrial flutter. When viewed in two ECG channels, the cyclic activity of f waves may be seen to alternate back and forth between channels in what appears to be modulated electrical activity. At other times, AF may be present with no obvious cyclic activity visible in an ECG, but with low amplitude disorganized "noise" in the baseline. In other cases, there may be total absence of atrial activity, suggesting that the AF has become disorganized.

SUMMARY

Certain embodiments provide a method of assessing an outcome of an ablative atrial fibrillation (AF) treatment modality administered to a patient, the method comprising: determining, from left atrium (LA) tissue image data of a subject patient that has undergone a first ablative AF treatment with the modality, at least one of: (i) a level of a parameter that is positively proportional or negatively proportional to an amount of ablated tissue in a wall of the LA of the subject patient; and (ii) a spatial distribution, in the LA wall, of a variable indicative of ablated LA tissue; and outputting, to an output device, a machine-readable indicator of at least one of: (i) a comparison between the determined level and a threshold level of the parameter; wherein the threshold level is derived from LA tissue image data of at least one other patient who did not experience an AF recurrence for a significant period of time after treatment with the AF treatment modality; wherein, when the level of the parameter is positively proportional to the amount of ablated tissue, levels of the parameter equal to or less than the first threshold level are indicative of a significant risk of AF recurrence; wherein, when the level of the parameter is negatively proportional to the amount of ablated tissue, levels of the parameter equal to greater than the first threshold level are indicative of a significant risk of AF recurrence; and (ii) a map of the spatial distribution, wherein an indication, from the map, of a lack of electrical isolation of one or more pulmonary veins of the subject patient indicates a significant risk of AF recurrence.

In certain embodiments, the output device comprises at least one of a microprocessor, a computer, a storage medium, a server, a paper, a graphical user interface, a computer display, an LCD, an LED, and a television display. In certain embodiments, the subject patient underwent the ablative AF treatment modality less than about six months and more than about one day prior to the time at which the LA data was acquired.

In certain embodiments, the significant period of time comprises at least two months. In certain embodiments, the significant period of time comprises at least three months.

In certain embodiments, a method comprises, based on the indicator, administering a second ablative AF treatment to the subject patient.

In certain embodiments, a method comprises determining, from tissue image data of the subject patient, an amount of esophageal damage in the subject patient after the first ablative AF treatment.

In certain embodiments, the ablation comprises at least one of radiofrequency ablation, thermal ablation, laser ablation, surgical ablation, and cryoablation. In certain embodiments, the ablation comprises pulmonary vein antrum isolation. In certain embodiments, the level of the parameter comprises a proportion of ablated LA wall tissue relative to a total amount of the LA wall tissue.

In certain embodiments, the proportion of ablated LA wall tissue relative to a total amount of LA wall tissue comprises a ratio of (i) an imaged volume of ablated LA wall tissue to (ii) an imaged total volume of LA wall tissue. In certain embodiments, the proportion is between about 1% and about 20%, and wherein the significant risk comprises a risk of AF recurrence of between about 15% and about 80% risk.

In certain embodiments, the AF treatment modality comprises administration of a therapeutic substance. In certain embodiments, the therapeutic substance comprises an anti-arrhythmic medication.

In certain embodiments, a method comprises acquiring the image data by detecting a signal of an agent substantially localized at the ablated LA tissue. In certain embodiments, the agent comprises a magnetic resonance contrast agent, and wherein the detecting comprises performing magnetic resonance imaging. In certain embodiments, the magnetic resonance imaging comprises delayed enhancement magnetic resonance imaging (DE-MRI). In certain embodiments, the agent comprises gadolinium.

In certain embodiments, a method comprises localizing the agent to the ablated LA tissue by exposing the LA tissue to an antibody or antibody component, coupled to the agent, that binds an epitope present in the ablated LA tissue and not present in healthy LA tissue, such that a substantial amount of the agent present at the LA tissue, at the time of image data acquisition, is bound to the ablated LA tissues through antibody-epitope binding. In certain embodiments, the epitope comprises at least one of collagen, fibrinogen, fibrin, and fibronectin. In certain embodiments, the antibody or antibody component comprises at least one of a monoclonal antibody, a polyclonal antibody, a Fab peptide, and a single chain variable region peptide.

In certain embodiments, the agent comprises a radioisotope, and wherein the detecting the signal comprises performing at least one of positron emission tomography (PET), radionuclide scanning, and single photon emission computed tomography (SPECT). In certain embodiments, the agent comprises an isotope of at least one of P, I, Tl, Tc, and H. In certain embodiments, the agent comprises a radiopaque marker, and wherein the detecting comprises performing at least one of radiography and fluoroscopy.

Certain embodiments provide a computer-implemented system for assessing a patient's risk for recurrent atrial fibrillation (AF) following treatment with an AF treatment modality, the system comprising: a complete at the a processing module that determines, from left atrium (LA) tissue image data of a subject patient that has undergone a first ablative AF treatment with the modality, at least one of: (i) a level of a parameter that is positively proportional or negatively proportional to an amount of ablated tissue in a wall of the LA of the subject patient; and (ii) a spatial distribution, in the LA wall, of a variable indicative of ablated LA tissue; and an output module, in communication with the processing module, that outputs a machine-readable indicator of at least one of: (i) a comparison between the determined level and a threshold level of the parameter; wherein the threshold level is derived from LA tissue image data of at least one other patient who did not experience an AF recurrence for a significant period of time after treatment with the AF treatment modality; wherein, when the level of the parameter is positively proportional to the amount of ablated tissue, levels of the parameter equal to or less than the first threshold level are indicative of a significant risk of AF recurrence; wherein, when the level of the parameter is negatively proportional to the amount of ablated tissue, levels of the parameter equal to greater than the first threshold level are indicative of a significant risk of AF recurrence; and (ii) a map of the spatial distribution, wherein an indication, from the map, of a lack of electrical isolation of one or more pulmonary veins of the subject patient indicates a significant risk of AF recurrence.

In certain embodiments, the machine-readable indicator is readable by at least one of a microprocessor, a computer, a storage medium, a server, a paper, a graphical user interface, a computer display, an LCD, an LED, and a television display.

In certain embodiments, the output module outputs the machine-readable indicator to a receiving device that reads the machine-readable indicator. In certain embodiments, the receiving device comprises at least one of a microprocessor, a computer, a storage medium, a server, a paper, a graphical user interface, a computer display, an LCD, an LED, and a television display.

In certain embodiments, a system comprises the receiving device.

In certain embodiments, a system comprises an imaging module that acquires the LA tissue image data by imaging the patient.

Certain embodiments provide a method of assessing a patient's risk for recurrent atrial fibrillation (AF) following treatment with an AF treatment modality, the method comprising: determining, from left atrium (LA) tissue image data of a patient, a level of a parameter that is positively proportional or negatively proportional to an amount of unhealthy tissue in a wall of the LA of the patient; and outputting, to an output device, a machine-readable indicator of a comparison between (i) the determined level and (ii) a first threshold level of the parameter, the first threshold level derived from LA tissue image data of at least one other patient, who experienced an AF recurrence after treatment with the AF treatment modality; wherein, when the level of the parameter is positively proportional to the amount of unhealthy tissue, levels of the parameter equal to or greater than the first threshold level are indicative of a significant risk of AF recurrence after treatment with the AF treatment modality; wherein, when the level of the parameter is negatively proportional to the amount of unhealthy tissue, levels of the parameter equal to less than the first threshold level are indicative of a significant risk of AF recurrence after treatment with the AF treatment modality.

In certain embodiments, the output device comprises at least one of a microprocessor, a computer, a storage medium, a server, a paper, a graphical user interface, a computer display, an LCD, an LED, and a television display. In certain embodiments, the unhealthy tissue present in the LA wall comprises at least one of a fibrotic tissue, a necrotic tissue, a tissue comprising apoptotic cells, a scar tissue, a tissue having impaired electrical conduction, and an aberrantly electrically remodeled tissue.

In certain embodiments, the AF treatment modality comprises tissue ablation. In certain embodiments, the ablation comprises at least one of radiofrequency ablation, thermal ablation, laser ablation, surgical ablation, and cryoablation. In certain embodiments, the ablation comprises pulmonary vein antrum isolation.

In certain embodiments, the level of the parameter comprises a proportion of fibrotic LA wall tissue relative to a total amount of the LA wall tissue. In certain embodiments, the proportion of fibrotic LA wall tissue relative to a total amount of LA wall tissue comprises a ratio of (i) an imaged volume of fibrotic LA wall tissue to (ii) an imaged total volume of LA wall tissue. In certain embodiments, the proportion is between about 10% and about 20%, and the significant risk comprises a risk of recurrent AF of between about 15% and about 45% risk. In certain embodiments, the proportion is between about 30% and about 40%, and the significant risk comprises a risk of recurrent AF of between about 40% and about 75%.

In certain embodiments, the AF treatment modality comprises administration of a therapeutic substance. In certain embodiments, the therapeutic substance comprises an anti-arrhythmic medication.

In certain embodiments, the tissue image data of the patient is acquired before the patient receives treatment with the AF treatment modality. In certain embodiments, the determining occurs before the patient receives treatment with the AF treatment modality.

In certain embodiments, the method comprises acquiring the image data by detecting a signal of an agent substantially localized at the unhealthy LA tissue. In certain embodiments, the agent comprises a magnetic resonance contrast agent, and wherein the detecting comprises performing magnetic resonance imaging. In certain embodiments, the magnetic resonance imaging comprises delayed enhancement magnetic resonance imaging (DE-MRI). In certain embodiments, the agent comprises gadolinium.

In certain embodiments, a method further comprises localizing the agent to the unhealthy LA tissue by exposing the LA tissue to an antibody or antibody component, coupled to the agent, that binds an epitope present in the unhealthy LA tissue and not present in healthy LA tissue, such that a substantial amount of the agent present at the LA tissue, at the time of image data acquisition, is bound to the unhealthy LA tissues through antibody-epitope binding. In certain embodiments, the epitope comprises at least one of collagen, fibrinogen, fibrin, and fibronectin. In certain embodiments, the antibody or antibody component comprises at least one of a monoclonal antibody, a polyclonal antibody, a Fab peptide, and a single chain variable region peptide.

In certain embodiments, the agent comprises a radioisotope, and wherein the detecting the signal comprises performing at least one of positron emission tomography (PET), radionuclide scanning, and single photon emission computed tomography (SPECT). Certain embodiments, the agent comprises an isotope of at least one of P, I, Tl, Tc, and H. In certain embodiments, the agent comprises a radiopaque marker, and wherein the detecting comprises performing at least one of radiography and fluoroscopy.

Certain embodiments provide a computer-implemented system for assessing a patient's risk for recurrent atrial fibrillation (AF) following treatment with an AF treatment modality, the system comprising: a processing module that determines, from left atrium (LA) tissue image data of a patient, a level of a parameter that is positively proportional or negatively proportional to an amount of unhealthy tissue in a wall of the LA of the patient; and an output module, in communication with the processing module, that outputs a machine-readable indicator of a comparison between (i) the determined level and (ii) a first threshold level of the parameter, the first threshold level derived from LA tissue image data of at least one other patient, who experienced an AF recurrence after treatment with the AF treatment modality; wherein, when the level of the parameter is positively proportional to the amount of unhealthy tissue, levels of the parameter equal to or greater than the first threshold level are indicative of a significant risk of AF recurrence after treatment with the AF treatment modality; wherein, when the level of the parameter is negatively proportional to the amount of unhealthy tissue, levels of the parameter equal to less than the first threshold level are indicative of a significant risk of AF recurrence after treatment with the AF treatment modality.

In certain embodiments, the machine-readable indicator is readable by at least one of a microprocessor, a computer, a storage medium, a server, a paper, a graphical user interface, a computer display, an LCD, an LED, and a television display.

In certain embodiments, the output module outputs the machine-readable indicator to a receiving device that reads the machine-readable indicator. In certain embodiments, the receiving device comprises at least one of a microprocessor, a computer, a storage medium, a server, a paper, a graphical user interface, a computer display, an LCD, an LED, and a television display. In certain embodiments, a system comprises the receiving device.

In certain embodiments, the system comprises an imaging module that acquires the LA tissue image data by imaging the patient. In certain embodiments, the imaging module comprises a magnetic resonance imaging machine.

Certain embodiments of the invention provide methods of assessing a patient's risk for atrial fibrillation (AF) recurrence after receiving treatment with an AF treatment modality, the method comprising: determining, from left atrium (LA) tissue image data of a patient, a level of a parameter that is positively proportional to an amount of unhealthy tissue in a wall of the LA of the patient; and outputting, to an output device, an indicator of a comparison between (i) the determined level and (ii) a first threshold level of the parameter, the first threshold level derived from LA tissue image data of at least one other patient, who experienced an AF recurrence after treatment with the AF treatment modality; wherein levels of the parameter equal to or greater than the first threshold level are indicative of a significant risk of AF recurrence after treatment with the AF treatment modality.

Certain embodiments of the invention provide methods of assessing a patient's risk for atrial fibrillation (AF) recurrence after receiving treatment with an AF treatment modality, the method comprising: determining, from left atrium (LA) tissue image data of a patient, a level of a parameter that is negatively proportional to an amount of unhealthy tissue in a wall of the LA of the patient; and outputting, to an output device, an indicator of a comparison between (i) the determined level and (ii) a first threshold level of the parameter, the first threshold level derived from LA tissue image data of at least one other patient, who experienced an AF recurrence after treatment with the AF treatment modality; wherein levels of the parameter equal to or greater than the first threshold level are indicative of a significant risk of AF recurrence after treatment with the AF treatment modality.

In certain embodiments, the output device comprises at least one of a microprocessor, a computer, a storage medium, a server, a paper, a graphical user interface, a computer display, an LCD, an LED, and a television display.

In certain embodiments, the unhealthy tissue present in the LA wall comprises at least one of a fibrotic tissue, a necrotic tissue, a tissue comprising apoptotic cells, a scar tissue, a poorly conductive tissue, and an aberrantly electrically remodeled tissue. In certain embodiments, the AF treatment modality comprises tissue ablation. In certain embodiments, the ablation comprises at least one of radiofrequency ablation, thermal ablation, laser ablation, surgical ablation, and cryoablation. In certain embodiments, the ablation comprises pulmonary vein antrum isolation.

In certain embodiments, the level of the parameter comprises a proportion of fibrotic LA wall tissue relative to a total amount of LA wall tissue. In certain embodiments, the proportion of fibrotic LA wall tissue relative to a total amount of LA wall tissue comprises a ratio of (i) an imaged volume of fibrotic LA wall tissue to (ii) an imaged total volume of LA wall tissue. In certain embodiments, the proportion is between about 10% and about 20%, and the significant risk comprises a risk of recurrent AF of between about 15% and about 45% risk. In certain embodiments, the proportion is between about 30% and about 40%, and the significant risk comprises a risk of recurrent AF of between about 40% and about 75%.

In certain embodiments, the AF treatment modality comprises administration of a therapeutic substance. In certain embodiments, the therapeutic substance comprises an anti-arrhythmic medication.

Certain embodiments of methods of assessing a patient's risk for atrial fibrillation (AF) recurrence after receiving treatment with an AF treatment modality comprise acquiring the image data by detecting a signal of an agent substantially localized at the unhealthy LA tissue. In certain embodiments, the agent comprises a magnetic resonance contrast agent, and wherein the detecting comprises performing magnetic resonance imaging. In certain embodiments, the magnetic resonance imaging comprises delayed enhancement magnetic resonance imaging (DE-MRI). In certain embodiments, the agent comprises gadolinium.

Certain embodiments of methods of assessing a patient's risk for atrial fibrillation (AF) recurrence after receiving treatment with an AF treatment modality comprise localizing the agent to the unhealthy LA tissue by exposing the LA tissue to an antibody or antibody component, coupled to the agent, that binds an epitope present in the unhealthy LA tissue and not present in healthy LA tissue, such that a substantial amount of the agent present at the LA tissue, at the time of image data acquisition, is bound to the unhealthy LA tissues through antibody-epitope binding. In certain embodiments, the antibody or antibody component specifically recognizes an epitope present in substantial amounts in unhealthy LA wall tissues and in insubstantial amounts in healthful LA wall tissues. In certain embodiments, the antibody or antibody component specifically recognizes an epitope present in substantial amounts in both healthy and unhealthy LA wall tissue, but not susceptible to being bound by the antibody or antibody component in either healthy LA wall tissue or unhealthy LA wall tissue due to, for instance, steric block effects. In certain embodiments, the epitope comprises at least one of collagen, fibrinogen, fibrin, and fibronectin. In certain embodiments, the antibody or antibody component comprises at least one of a monoclonal antibody, a polyclonal antibody, a Fab peptide, and a single chain variable region peptide. In certain embodiments, the agent comprises a radioisotope, and wherein the detecting the signal comprises performing at least one of positron emission tomography, radionuclide scanning, and single photon emission computed tomography. In certain embodiments, the agent comprises at least one of P32, I123, and H3. In certain embodiments, the agent comprises a radiopaque marker, and the detecting comprises performing at least one of radiography and fluoroscopy.

In accordance with various embodiments of the subject disclosure, an association of left atrial (LA) structural remodeling with fibrosis may be determined. For example, the LA structural remodeling may be used as a determinant of fibrosis. In some embodiments, an association of LA structural remodeling with $CHADS_2$ score variables and stroke may be provided. In some embodiments, a novel parameter may be used to help identify patients at risk for stroke.

Certain embodiments provide a method of assessing or estimating a risk of thromboembolic stroke in a patient, the method comprising: determining, from left atrium (LA) tissue image data of a patient, a level of a parameter that is positively proportional or negatively proportional to an amount of abnormal tissue in a wall of the LA of the patient; and outputting, to an output device, a machine-readable indicator of a comparison between (i) the determined level and (ii) a first threshold level of the parameter, the first threshold level derived from LA tissue image data of at least one person, other than the patient, who has a history of atrial fibrillation (AF); wherein, when the level of the parameter is positively proportional to the amount of abnormal tissue, levels of the parameter equal to or greater than the first threshold level are indicative of a significantly increased risk of thromboembolic stroke relative to levels of the parameter less than the first threshold level; wherein, when the level of the parameter is negatively proportional to the amount of abnormal tissue, levels of the parameter equal to or less than the first threshold level are indicative of a significantly increased risk of thromboembolic stroke relative to levels of the parameter greater than the first threshold level.

In certain embodiments, the output device comprises at least one of a microprocessor, a computer, a storage medium, a server, a paper, a graphical user interface, a computer display, an LCD, an LED, and a television display.

In certain embodiments, the abnormal tissue present in the LA wall comprises at least one of a fibrotic tissue, a necrotic tissue, a tissue comprising apoptotic cells, a scar tissue, a tissue having impaired electrical conduction, an aberrantly electrically remodeled tissue, and a structurally remodeled tissue.

In certain embodiments, the level of the parameter comprises a proportion of fibrotic LA wall tissue relative to a total amount of the LA wall tissue. In certain embodiments, the proportion of fibrotic LA wall tissue relative to a total amount of LA wall tissue comprises a ratio of (i) an imaged volume of fibrotic LA wall tissue to (ii) an imaged total volume of LA wall tissue.

In certain embodiments, the tissue image data of the patient is acquired before the patient receives treatment with an AF treatment modality. In certain embodiments, the determining occurs before the patient receives treatment with the AF treatment modality.

In certain embodiments, the method further comprises acquiring the image data by detecting a signal of an agent substantially localized at the abnormal LA tissue. In some embodiments, the agent comprises a magnetic resonance contrast agent, and the detecting comprises performing magnetic resonance imaging. In certain embodiments, the magnetic resonance imaging comprises delayed enhancement magnetic resonance imaging (DE-MRI). In some embodiments, the agent comprises gadolinium.

In some embodiments, the method further comprises localizing the agent to the abnormal LA tissue by exposing the LA tissue to an antibody or antibody component, coupled to the agent, that binds an epitope present in the abnormal LA tissue and not present in normal LA tissue, such that a substantial amount of the agent present at the LA tissue, at the time of image data acquisition, is bound to the abnormal LA tissues through antibody-epitope binding. In some embodiments, the epitope comprises at least one of collagen, fibrinogen, fibrin, and fibronectin. In some embodiments, the antibody or antibody component comprises at least one of a monoclonal antibody, a polyclonal antibody, a Fab peptide, and a single chain variable region peptide. In some embodiments, the agent comprises a radioisotope, and the detecting the signal comprises performing at least one of positron emission tomography (PET), radionuclide scanning, and single photon emission computed tomography (SPECT). In some embodiments, the agent comprises an isotope of at least one of P, I, Tl, Tc, and H. In some embodiments, the agent comprises a radiopaque marker, and the detecting comprises performing at least one of radiography and fluoroscopy.

In certain embodiments, the method further comprises: determining, of the patient, at least one of an existence and a degree of at least one clinical risk factor for stroke other than the level of the parameter; and estimating a risk of thromboembolic stroke based on the level of the parameter and the at least one of the existence and the degree of the at least one clinical risk factor. In some embodiments, the at least one clinical risk factor comprises at least one of congestive heart failure, hypertension, age, diabetes, and prior stroke. In some embodiments, the patient has a history of AF.

Certain embodiments provide a computer-implemented system for assessing a risk of thromboembolic stroke in a patient, the system comprising: a processing module that determines, by a computer, from left atrium (LA) tissue image data of a patient, a level of a parameter that is positively proportional or negatively proportional to an amount of abnormal tissue in a wall of the LA of the patient; and an output module, in communication with the processing module, that outputs a machine-readable indicator of a comparison between (i) the determined level and (ii) a first threshold level of the parameter, the first threshold level derived from LA tissue image data of at least one person, other than the patient, who has a history of atrial fibrillation (AF); wherein, when the level of the parameter is positively proportional to the amount of abnormal tissue, levels of the parameter equal to or greater than the first threshold level are indicative of a significantly increased risk of thromboembolic stroke relative to levels of the parameter less than the first threshold level; wherein, when the level of the parameter is negatively proportional to the amount of abnormal tissue, levels of the parameter equal to or less than the first threshold level are indicative of a significantly increased risk of thromboemoblic stroke relative to levels of the parameter greater than the first threshold level.

In certain embodiments, the machine-readable indicator is readable by at least one of a microprocessor, a computer, a storage medium, a server, a paper, a graphical user interface, a computer display, an LCD, an LED, and a television display. In some embodiments, the output module outputs the machine-readable indicator to a receiving device that reads the machine-readable indicator. In some embodiments, the receiving device comprises at least one of a microprocessor, a computer, a storage medium, a server, a paper, a graphical user interface, a computer display, an LCD, an LED, and a television display. In some embodiments, the system further comprises the receiving device.

In some embodiments, the system further comprises an imaging module that acquires the LA tissue image data by imaging the patient. In some embodiments, the imaging module comprises a magnetic resonance imaging machine.

In certain embodiments, the processing module determines, of the patient, at least one of an existence and a degree of at least one clinical risk factor for stroke other than the level of the parameter. In some embodiments, the processing module estimates a risk of thromboembolic stroke based on the level of the parameter and the at least one of the existence and the degree of the at least one clinical risk factor. In some embodiments, the at least one clinical risk factor comprises at least one of congestive heart failure, hypertension, age, diabetes, and prior stroke.

Certain embodiments provide a method of assessing a risk of thromboembolic stroke in a patient, the method comprising: acquiring image data; determining an indicator of a degree of fibrosis of a patient's left atrium (LA) based on the image data; and estimating a level of risk of thromboembolic stroke of the patient based on the indicator.

In some embodiments, the image data is acquired before the patient receives treatment with an atrial fibrillation (AF) treatment modality. In some embodiments, the determining the indicator occurs before the patient receives treatment with the AF treatment modality.

In some embodiments, the image data is acquired by detecting a signal of an agent substantially localized at abnormal tissue in a wall of the LA. In some embodiments, the agent comprises a magnetic resonance contrast agent, and the acquiring comprises performing magnetic resonance imaging. In some embodiments, the magnetic resonance imaging comprises delayed enhancement magnetic resonance imaging (DE-MRI). In some embodiments, the agent comprises gadolinium.

In some embodiments, the method further comprises localizing the agent to the abnormal LA tissue by exposing the LA tissue to an antibody or antibody component, coupled to the agent, that binds an epitope present in the abnormal LA tissue and not present in normal LA tissue, such that a substantial amount of the agent present at the LA tissue, at the time of image data acquisition, is bound to the abnormal LA tissues through antibody-epitope binding. In some embodiments, the epitope comprises at least one of collagen, fibrinogen, fibrin, and fibronectin. In some embodiments, the antibody or antibody component comprises at least one of a monoclonal antibody, a polyclonal antibody, a Fab peptide, and a single chain variable region peptide. In some embodiments, the agent comprises a radioisotope, and wherein the detecting the signal comprises performing at least one of positron emission tomography (PET), radionuclide scanning, and single photon emission computed tomography (SPECT). In some embodiments, the agent comprises an isotope of at least one of P, I, Tl, Tc, and H. In some embodiments, the agent comprises a radiopaque marker, and wherein the detecting comprises performing at least one of radiography and fluoroscopy. In some embodiments, the patient has a history of atrial fibrillation.

In certain embodiments, the method further comprises: determining, of the patient, at least one of an existence and a degree of at least one clinical risk factor for stroke; and estimating the level of risk of thromboembolic stroke based on the at least one of the existence and the degree of the at least one clinical risk factor. In some embodiments, the at least one clinical risk factor comprises at least one of congestive heart failure, hypertension, age, diabetes, and prior stroke.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

FIG. 1 also shows a volume rendered color model (View (B) of FIG. 1) for a patient having AF and for a healthy subject. FIG. 1 also shows an electroanatomic map acquired during invasive EP study. Discrete patterns of low voltage (within bounded white lines) were detected in the left posterior wall and the septum in the patient shown (View (C) of FIG. 1).

Figure 16:
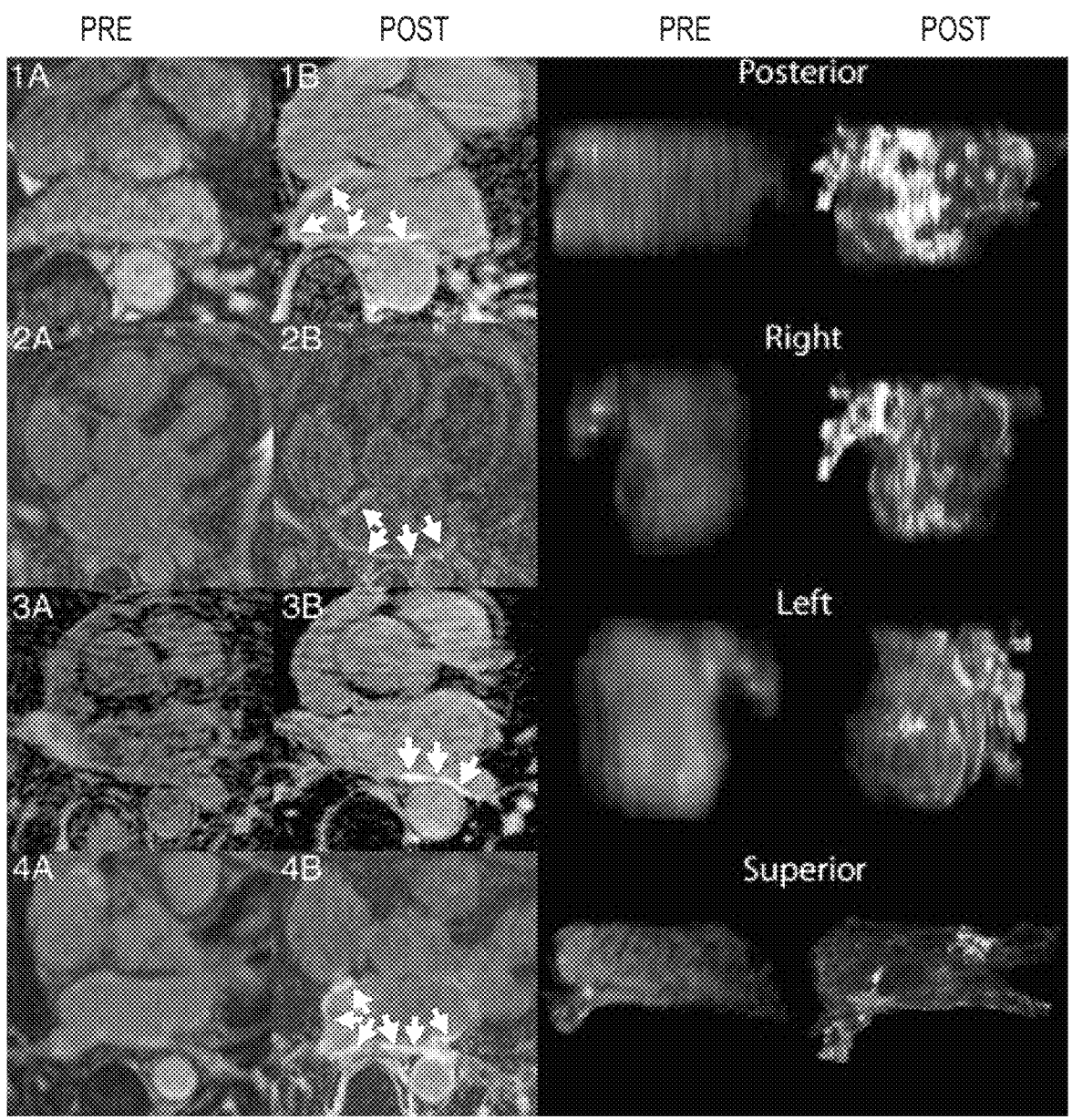

The left panels of FIG. 16 show DE-MRI models of LA wall slices at baseline (A) and 3 months after PVAI (B) on three dimensional navigated DE-MRI in 4 different patients. The right panels of FIG. 16 show multiple views (posterior, right, left, and superior) of three-dimensional DE-MRI LA wall models, reconstructed from DE-MRI slice data from Patient #1 before and after PVAI. Post-PVAI hyperenhancement of LA wall is clearly seen (arrows) in regions subjected to RF ablation.

Figure 17:
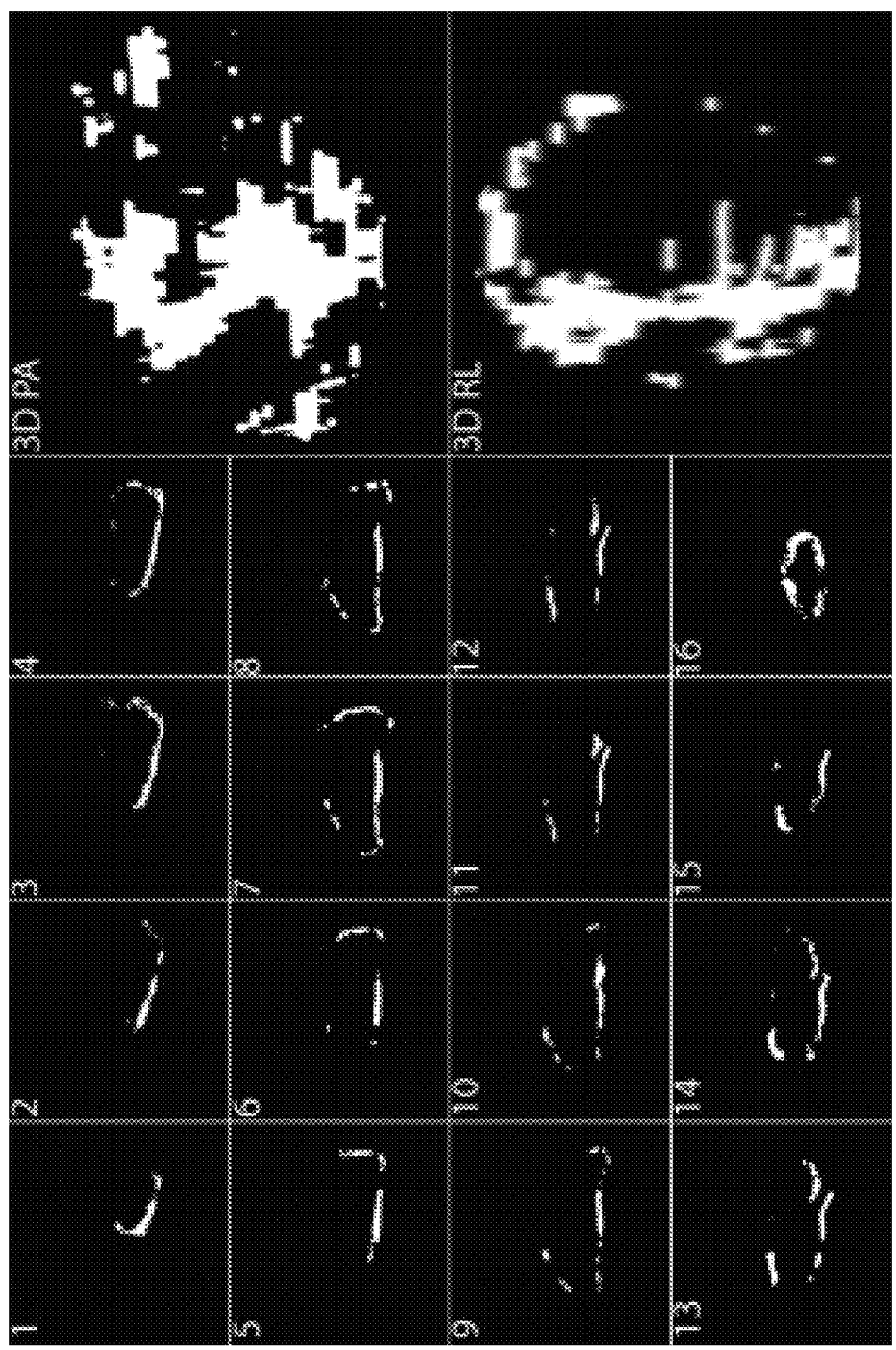

FIG. 17 shows determination of left atrial wall injury using a threshold based on the normal wall regions. FIG. 17, panels 1 to 16, show extent of the LA wall injury at 5 standard deviations in a subset of slices from the DE-MRI scanning of Patient #1. Three-dimensional reconstruction of the full data set is shown in the right panels (3DPA and 3DRL views). Using these methods, LA injury volume can be determined and calculated as a percentage of total LA wall volume.

Figure 18:
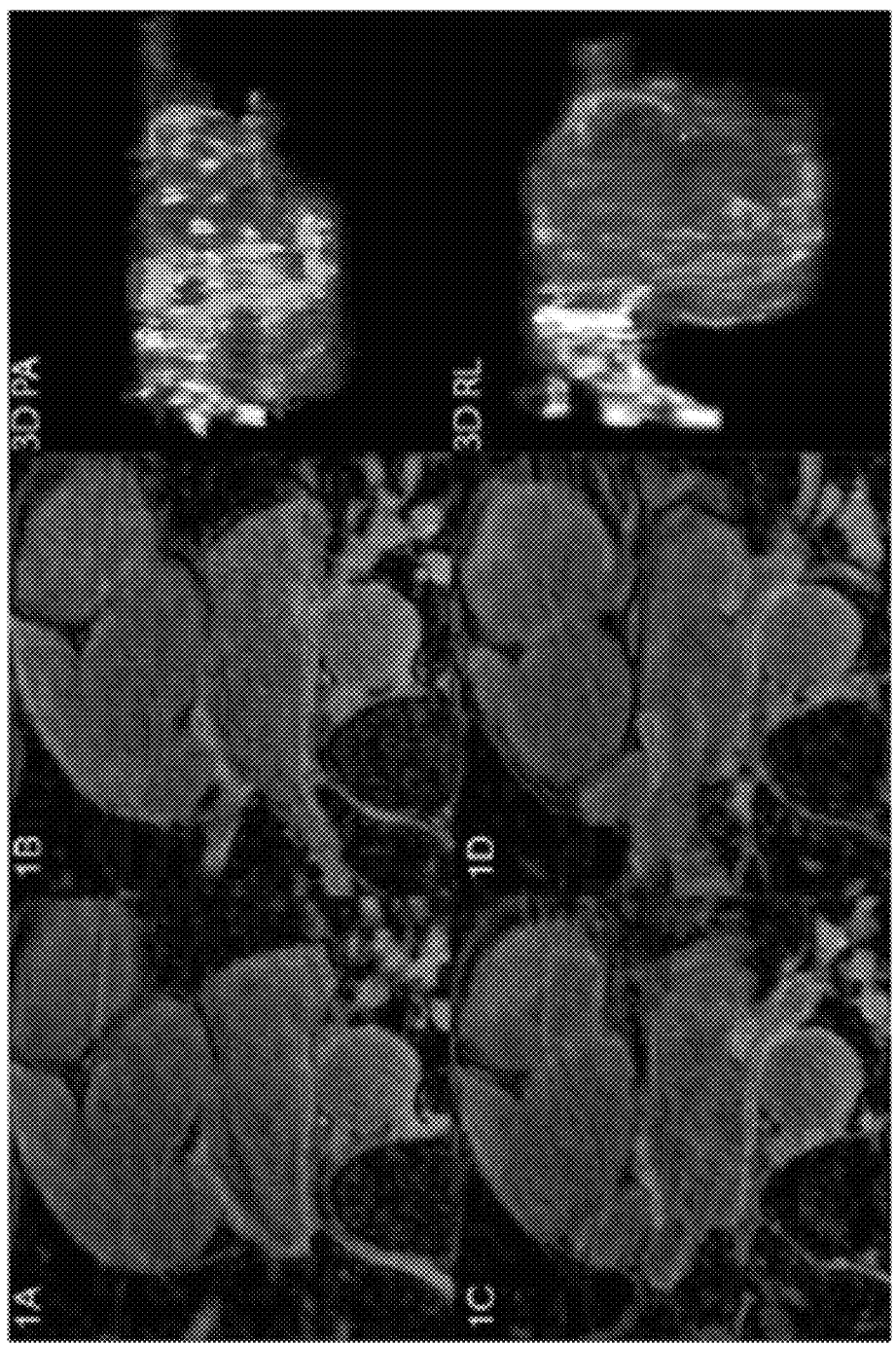

FIG. 18, panels 1A to 1D, show 4 examples of two-dimensional DE-MRI slices of LA wall tissue from Patient #1 that show a close correlation of LA wall tissue injury, as determined by automated methods using a three standard deviation cutoff value. The right panels of FIG. 18 show a three-dimensional overlay of full data sets (3DPA and 3DRL). LA injury mask (blue), as determined by automated methods, should substantially overlay hyperenhanced areas (white) of injured LA wall tissue, as determined in DE-MRI. Although the left pulmonary veins are white on MRI, this enhancement is attributable to navigator interference, not injured tissue. The pulmonary veins are shown to help with anatomical orientation, and are excluded from raw data used to produce injury mask by automated methods.

Figure 19:
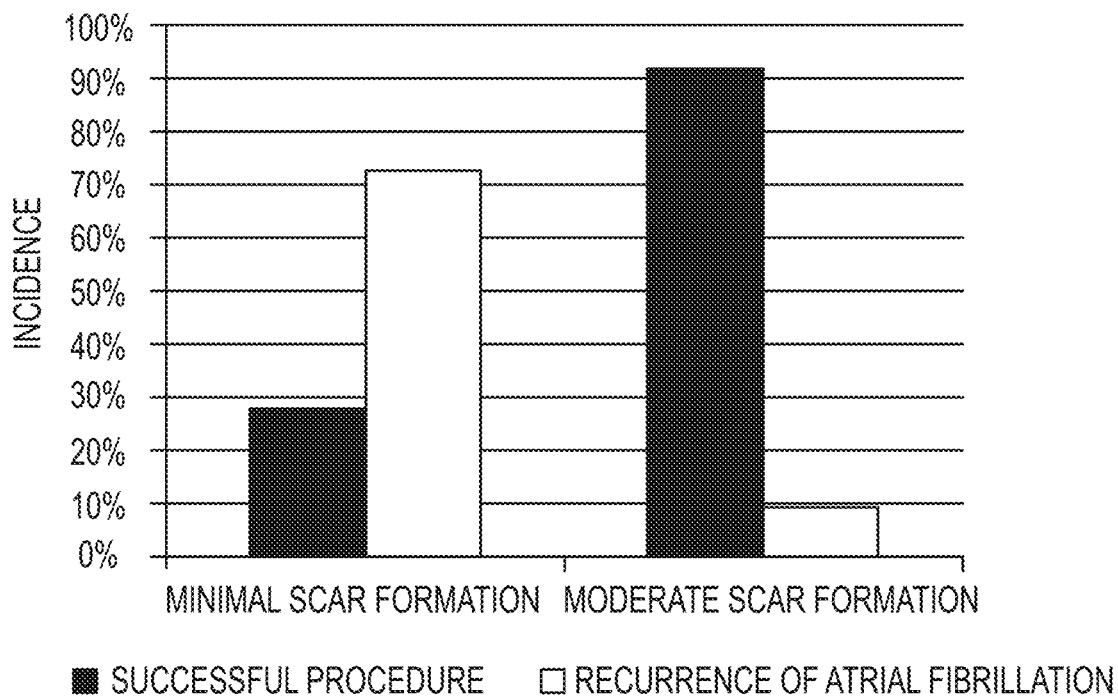
Figure 19:
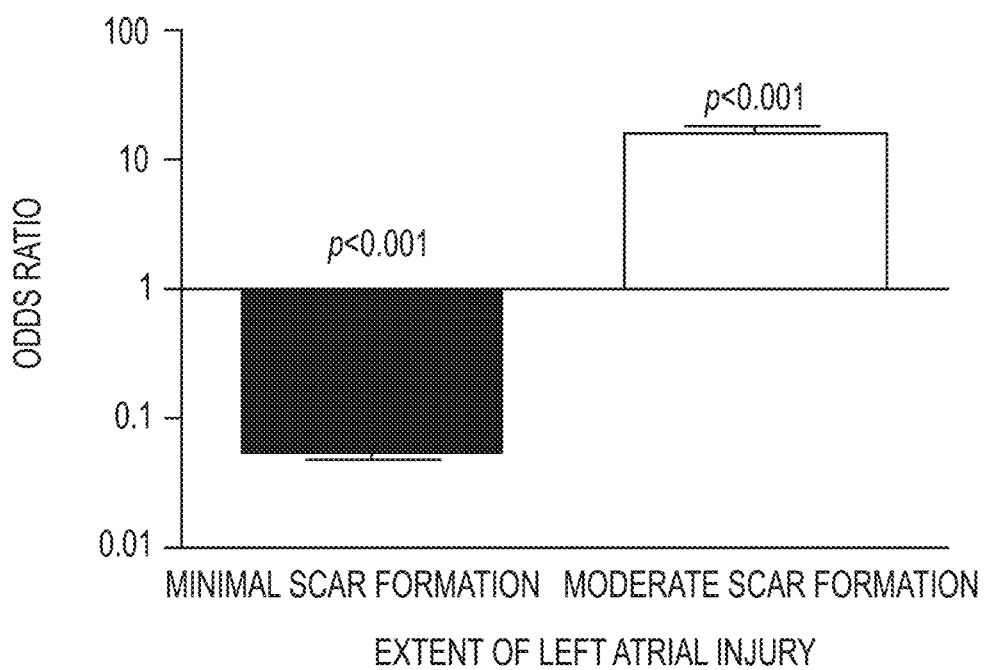

FIG. 19 provides graphical representations of the association, a statistical significance thereof, between atrial fibrillation recurrences and clinical success according to LA wall injury following catheter-based PVAI. Patients with minimal scar formation at 3 months after the procedure (>13% of LA myocardial volume enhancement on DE-MRI) had low procedural success and a high recurrence of atrial fibrillation, whereas patients with moderate scar formation at 3 months had very high procedural success and a low recurrence of atrial fibrillation.

Figure 20:
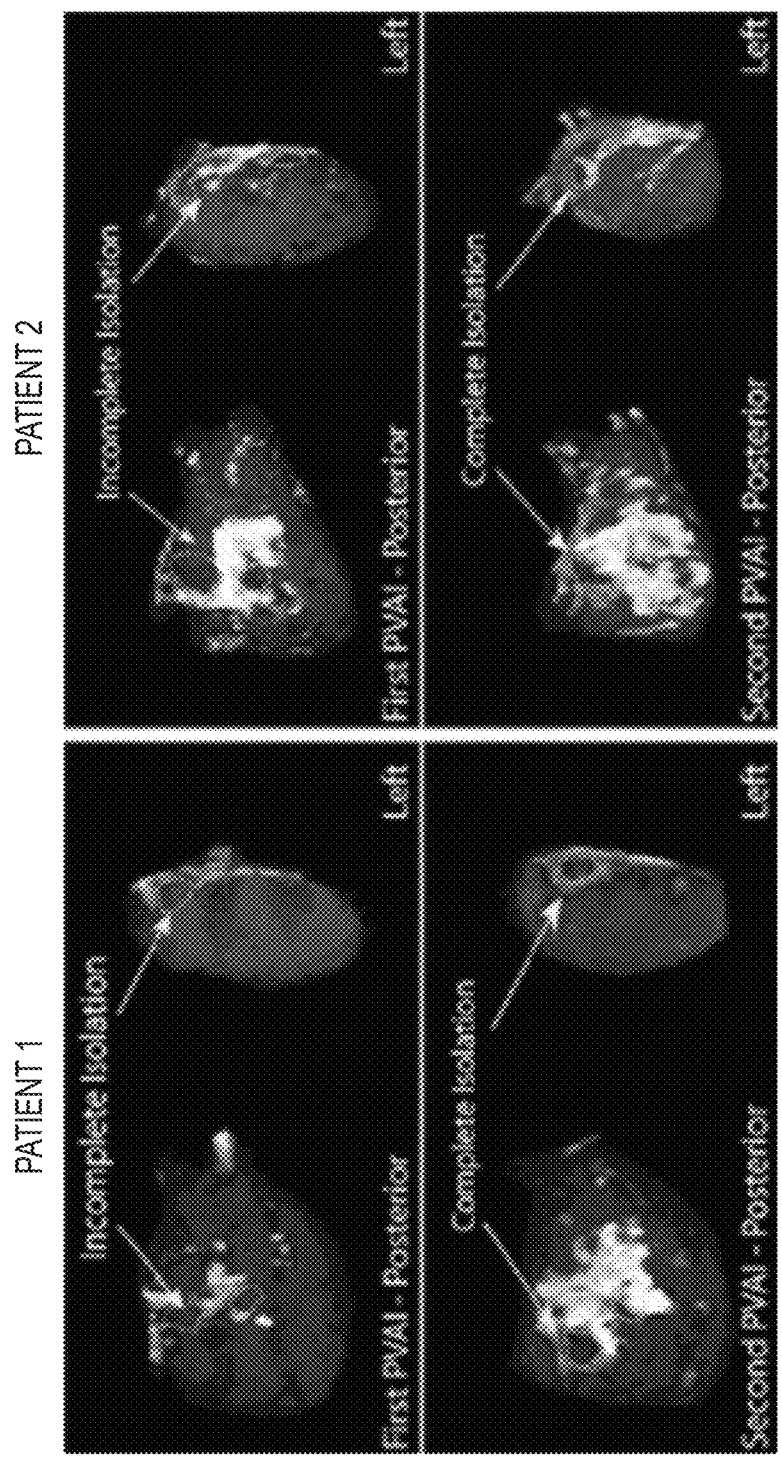

FIG. 20 shows posterior and left lateral view DE-MRI models of LA wall tissues of two patients, three months after each patient had undergone a failed PVAI treatment. Incomplete scar formation near the antrum of the pulmonary veins appears in the DE-MRI models of both patients. The gap in RF lesions at the pulmonary vein antrum (purple) correlated with incomplete electrical isolation of the left superior pulmonary vein. FIG. 20 also shows posterior and left lateral view DE-MRI models of LA wall tissues of the two patients 3 months after undergoing a repeat PVAI procedure. Complete scar formation (white/orange), which isolates the pulmonary veins, appears in the DE-MRI, and both patients were free of AF.

FIGS. 21A and 21B illustrate delayed-enhancement MRI left atrial structural remodeling according to the history of strokes and risk profile, in accordance with various embodiments of the subject disclosure.

FIGS. 21C, 21D, and 21E illustrate examples of delayed enhancement MRI images, in accordance with various embodiments of the subject disclosure.

Figure 22A:
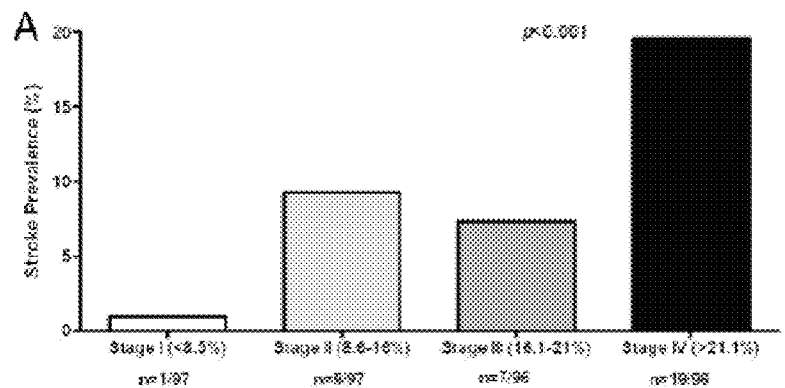
Figure 22B:
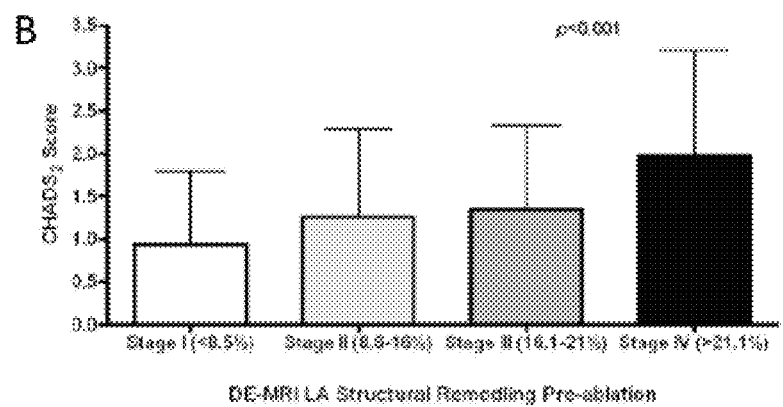
Figure 22C:
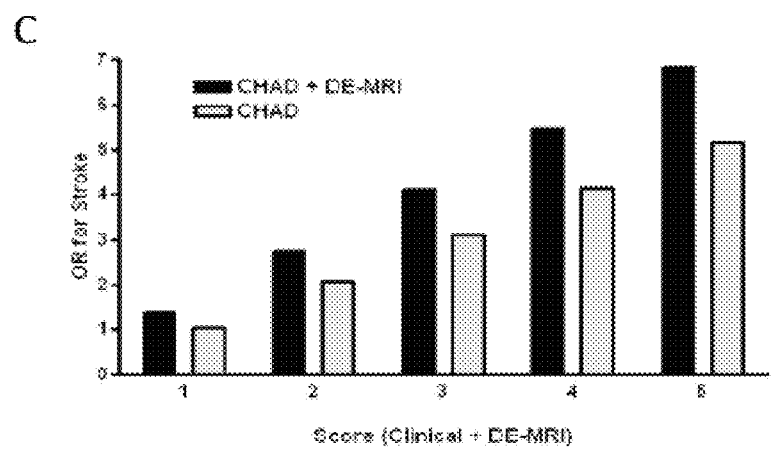

FIGS. 22A, 22B, and 22C present graphical illustrations of the incidence of stroke among various levels of LA structural remodeling, in accordance with various embodiments of the subject disclosure.

DETAILED DESCRIPTION

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

Therapeutic Outcome Assessment/Therapeutic Success Prediction for Atrial Fibrillation AF is associated with pathologies of the LA such as necrosis, fibrosis, scarring, reduced endocardial voltage, irregular cardiac rhythm, and combinations thereof. AF is often a progressive disease, which suggests a self perpetuating component to AF. Rapidly paced cardiac myocytes have been shown to release factors that induce a nearly four-fold increase in collagen-1 and fibronectin-1 in LA tissue, which suggests a link between the degree of LA tissue fibrosis and the severity of AF. In addition, animal studies have established an increased tendency for AF when LA tissue fibrosis is experimentally induced. Furthermore, certain studies have shown that fibrosis of LA tissues can lead to AF induction by burst or premature atrial pacing that would fail to result in AF in normal hearts having a low amount of LA tissue fibrosis.

Spatial distribution and degree of pathologic, low voltage LA tissue appears to influence fibrillatory dynamics such as the location and variability of wavefront breakthroughs. LA tissue pathologies and structural electrical remodeling in LA tissue associated with AF can promote formation of circuits needed for re-entry, resulting in atrial arrhythmia recurrence. Although the mechanisms underlying LA tissue pathologies in patients that have recurrent AF are complex and likely not fully delineated, changes in electrical activation in patients that have recurrent AF often manifest as a reduction in myocardial voltage and a reduction in the effective refractory period in heartbeat rhythm.

Determining the amount of unhealthy LA tissues in patients that have AF can be useful in selecting stage appropriate AF treatments, such as antiarrhythmic drug therapy, anticoagulant drug therapy, cardioversion, use of pacemakers, PVAI, and combinations thereof.

As used herein, "pathologic" LA tissue and "unhealthy" LA tissue include ischemic, apoptotic, necrotic, fibrotic, scar, low voltage, and/or aberrantly electrically remodeled LA tissue that may or may not result in, or from, irregular heart contraction rhythms associated with AF. In certain embodiments, determining, from LA tissue image data of a patient, a level of a parameter that is positively or negatively proportional to an amount of unhealthy or healthy tissue in a wall of the LA of the patient, respectively, can involve an estimation of the actual amount of unhealthy or healthy tissue present in the LA wall because, e.g., the precise proportionality between a level of the parameter and the unhealthy or healthy, respectively, among tissue in the LA wall of the patient can vary based on factors such as the age of the patient, the sex of the patient, the physical condition of the patient, and the method by which the LA tissue image data was acquired.

As used herein, AF treatment modalities include, e.g., antiarrhythmic drug therapy, anticoagulant drug therapy, cardioversion, use of pacemakers, PVAI, and combinations thereof, each representing a different modality. Any specific treatment regimen or dose schedule can be considered a different modality.

In certain embodiments, the acquiring of image data of a patient's LA wall tissue by detecting a signal of an agent substantially localized at the unhealthy LA tissue comprises administering, to the patient, an amount of signal agent comprising at least one of a magnetic resonance contrast agent, a radioisotope, an antibody coupled to a radiopaque moiety, an antibody component coupled to a radiopaque moiety, an antibody coupled to a radioisotope, and an antibody component coupled to a radioisotope effective to result in exposing the LA wall tissue to a concentration of the signal agent in a range of from about 1 nanomolar to about 1 molar. In certain embodiments, such concentrations of signal agent include about 1 nanomolar, about 10 nanomolar, about 100 nanomolar, about 1 micromolar, about 10 micromolar, about 100 micromolar, about 1 millimolar, about 10 millimolar, about 100 millimolar, and about 1 molar.

In certain embodiments, doses of administered signal agent can range from about 1 nanogram signal agent per kilogram of the patient's body weight to about 1 g of signal agent per kilogram of the patient's body weight. In certain embodiments, doses of signal agent can be about 1 nanogram/kilogram, about 10 nanograms/kilogram, about 100 nanograms/kilogram, about 1 milligram/kilogram, about 10 milligrams/kilogram, and about 100 milligrams/kilogram, each of the patient's body weight.

In certain embodiments, administration of the signal agent to the patient can be achieved by at least one of injection, ingestion, inhalation, suppository, and gavage.

Certain embodiments of the present invention provide non-invasive methods of detecting healthy regions, unhealthy regions, and combinations thereof, of LA tissue in a mammal. Certain embodiments provide non-invasive methods of determining a propensity of a mammal that has a determined amount of unhealthy LA tissue to manifest improved LA health, function, etc. in response to a cardiac treatment. In certain embodiments, a non-invasive method of detecting pathologic regions of LA tissue comprises imaging with MR, DE-MR, positron emission tomography (PET), X-ray autoradiography, ultrasound, and combinations thereof. In certain embodiments, cardiac disease can comprise, for instance, AF, myocardial infarction, myocardial ischemia, cardiac embolism, and combinations thereof. In certain embodiments, a cardiac treatment can comprise antiarrhythmic drug therapy, anticoagulant drug therapy, cardioversion, use of pacemaker, ablative PVAI, and combinations thereof.

Certain embodiments involve use of noninvasive imaging to create a map of the LA wall, the map illustrating a distribution and/or degree of healthy and unhealthy tissues in the LA wall of a patient. As used herein, the term, "LA wall," refers to an area comprising tissue of the heart within or adjacent to an area delimited by the following cardiac structures: the coronary sinus, the pulmonary artery, the right pulmonary veins, and the left pulmonary veins.

In certain embodiments, cutoff points between mild amounts of unhealthy LA wall tissue, observed as, e.g., enhancement in DE-MRI of the invention, and moderate amounts of unhealthy LA wall tissue and between moderate amounts of unhealthy LA wall tissue and extensive amounts of unhealthy LA wall tissue identify groups of mammals having mild, moderate, and extensive amounts of unhealthy LA tissue and disparate likelihoods of experiencing a recurrence of a cardiac event, such as AF, after undergoing an AF treatment modality.

In certain embodiments, an amount of healthy or unhealthy LA wall tissue can be reported as the percentage of LA wall tissue relative to the whole of LA wall tissue or relative to a subregion of LA wall tissue, which can comprise a type of LA wall tissue (e.g., healthy or unhealthy tissue) or a location of the LA wall (e.g. a region adjacent a coronary structure). In certain embodiments, each of a healthy and an unhealthy percentage of LA wall tissue can comprise a ratio of areas of LA wall tissue. Such an area can substantially comprise a surface area of the LA wall or an interior area of the LA wall, and such an area of the LA wall can comprise a contiguous area of the LA wall or the sum of noncontiguous areas of the LA wall. In certain embodiments, each of a healthy and an unhealthy percentage of LA wall tissue can comprise a ratio of volumes of LA wall tissue. Such a volume of the LA wall can comprise a contiguous volume of the LA wall or the sum of noncontiguous volumes of the LA wall.

In certain embodiments, a cutoff point between mild and moderate amounts of unhealthy LA tissues can be in a range of from about 5% to about 25%, including about 5%, about 7.5%, about 10%, about 12.5%, about 15%, about 17.5%, about 20%, about 22.5%, and about 25%. In certain embodiments, a cutoff point between moderate and extensive amounts of unhealthy LA wall tissue can be in a range of from about 25% to about 50%, including about 25%, about 27.5%, about 30%, about 32.5%, about 35%, about 37.5%, about 40%, about 42.5%, about 45%, about 47.5%, and about 50%.

Certain embodiments of the present invention provide noninvasive methods of detecting and quantifying ablated (e.g., scarred) LA tissue following ablative PVAI treatment of patients having AF. Certain embodiments provide three-dimensional DE-MRI scanning sequences and processing methods by which LA wall scarring can be visualized at high resolution after radiofrequency ablation. Certain embodiments of the present invention provide non-invasive methods for obtaining high resolution images of ablated (e.g., scarred) LA tissue resulting from ablative PVAI AF treatment using two-dimensional or three-dimensional DE-MRI scanning and processing methods. Such DE-MRI visualizations can indicate the likelihood of a positive or negative outcome for a patient that has undergone an ablative PVAI AF treatment. In certain embodiments, such DE-MRI visualizations that indicate a likelihood of a negative outcome for a patient's ablative PVAI AF treatment further indicate a likelihood of a positive or negative outcome for a potential repeat ablative PVAI AF treatment.

EXAMPLES

We developed DE-MRI methods that provide high resolution images illustrating amounts and distributions of healthy and unhealthy LA wall tissues in patients. We also developed methods for analyzing such images to provide a patient's likely outcome of ablative PVAI AF treatment, a negative outcome comprising a recurrence of AF following ablative PVAI AF treatment and a positive outcome comprising non-recurrence of AF on ablative PVAI AF treatment.

Patients that experienced recurrence of AF following ablative PVAI AF treatment exhibited a significantly greater amount of unhealthy LA tissue detected by DE-MRI as compared to patients that did not experience AF recurrence following ablative PVAI AF treatment. Patients having extensive amounts of unhealthy LA tissue presented exclusively with persistent forms of AF. Multivariate analysis demonstrated that the greatest degree of variance for ablative PVAI AF treatment outcome correlated to the degree of unhealthy LA tissue, observed as enhancement in the LA wall by DE-MRI (Table 3). These results indicate that extensive amounts of unhealthy LA wall tissue in a patient are predictive of a reduced likelihood of positive outcome of ablative PVAI AF treatment (i.e., an increased risk of AF recurrence following ablative PVAI AF treatment). DE-MRI detection of amounts and distributions of unhealthy LA tissues therefore allows for patient selection in ablative PVAI AF treatment and in repeat PVAI AF treatment.

Figure 7A:
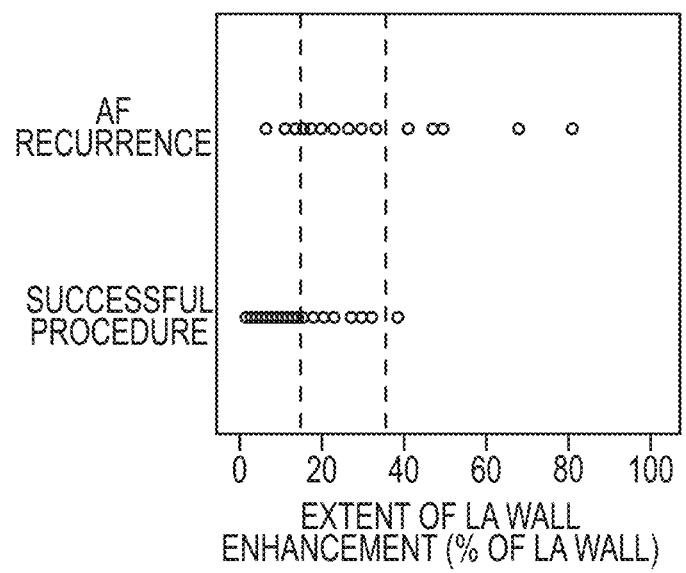
FIG. 7A provides a graphical representation of atrial fibrillation recurrence and non-recurrence, after an AF treatment, as a function of the extent of LA wall enhancement.
Figure 7B:
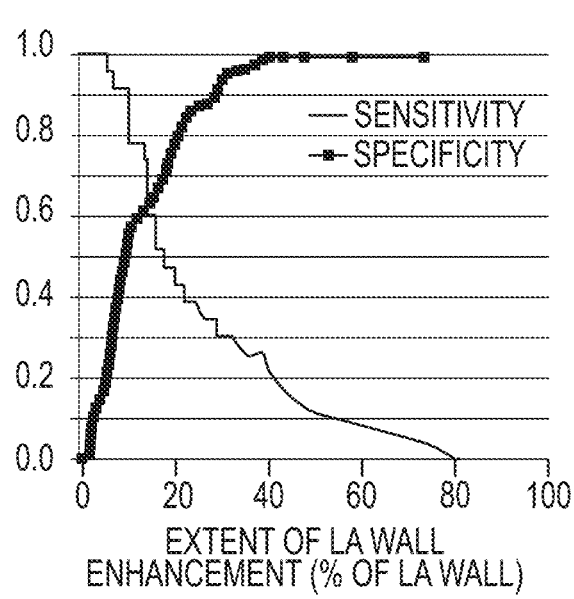
FIG. 7B provides a graphical representation of sensitivity and specificity as a function of the extent of LA wall enhancement.
Figure 7C:
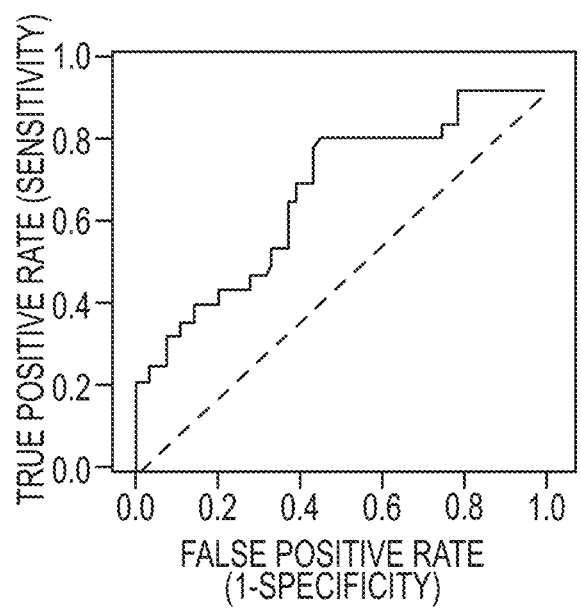
FIG. 7C provides a graphical representation of sensitivity as a function of specificity.

FIGS. 7A, 7b, and 7C show data distributions inclusive of patients who, following ablative PVAI AF treatment, experienced AF recurrence and of patients who did not experience AF recurrence. Subsequent analysis of the sensitivity and specificity curves support two cutoffs dividing minimal, moderate, and extensive amount of unhealthy LA wall tissue: a lower cutoff (~15% of unhealthy LA wall tissue) above which there is a rapid rise in the specificity of LA wall enhancement as a predictor for AF recurrence following ablative PVAI AF treatment without a substantial loss of sensitivity, and an upper cutoff (~35% of unhealthy LA wall tissue) above which the specificity is nearly 100% for patients experiencing AF recurrence following ablative PVAI AF treatment.

Data presented herein demonstrate that not only the extent but also the location of unhealthy LA wall tissue, observed as enhancement in DE-MRI images, comprises an important predictor of positive or negative outcome for ablative PVAI AF treatment (Table 2). Patients that experienced a recurrence of AF following ablative PVAI AF treatment showed unhealthy LA wall tissues in all portions of the LA; whereas patients that did not experience a recurrence of AF following ablative PVAI AF treatment showed a distribution of unhealthy LA tissues primarily restricted to the posterior atrial wall and septum. In multivariate analysis, the extent of unhealthy LA wall tissues was more strongly associated with more persistent forms of atrial arrhythmia (Table 3).

Example 1

Atrial Fibrillation Patients

DE-MRI scans were performed on 81 patients referred to the University of Utah for ablative PVAI AF treatment. Table 1 lists demographics of the study patients.

Prior to ablative PVAI AF treatment, the 81 patients underwent MRI scanning to determine pulmonary vein anatomy, LA area, and LA wall thickness. LA appendage thrombus was ruled out via transesophageal echocardiogram (TEE). Left ventricular ejection fraction was obtained by biplane transthoracic echocardiogram. LA volume was determined by segmentation of blood volume on MRI angiography images.

Baseline AF type was categorized as either paroxysmal AF, which comprises an episode of AF that self terminated within seven days, or persistent AF, which comprises an episode of AF lasting longer than seven days. Patients that required either pharmacological treatment or medical or electrical cardioversion to end their AF were considered to have persistent AF. Data regarding patient response to antiarrhythmic drugs was assessed through retrospective chart review. Failure to respond to a given medication was defined as having an episode of breakthrough AF while on the antiarrhythmic drug.

Six healthy subjects without a history of AF or other cardiac arrhythmia also underwent DE-MRI acquisition in the same manner as patients presenting for ablative PVIA AF treatment. The healthy subjects included four men and two women having a mean age of $44.2 \pm 21.2$ years (range=26 to 81 years). The healthy subjects did not undergo EA mapping.

Delayed Enhancement MRI Acquisition

All patients and healthy subjects underwent MRI studies on a 1.5 Tesla Avanto clinical scanner (Siemens Medical Solutions, Erlangen, Germany) using a TIM phased-array receiver coil or 32 channel cardiac coil (Invivo Corp., Gainesville, Fla.). DE-MRI scans were acquired approximately 15 minutes after contrast agent injection (dose=0.1 mmol per kilogram of body weight [Multihance, Braco Diagnostic Inc., Princeton, N.J.]) using 3D inversion recovery prepared, respiration navigated, ECG-gated, gradient echo pulse sequence with fat saturation. Typical acquisition parameters were: free-breathing using navigator-gating, a transverse imaging volume with true voxel size=$1.25 \times 1.25 \times 2.5$ mm, flip angle=$22°$, repetition time/echo time=$6.1/2.4$ ms, inversion time (TI)=230-320 ms, parallel imaging using GRAPPA technique with R=2 and 42 reference lines. ECG gating was used to acquire a subset of phase encoding views during diastolic phase of the LA cardiac cycle. Typical scan time for the DE-MRI study was 5-9 minutes, depending on patient respiration and heart rate. $73/81$ patients (90.1%) were in normal sinus rhythm during MRI acquisition. Patients in AF at the time of clinical presentation were cardioverted to restore normal sinus rhythm prior to MRI scanning.

In the healthy subject group, DE-MRI scans were acquired at 15 and again at 30 minutes following contrast injection. In a subset of four healthy subjects, a third DE-MRI scan was acquired 45 minutes following contrast injection. Image processing and quantification was performed in the same manner as described above for ablative PVAI AF treatment patients.

Three Dimensional Electroanatomic Mapping

At the beginning of each ablative PVAI AF treatment, a detailed voltage map of the LA was obtained in all patients using the three-dimensional EA mapping system, CARTOMERGE (Biosense Webster, Diamond Bar, CA). The physician performing the ablative PVAI AF treatment was blinded to the DE-MRI results. EA measurement points were substantially evenly distributed throughout the LA wall, and bipolar voltage was measured from peak to peak with the signal filtered from 30 to 400 Hz. Mapping catheter-LA wall contact (Navistar-ThermoCool, Biosense Webster) was visually confirmed using fluoroscopy, intracardiac echocardiography, and a CARTO 3-D navigation system. $48/81$ patients (59.3%) were in normal sinus rhythm during EA mapping, $27/81$ patients (33.3%) were in AF during EA mapping, and $6/81$ patients (7.4%) were in atrial flutter during EA mapping.

Atrial Fibrillation Ablation Procedure

The ablation of ablative PVAI AF treatment was performed under intracardiac echocardiography (ICE) in all patients. A 10F, 64 element phased array ultrasound catheter (AcuNav, Siemens Medical Solutions USA, Inc) was used to visualize the interatrial septum and to guide the transseptal puncture. A circular mapping catheter (Lasso, Biosense Webster) and an ablation catheter were inserted into the LA. ICE was used to define the pulmonary vein ostia and their antra as well as the posterior LA wall. ICE was also used to position the circular mapping and ablation catheters. All patients underwent ablative PVAI AF treatment, defined as electrical disconnection of the PV antrum from the LA together with posterior LA wall and septal debulking.

Following the ablative PVAI AF treatment, all patients were observed on a telemetry unit for 24 hours. Following discharge, patients underwent 8 weeks of patient triggered and autodetected event monitoring. Patients activated the telemetry unit any time they felt symptoms, and were assessed at three months, six months, and one year after the ablative PVAI AF treatment. Patients continued anticoagulation therapy with warfarin (international normalized ratio of 2.0-3.0) for a minimum of three months following ablative PVAI AF treatment.

A positive outcome for ablative PVAI AF treatment was defined as freedom from AF, atrial tachycardia, and atrial flutter, while off of antiarrhythmic medications, three months following ablative PVAI. To confirm the absence of asymptomatic AF, all patients received a 48-hour Holter ECG recording within 24 hours following the procedure and an 8-day Holter ECG at 3, 6, and 12 month follow-ups. Recurrences of AF were therefore determined from patient reporting, event monitoring, Holter monitoring, and ECG data, and were defined as any symptomatic or asymptomatic detected episode of AF, atrial tachycardia, or atrial flutter lasting greater than 30 seconds.

Analysis of DE MRI Images

Three-dimensional visualization and segmentation of MRI scans were performed using OsiriX 2.7.5. The LA and pulmonary tree were manually segmented in all patients and visually verified in the image stack prior to rendering and visualization. Initial visualization used a MIP to assess contrast consistency followed by volume rendering using a ray cast engine with linear table opacity. A color look-up table mask was applied to the rendered images for improved differentiation of enhanced and non-enhanced tissue.

In all images, the epicardial and endocardial borders were manually contoured using image display and analysis software written in MATLAB (The Mathworks Inc., Natick, Mass.). The relative extent of unhealthy LA tissue was quantified within the LA wall using a threshold based algorithm. Patients were assigned to one of three groups based on the extent of unhealthy LA myocardium, observed as enhancement in DE-MRI images. Patients having 15% or less unhealthy LA tissue were defined as having a mild amount of unhealthy LA tissue. Patients having between 15% and 35% unhealthy LA tissue were defined as having a moderate amount of unhealthy LA tissue. Patients having 35% or more unhealthy LA tissue were defined as having an extensive amount of unhealthy LA tissue.

Statistical Analysis

Normal continuous variables are presented as mean±standard deviation. Continuous data were analyzed by one-way ANOVA to test for significant differences. Fisher's Exact Tests were used to test for differences in categorical measurements, and differences were considered significant when $p<0.05$. Statistical analysis was performed using the SPSS 15.0 Statistical Package (SPSS Inc.; Chicago, Ill.) and Microsoft Excel 2007 (Microsoft Corporation; Redmond, Wash.).

To determine the relationship between unhealthy LA tissue, LA volume, preexisting medical history, and other demographic variables, binary logistic models were developed for three predictors of AF disease severity: baseline atrial fibrillation type, patient response to antiarrhythmic drug therapy (successful or at least one AAD failure), and patient response to ablative PVAI AF treatment (positive outcome or negative outcome). Variables of each patient's preexisting medical history included the presence/absence of a past myocardial infarction, coronary artery disease, coronary artery bypass surgery, valve surgery, history of smoking, hypertension, diabetes, or congestive heart failure. Demographic variables included age and gender. Baseline AF was entered into the predictive models for the patient's response to antiarrhythmic drug therapy and response to ablative PVAI AF treatment.

Results 81 patients underwent ablative PVAI AF treatment. 43 patients were identified as having mild amounts of unhealthy LA tissue, 30 patients were identified as having moderate amounts of unhealthy LA tissue, and 8 patients were identified as having extensive amounts of unhealthy LA tissue. Table 1 lists patient demographics for the three patient groups and overall demographics for the clinical cohort. 22 patients were placed back on antiarrhythmic medications following the ablative PVAI AF treatment, and continued therapy for a total of eight weeks following the ablative PVAI AF treatment. Initial classification based on previous HRS/ACC/AHA guidelines identified 41 patients with paroxysmal AF, 32 patients with persistent AF, and 8 patients with permanent AF (permanent AF was defined as a continuous AF episode greater than 30 days in duration or a failure of an electrical cardioversion treatment).

Among the healthy subjects, the average amount of unhealthy LA tissue was 1.7%±0.3%. In the 43 patients classified as having a mild amount of unhealthy LA tissue, the average amount of unhealthy LA tissue was 8.0%±4.2%. In the 30 patients having a moderate amount of unhealthy LA tissue, the average amount of unhealthy LA tissue was 21.3%±5.8%. In the 8 patients having an extensive amount of unhealthy LA tissue, the average amount of unhealthy LA tissue was 50.1%±15.4%. All patients having an extensive amount of unhealthy LA tissue presented with persistent AF. While all groups had similar population characteristics at baseline, a statistically significant difference in left atrial volume was noted between patients having a mild or a moderate amount of unhealthy LA tissue and patients having an extensive amount of unhealthy LA tissue (p<0.001).

Delayed Enhancement MRI and Electroanatomic Maps

Figure 1:
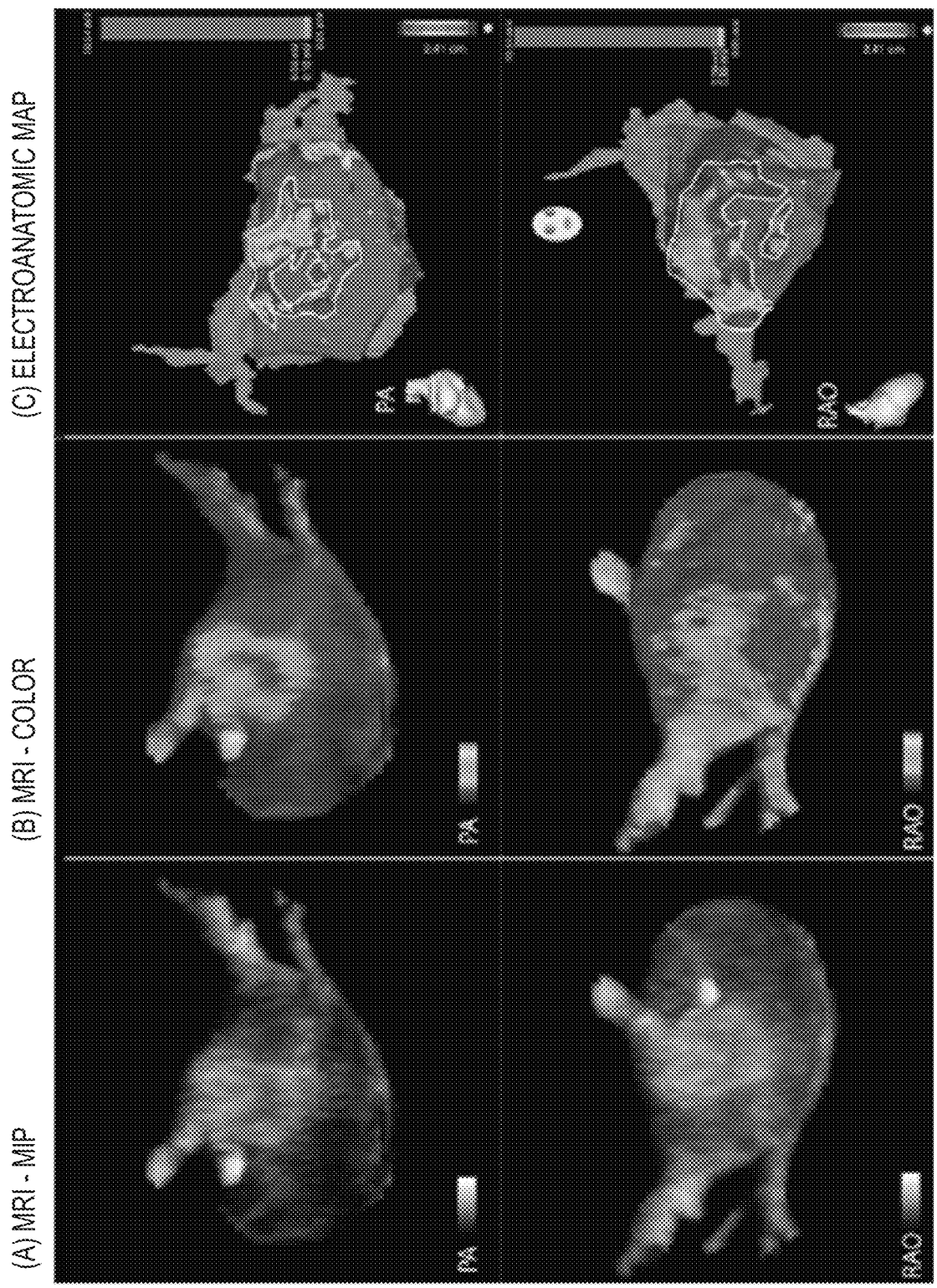
FIG. 1 shows a segmented MRI (View (A) of FIG. 1) that reveals discrete areas of elevated enhancement in the posterior wall and the septal area.

DE-MRI demonstrated detectable amounts of unhealthy LA tissue in all patients that presented for ablative PVAI AF treatment. FIG. 1 shows the segmented MRI (View (A) of FIG. 1) and the volume rendered color image (View (B) of FIG. 1) for one such patient. Discrete patches of unhealthy LA tissue (green) can be seen and identified in the posterior LA wall (PA view) and the septum (RAO view) on both the MRI color image and the EA map. In comparison, healthy subjects showed little to no unhealthy LA tissue.

Figure 2:
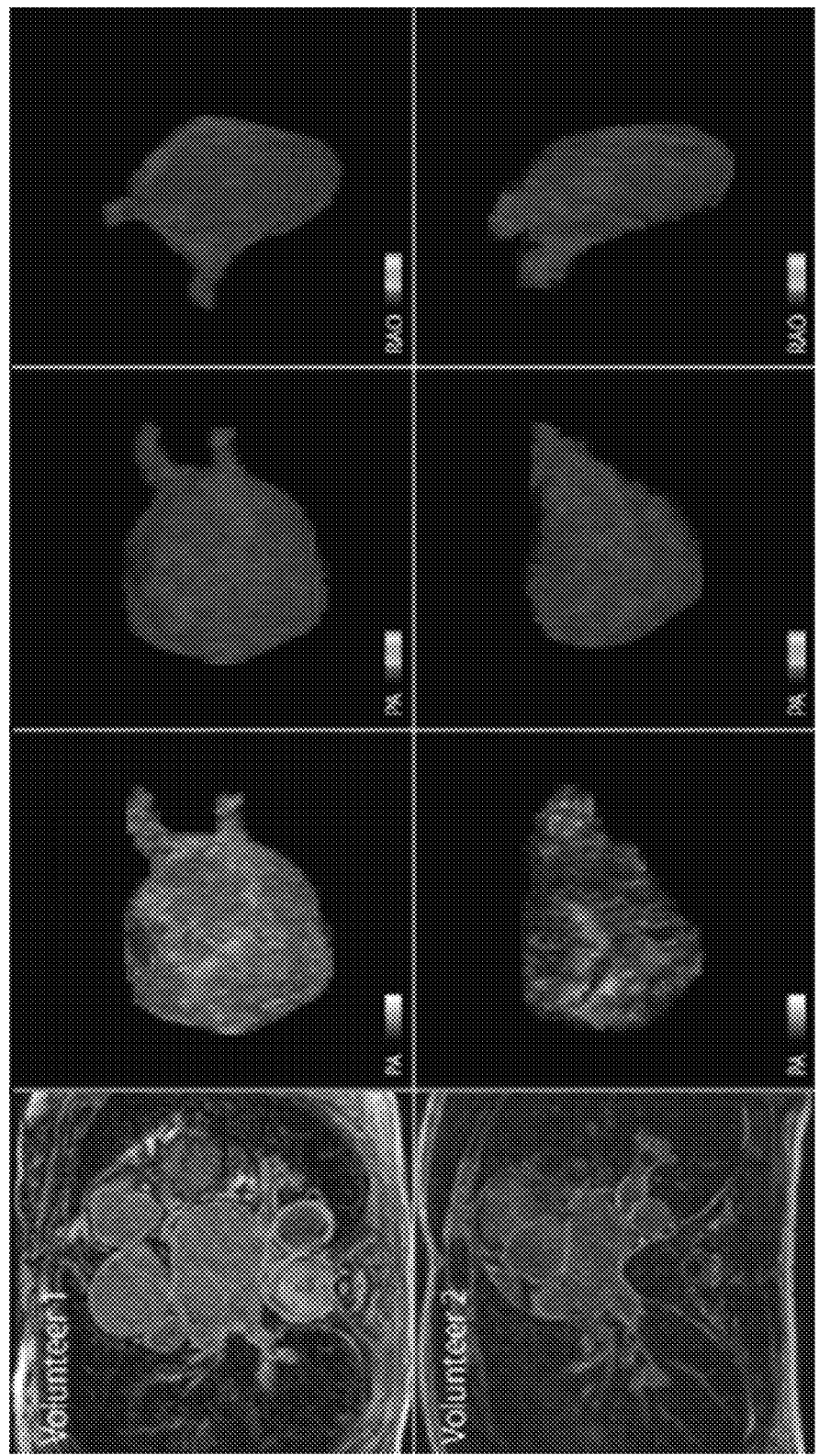
FIG. 2 shows DE-MRI models of left atrial tissues in two healthy subjects lacking structural remodeling: View (A) of FIG. 2 shows two dimensional slices from the DE-MRI scanning of the subjects; Views (B) and (C) of FIG. 2 show a posterior (PA) view of reconstructed three dimensional models from the DE-MRI scanning; and view (D) of FIG. 2 shows a right anterior oblique (RAO) view of reconstructed three dimensional models which shows the inter-atrial septum and the anterior wall.
Figure 3:
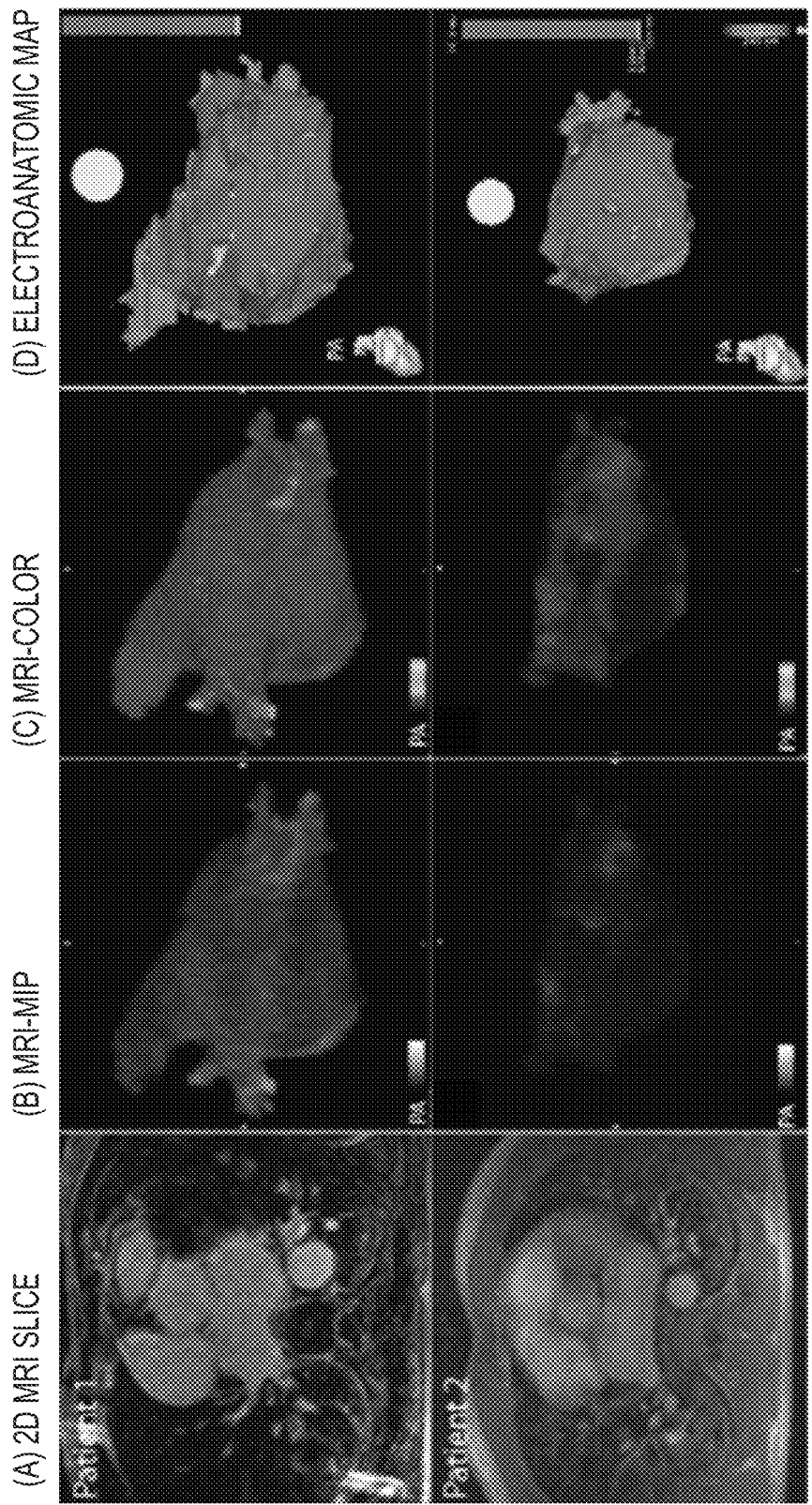
FIG. 3 shows three dimensional MRI models and electroanatomical maps of left atrial tissues in two patients having mild structural remodeling. View (A) of FIG. 3 shows two dimensional slices from the DE-MRI scanning. View (B) of FIG. 3 shows segmented DE-MRI models that reveal minimal contrast enhancement. View (C) of FIG. 3 shows color three-dimensional DE-MRI models. View (D) of FIG. 3 shows an electroanatomical map acquired during an invasive EP procedure, and shows electrically normal (purple) and abnormal (colored) left atrial tissue. Abnormally enhanced regions on MRI correlate closely with low voltage areas identified by invasive electroanatomical mapping.

FIG. 2 shows DE-MRI images for two healthy subjects that lacked the type of unhealthy LA tissue present in patients having AF. FIG. 3 shows three-dimensional DE-MRI images in patients having a mild amount of unhealthy LA tissue. Healthy subjects largely presented free of unhealthy LA tissue. The minimal contrast is suggestive of largely viable and electrically normal atrial myocardium, a finding verified using the CartoXP EA mapping system (View (D) of FIG. 3). A correlation between regions of unhealthy LA tissue having low voltage was observed in all patient DE-MRI images when compared with intracardiac voltage maps acquired with the EA mapping system (FIGS. 1 and 3-5).

Figure 4:
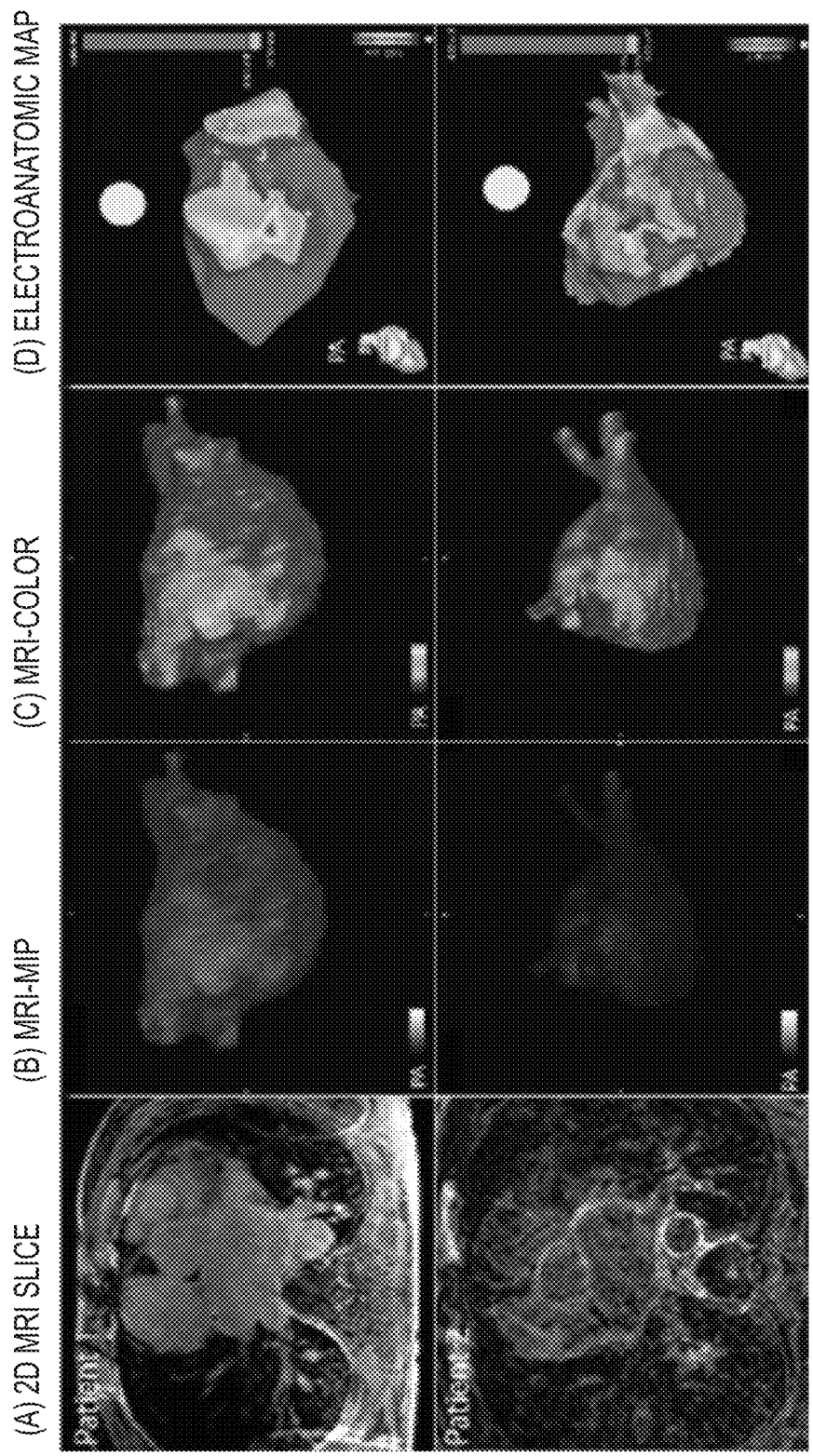
FIG. 4 shows DE-MRI models of left atrial tissues in two patients that have moderate structural remodeling in the LA wall tissue. View (A) of FIG. 4 shows a two dimensional slice from the DE-MRI scanning. View (B) of FIG. 4 shows a segmented DE-MRI model illustrating enhancement in portions of the poster LA wall. View (C) of FIG. 4 shows MRI images as color 3D models illustrating large regions of abnormal enhancement (green) in comparison to healthy tissue (blue). View (D) of FIG. 4 shows an electroanatomical map acquired during an invasive EP procedure, and shows large patches of electrically normal (purple) and abnormal tissue (colored). Electrically non-viable (scar) tissue is shown in red. The extent and location of elevated enhancement on MRI correlates closely with low voltage tissue seen on electroanatomical maps.
Figure 5:
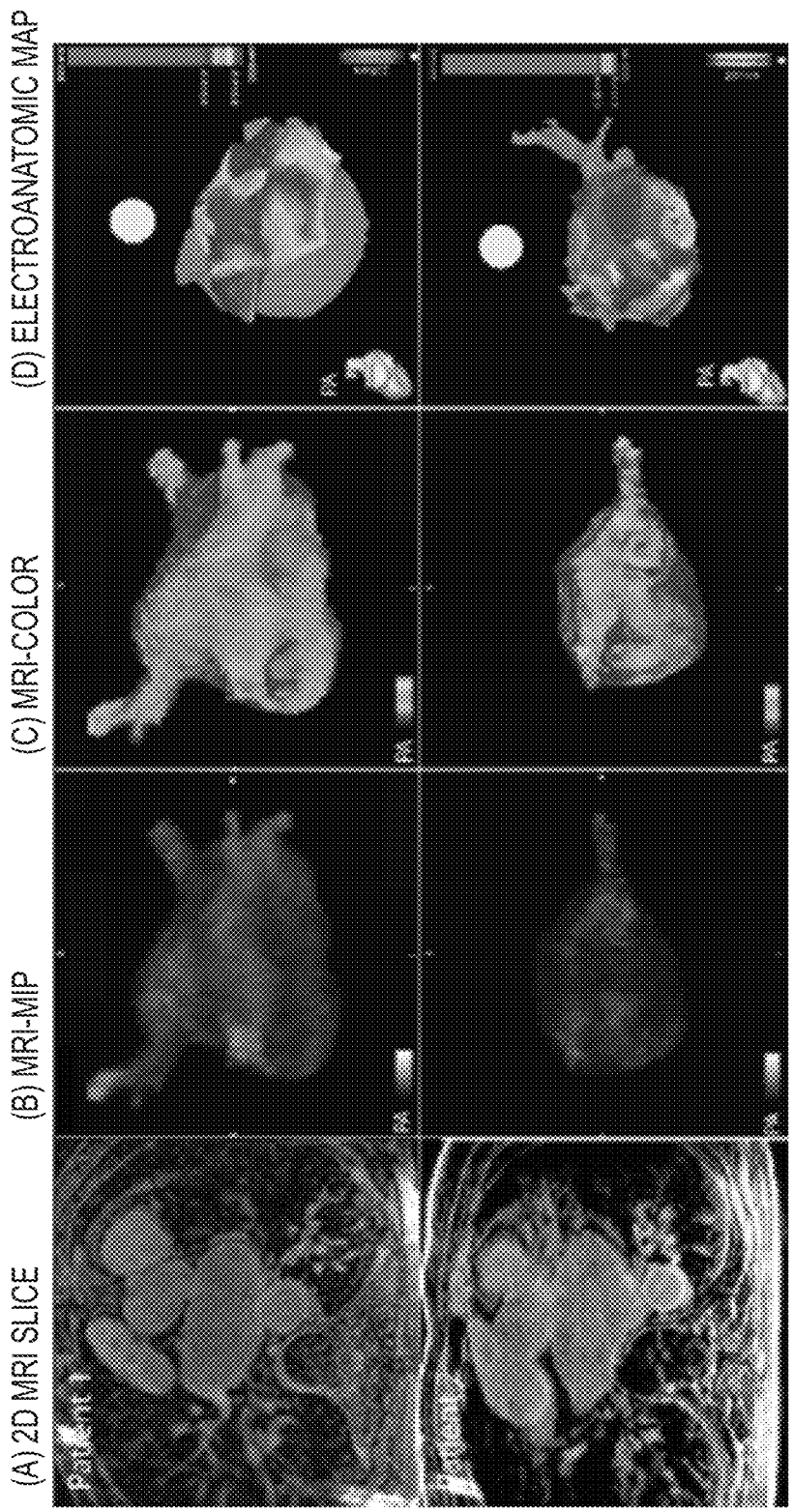
FIG. 5 shows three dimensional MRI models of left atrial tissues in two patients that have extensive structural remodeling of left atrial tissue, each of which suffered AF recurrence after PVAI. View (A) of FIG. 5 shows two dimensional slices from the DE-MIll scanning. View (B) of FIG. 5 shows segmented DE-MRI model illustrating large amounts of enhancement in various regions of the LA, including the anterior wall, posterior wall and septum. View (C) of FIG. 5 shows color three-dimensional DE-MRI models illustrating abnormally enhanced regions in green. View (D) of FIG. 5 shows electroanatomical illustrating large regions of electrically non-viable tissue (fibrotic scar) in red interspersed with electrically abnormal tissue.

In addition to the overall amount of unhealthy LA tissue, the distribution of unhealthy LA tissue differed among patients having a mild amount of unhealthy LA tissue, a moderate amount of unhealthy LA tissue, and an extensive amount of unhealthy LA tissue. Patients having mild and moderate amounts of unhealthy LA tissue, the unhealthy LA tissue was primarily localized to the LA posterior wall and interatrial septum (FIG. 3-4). Among patients having an extensive amount of unhealthy LA tissue (FIG. 5), the unhealthy LA tissue was distributed throughout all portions of the LA, including the posterior wall, inter-atrial septum, and anterior wall. This difference in distribution of unhealthy LA tissue among patients having no a moderate amount of unhealthy LA tissue and patients having an extensive amount of unhealthy LA tissue resulted in a substantial and statistically significant difference in the location of unhealthy LA tissues (p<0.001).

DE MRI Quantification and Patient Outcome

Three months after ablative PVAI AF treatment, $^{56}/_{81}$ patients (69.1%) remained free of AF recurrence while off anti-arrhythmic drugs. All 25 patients that experience AF recurrence were placed back on anti-arrhythmic drugs; and, of these patients, 21 (84%) responded favorably to antiarrhythmic drug therapy: i.e. maintained normal sinus rhythm.

Preablative PVAI AF treatment clinical classification failed to predict risk of recurrence: 12 patients (48%) were classified as having paroxysmal AF and 13 patients (52%) were classified as having persistent AF. A statistically significant difference in the amount of unhealthy LA tissue was observed in patients who experience AF recurrence following ablative PVAI AF treatment (25.9%±19.0%) in comparison to patients who did not (13.0%±9.3%, p<0.001). Six patients (14.0%) having a mild amount of unhealthy LA tissue experience AF recurrence; whereas 13 patients (43.3%) having a moderate amount of unhealthy LA tissue and six patients (75%) having an extensive amount of unhealthy LA tissue experienced AF recurrence (p<0.001). A statistically significant difference in the extent of unhealthy LA tissue, observed as enhancement in DE-MRI images, was also observed between patients who responded to medical therapy (13.3%±9.9%) versus patients who did not (21.2%±18.7%; p=0.038).

Figure 6:
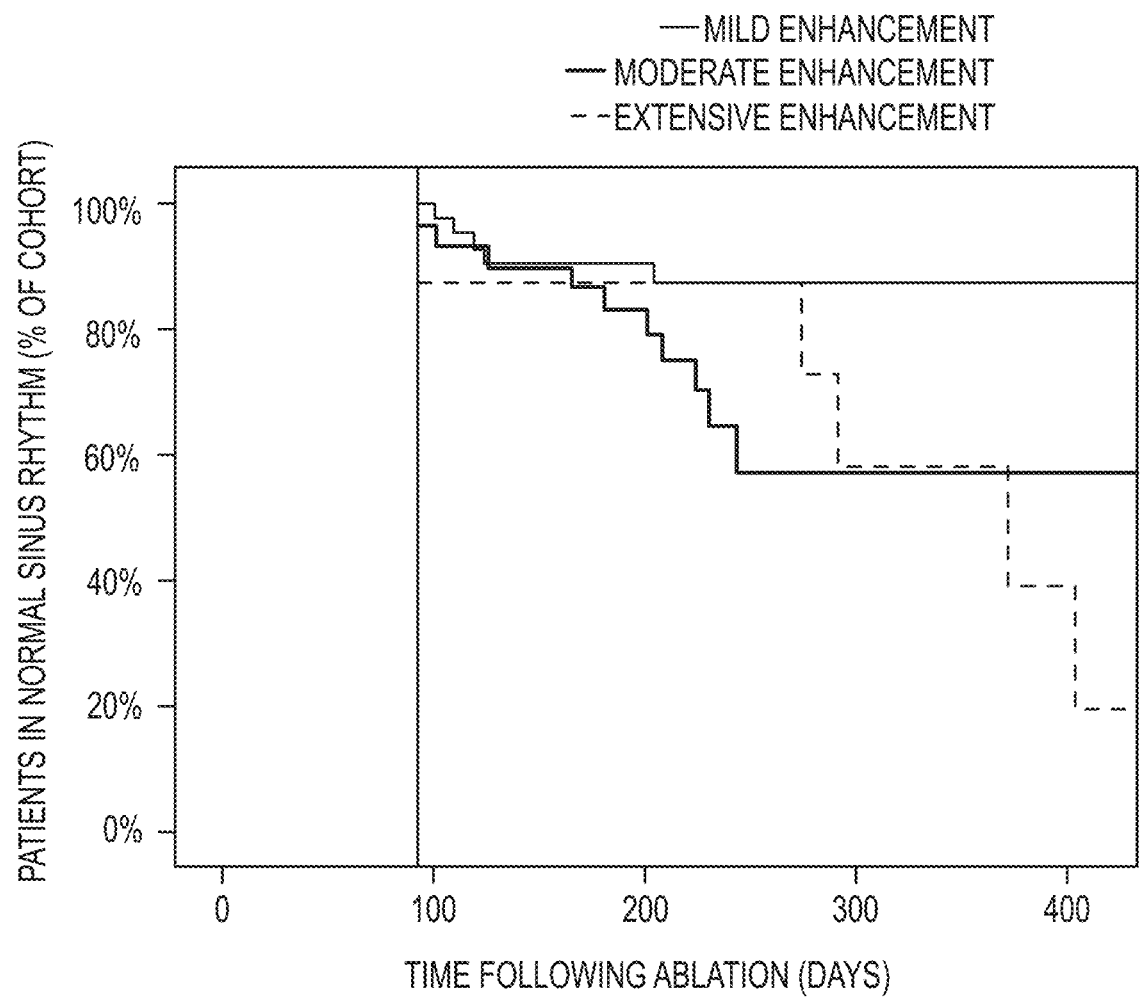
FIG. 6 shows the Kaplan-Meier analysis of patients, grouped by the extent of enhancement, in normal sinus rhythm following ablation of the left atrium.

FIG. 6 shows the Kaplan-Meier analysis of patients in normal sinus rhythm following LA ablation grouped by amount of unhealthy LA tissue. In addition to the overall differences in AF recurrence, patients having a moderate amount of a unhealthy LA tissue and an extensive amount of unhealthy LA tissue often experienced AF recurrence at later time points than patients having a mild amount of unhealthy LA tissue. Six months postablative PVAI AF treatment, no recurrences were noted in patients having a mild amount of unhealthy LA tissue.

Multivariate Model

Table 3 shows the results of the three multivariate models. Of all three outcome metrics, the amount of unhealthy LA tissue, reported as extent of LA wall enhancement, was the most statistically significant predictor. For baseline AF, both the extent of LA wall enhancement and LA volume remained as statistically significant predictors of persistent forms of the arrhythmia, though extent of LA wall enhancement had a greater adjusted odds ratio (Adj OR=4.3; 95% CI=[1.50, 12.37]) than LA volume (Adj OR=2.06, 95% CI=[1.18, 3.58]). This finding may reflect the fact that both variables likely have a degree of correlation with one another; they are both predictors of severe and persistent forms of the disease.

Extent of LA wall enhancement was the most statistically significant predictor of patient response to both drug and ablation therapies for AF. After controlling for the effect of LA wall enhancement in the drug therapy model, none of the other variables achieved statistical significance. In comparison, after controlling for the effect of LA wall enhancement in the response to ablation, smoking and a history of diabetes remained statistically significant predictors.

Example 2

Delayed Enhancement MRI Acquisition

Patients referred to the University of Utah for PVAI were included in this analysis. In all patients, a contrast enhanced 3D FLASH angiography sequence and a cine true-FISP sequence were used to define the anatomy of the LA and the pulmonary veins. To image healthy and unhealthy LA tissues, delayed enhancement MRI was acquired approximately 15 minutes after contrast agent injection using a 3D inversion recovery prepared, respiration navigated, ECG gated, gradient echo pulse sequence. Typical acquisition parameters included: free-breathing using a respiratory navigator with a 6 mm acceptance window, a transverse imaging volume with voxel size=1.25×1.25×2.5 mm (which was then reconstructed to 0.625×0.625×1.25 for analysis), TR/TE=6.3/2.3 ms, TI=230-270 ms, flip angle=22°, bandwidth=220 Hz/pixel, 1 RR interval between inversion pulses, phase encoding in right-left direction, parallel imaging using the GRAPPA technique with R=2 and 32 reference lines, partial Fourier acquisition with 0.875 factors in the phase-encoding direction and a 0.8 factors in the slice-encoding direction.

ECG gating was used to acquire a small subset of phase encoding views and during the diastolic phase of the left atrial cardiac cycle. The time interval between the R-peak of the ECG and the start of the data acquisition was defined by examining the cine images of the left atrium to determine the period of minimal left atrial motion. The typical value of the interval was 60% of the mean RR interval for patients in sinus rhythm and 50% of the mean RR for patients with non-regular heart rate. The respiratory navigator was used to acquire data during the end of the expiration phase of the respiratory cycle. To reduce the negative effect of respiration on image quality, the navigator was positioned on the right hemi-diaphragm. The acceptance window was set to ±3 mm. Typical LA motion due to respiration is predominantly in the superior/inferior (S/I) direction. This motion has lower amplitude than the corresponding diaphragm motion. Typical LA motion amplitude in the S/I direction is about two times smaller than the diaphragm S/I displacement. Thus, data acquisition for the delayed enhancement pulse sequence was active only if the LA displacement was less than 1.5 mm from the baseline. The voxel size (spatial resolution) of our pulse sequence in the S/I direction was 2.5 mm. Therefore, data was only acquired if the LA displacement in the S/I direction was less than half of the voxel size in the same direction.

To resolve the effect of the LA motion due to cardiac activity on image quality and resolution, data was acquired only during the diastolic phase of the LA. Cine images of the LA were used to identify the time interval when the LA motion was minimal. The parameters of the delayed enhancement pulse sequence were adjusted so that the data acquisition occurred during this time interval. It was further restricted to approximately 120 ms per heartbeat.

Fat saturation was used to suppress fat signal. The TE of the scan was chosen such that the signal intensity of partial volume fat tissue voxels was reduced allowing improved definition of the left atrial wall boundary. The TI value for the DE-MRI scan was identified using a scout scan. Typical scan time for the DE-MRI study was between 5 and 9 minutes depending on the patient or healthy subject respiration and heart rate.

Figure 8:
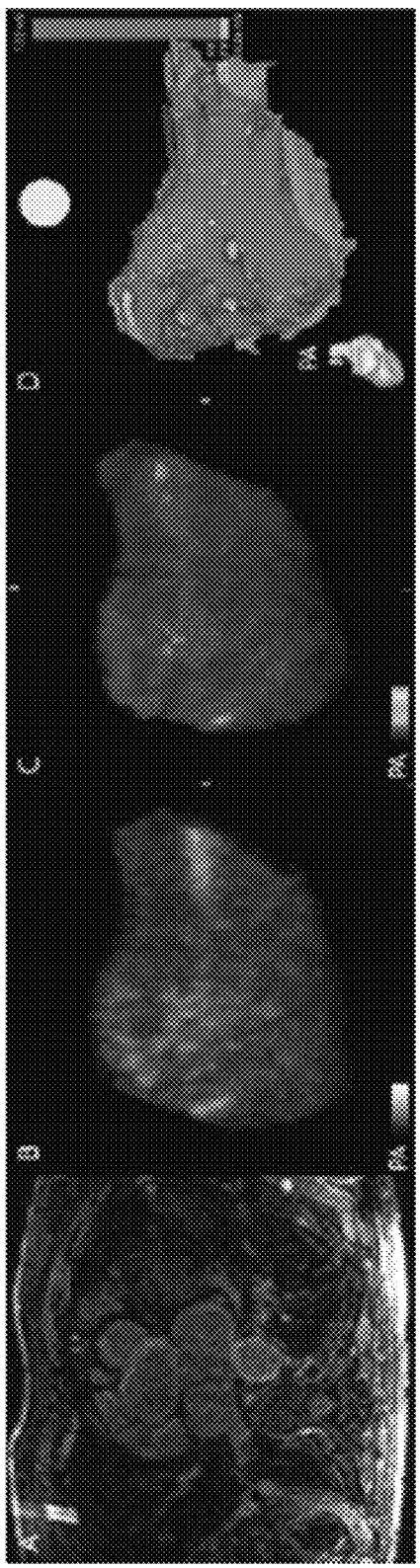
FIG. 8 shows an early DE-MRI model having a substantial artifact induced by a respiratory navigator placed on the right hemidiaphragm of the subject. View (A) of FIG. 8 shows a DE-MRI slice from the DE-MRI scanning. View (B) of FIG. 8 shows a maximum intensity projection (MIP) of a segmented DE-MRI slice. View (C) of FIG. 8 shows a three dimensional DE-MRI model. View (D) of FIG. 8 shows an electroanatomical map acquired during an invasive EP procedure. Despite the DE-MRI artifact, there is a relationship between the enhancement illustrated in the DE-MRI model (View (C) of FIG. 8) and the low voltage tissue illustrated in the electroanatomic map (View (D) of FIG. 8). The patient shown has minimal enhancement.
Figure 9:
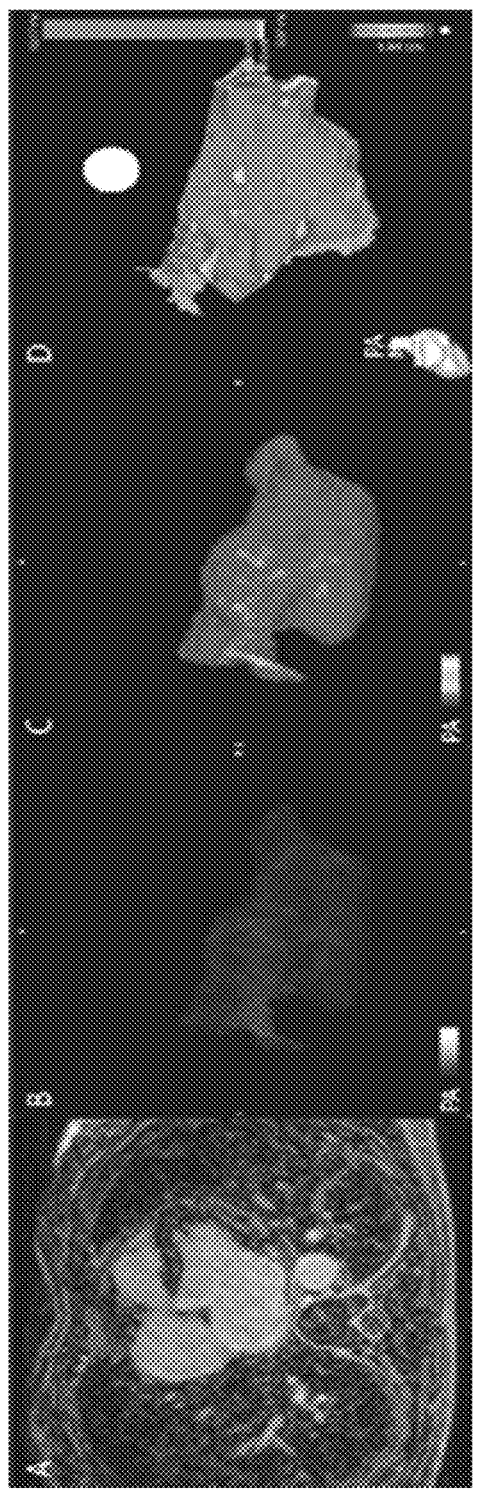
FIG. 9 illustrates a DE-MRI model that does not have a navigator induced artifact. View (A) of FIG. 9 shows a DE-MRI slice from the DE-MRI scanning. View (B) of FIG. 9 shows a maximum intensity projection (MIP) of a segmented two DE-MRI slice. View (C) of FIG. 9 shows a three-dimensional DE-MRI model. View (D) of FIG. 9 shows an electroanatomic map acquired during an invasive procedure. The patient shown has minimal enhancement.

Many of the early patient scans included some high signal artifact induced by the respiratory navigator positioned on the right hemi-diaphragm. FIG. 8 shows an example of such a scan, where it is possible to see navigator induced bright blood signal in right pulmonary veins, the most common location of the artifact. Despite the presence of navigator artifact, there is a strong qualitative relationship between the color DE-MRI image (View (C) of FIG. 8) and the EA map acquired during the catheter study (View (D) of FIG. 8). To remove the artifact, the complementary reinversion RF pulse was removed from the product implementation of the navigation scheme and navigation information was acquired following imaging data. The change preserves the inversion recovery magnetization preparation in the whole image volume and results in a more uniform blood signal in the pulmonary vein and left atrium. FIG. 9 shows an example of a later scan without the navigator artifact.

Analysis of Delayed Enhancement MRI Images

Figure 10:
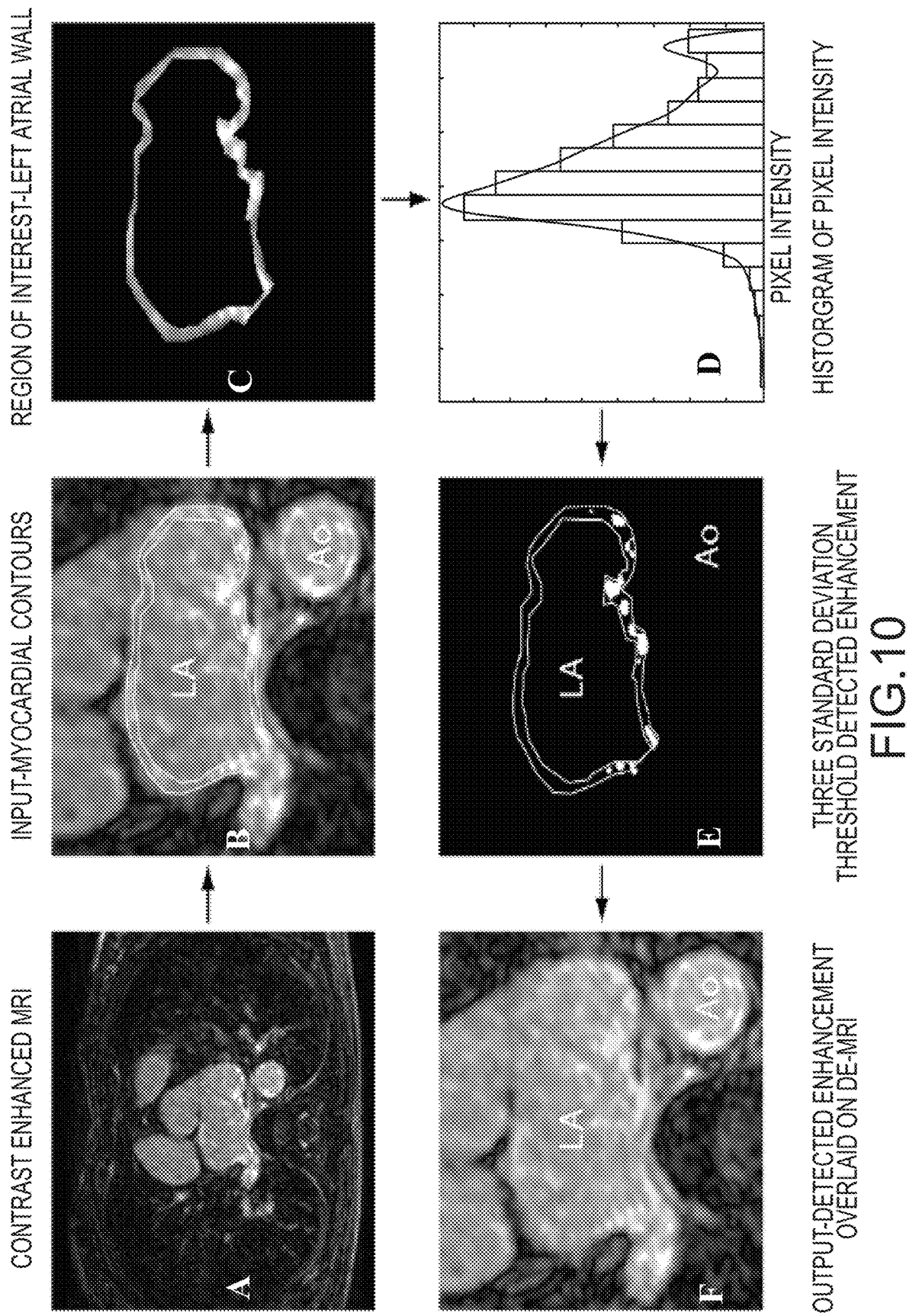
FIG. 10 illustrates data flow for a semi-automated algorithm used to detect enhancement of LA wall tissue in a DE-MRI model (Views (E) and (F) of FIG. 10). The input slices from a DE-MRI slice (View (A) of FIG. 10) were windowed (View (B) of FIG. 10) and cropped (View (C) of FIG. 10). The epicardial and endocardial borders were then manually segmented. The algorithm then automatically selected a threshold intensity for pixels likely to correspond to the enhanced/fibrotic tissue of the LA wall by determining the mean value and standard deviation of the lower region of the pixel intensity histogram (View (D) of FIG. 10). A threshold cutoff was chosen manually at two to four standard deviations above the mean for the lower histogram region.

The threshold for fibrosis identification was determined for each patient individually by using a dynamic threshold algorithm based partly on work in the left ventricle. FIG. 10 provides an overview of data processing steps of the algorithm. First, slices from DE-MRI scans are windowed and cropped. The epicardial and endocardial borders are then manually traced to isolate the LA wall. The algorithm then automatically selects a threshold intensity which is likely to correspond to the enhanced/fibrotic voxels of the left atrium by estimating the mean value and the standard deviation of the "normal" tissue. "Normal" tissue is defined as the lower region of the pixel intensity histogram between 2% and 40% of the maximum intensity within the region of interest (e.g., the LA wall). The unhealthy LA tissue (e.g., enhanced/fibrotic) signal threshold was then calculated as two to four standard deviations above the mean of "normal" signal. These values cover from 95% to 99.994% of a Gaussian distribution. The threshold was determined on a slice-by-slice basis, and the region identified as fibrotic was then compared to the original DE-MRI slice for appropriateness. The most commonly used cutoff was three standard deviations.

The overall volume of the LA myocardium was calculated as the number of voxels within the endocardial and epicardial contours. The extent of enhancement was then calculated as the number of pixels identified as enhanced by the semi-automated algorithm over the volume of LA myocardium for the slice.

Inter-Observer Agreement

For interobserver agreement, observers 1 and 2 each analyzed a subset of 43 patients from the clinical cohort with high quality DE-MRI scans. Each observer was blinded to the results obtained by the other observer, and each observer independently analyzed the scans by following a set protocol. First, the endocardial contour was traced, avoiding the pulmonary veins. Second, the epicardial contour was traced.

The data was then quantified using the semi-automated algorithm by a third individual according to the described methodology.

Figure 11:
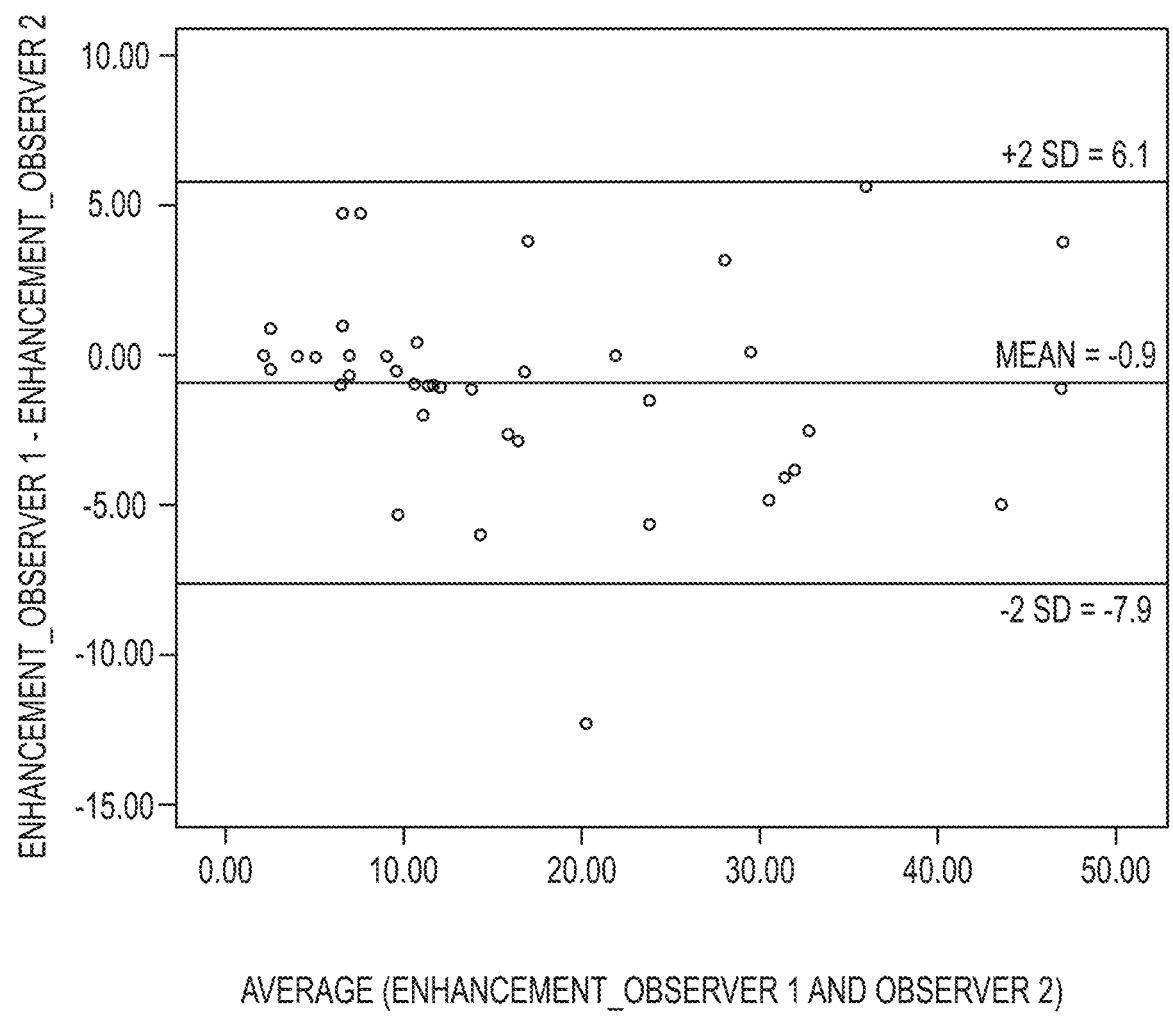
FIG. 11 provides a Bland-Altman plot of inter-observer agreement of detected LA wall enhancement in 43 patients.

The limits of agreement were calculated by Bland-Altman analysis. The difference between the amount of unhealthy LA tissues, observed as enhancement, detected from the segmentation of observer 1 and observer 2 was taken and plotted against the average amount of unhealthy LA tissue detected from the segmentations of observers 1 and 2. The average difference and 95% confidence interval (limits of agreement [LOA]) were calculated from these plots. FIG. 11 shows the Bland-Altman plot for the interobserver agreement of amounts of unhealthy LA wall tissue detected in 43 patients. The average difference was −0.9% (LOA=−7.9% to 6.1%).

Intra-Observer Agreement

Figure 12:
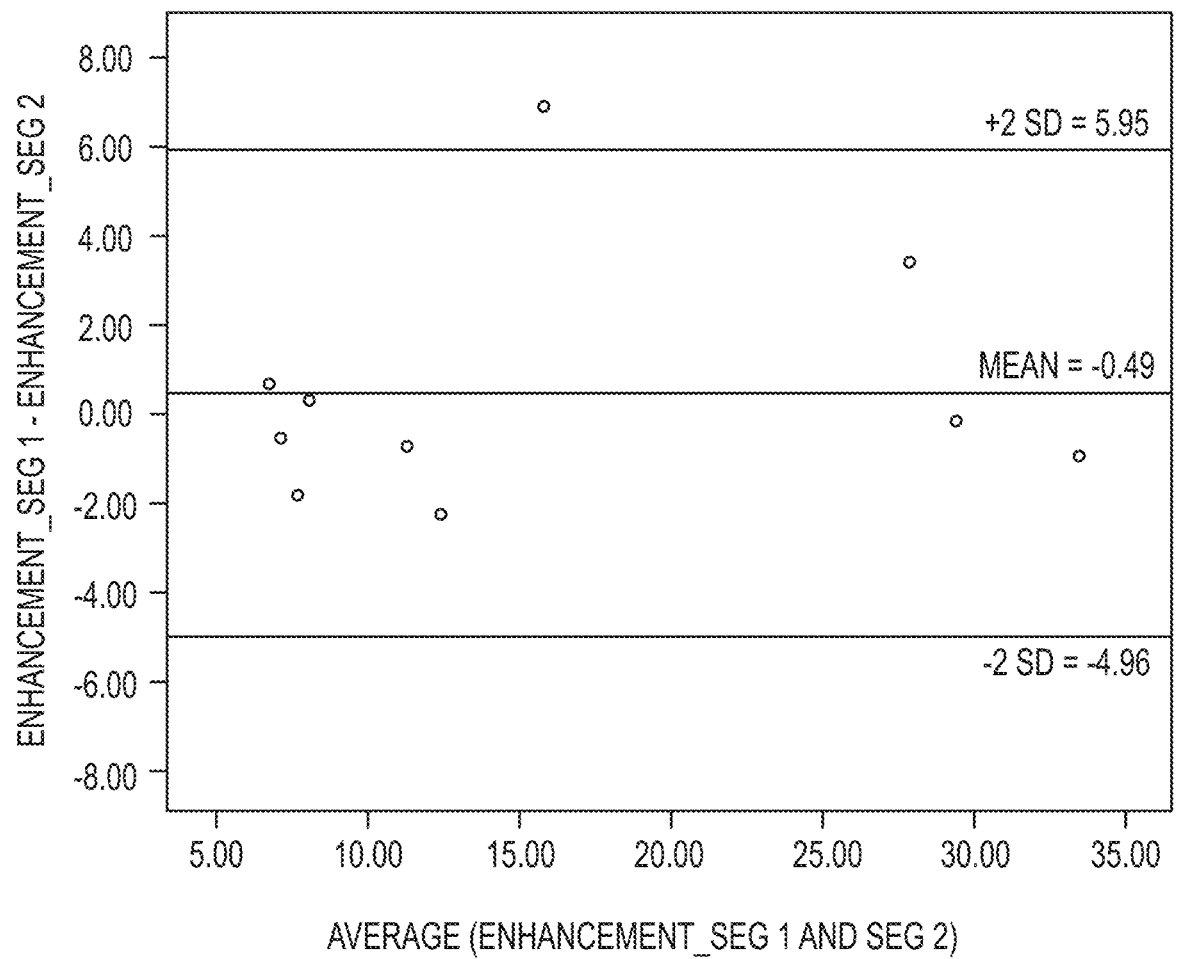
FIG. 12 provides a Bland-Altman plot of inter-observer variability of fibrosis detection and LA volume segmentation in 10 patients.

The intraobserver agreement was calculated from a set of 10 patients which were segmented two times by the same observer. The average difference and LOA were calculated in a manner similar to that described for the interobserver agreement. The difference between segmentation 1 and segmentation 2 from the same observer was determined and plotted against the average detected enhancement. FIG. 12 shows the Bland-Altman plot for the intra-observer agreement of detected LA wall enhancement in the 10 Patients. The average difference was 0.49% (LOA=−4.96% to 5.95%).

Relationship Between EA Maps and MRI Volume Models

Qualitative Assessment

Figure 13:
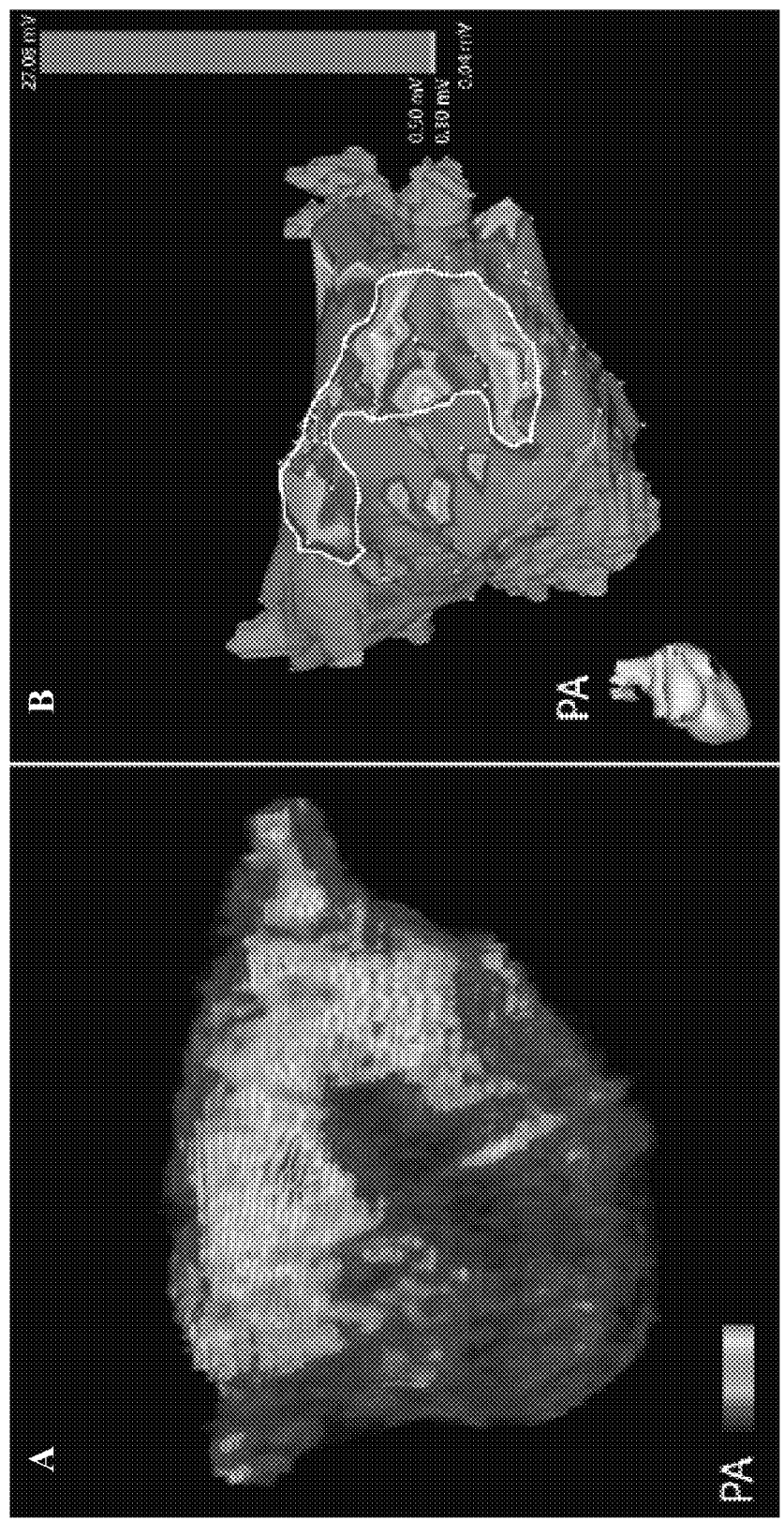
FIG. 13 illustrates a two-dimensional DE-MRI slice from DE-MRI scanning of the LA wall tissue of a patient (View (A) of FIG. 13) and an electroanatomical map of the LA wall tissue of the patient (View (B) of FIG. 13). In the two-dimensional DE-MRI slice of View (A) of FIG. 13, there is no visible navigator artifact on the right side. A strong coincidence of localization exists between the enhanced tissue in the DE-MRI image and the low voltage tissue in the electroanatomical map.

A trained expert qualitatively assessed and graded the relationship between EA maps and MRI color models. The relationship was rated on a 0 to 4 scale where 0 was coded as "No Relationship," 1 was coded as "Poor", 2 was graded as "Mediocre", 3 as "Good", and 4 as "Excellent." The average relationship between EA maps and MRI images was 3.65±0.55 (range 2 to 4). FIG. 13 shows an example of a strong qualitative MRI correlation with the corresponding EA map. The region of low voltage tissue has been highlighted in white on the electroanatomic map.

Figure 14:
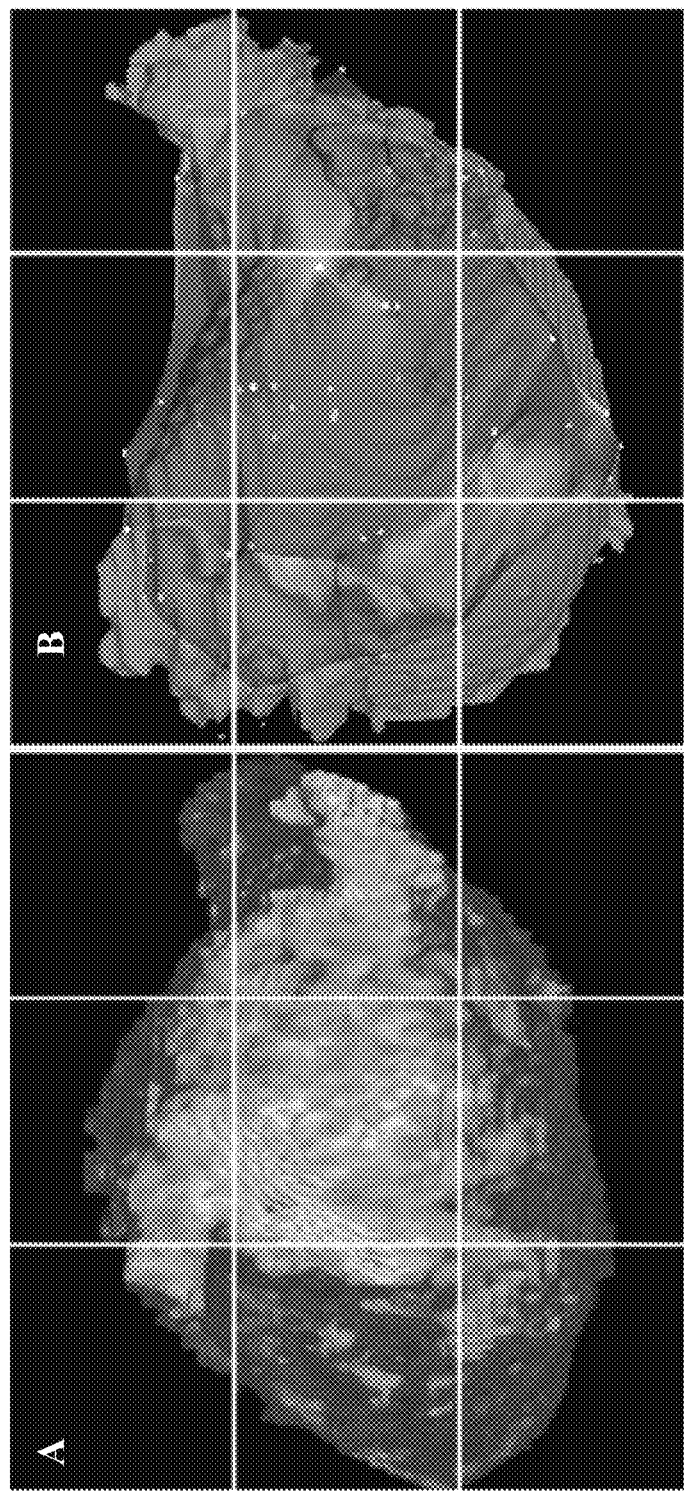
FIG. 14 illustrates a posterior wall projection of a DE-MRI volume model (View (A) of FIG. 14) and an electroanatomical map (View (B) of FIG. 14) acquired with a CARTO system.

Quantitative Assessment 54 patients with high quality CartoXP maps (defined as greater than 100 voltage points evenly spread throughout the atrium) were selected and scored by blinded reviewers. The same was done using three dimensionally rendered DE-MRI images. The LA was then Subdivided into 18 Specific Regions (9 on the Posterior Wall and 9 on the Anterior and septal wall). FIG. 14 shows the posterior wall projections of a DE-MRI image and EA map for the same patient. In both images, the 9 box grid used for scoring has been applied.

Figure 15:
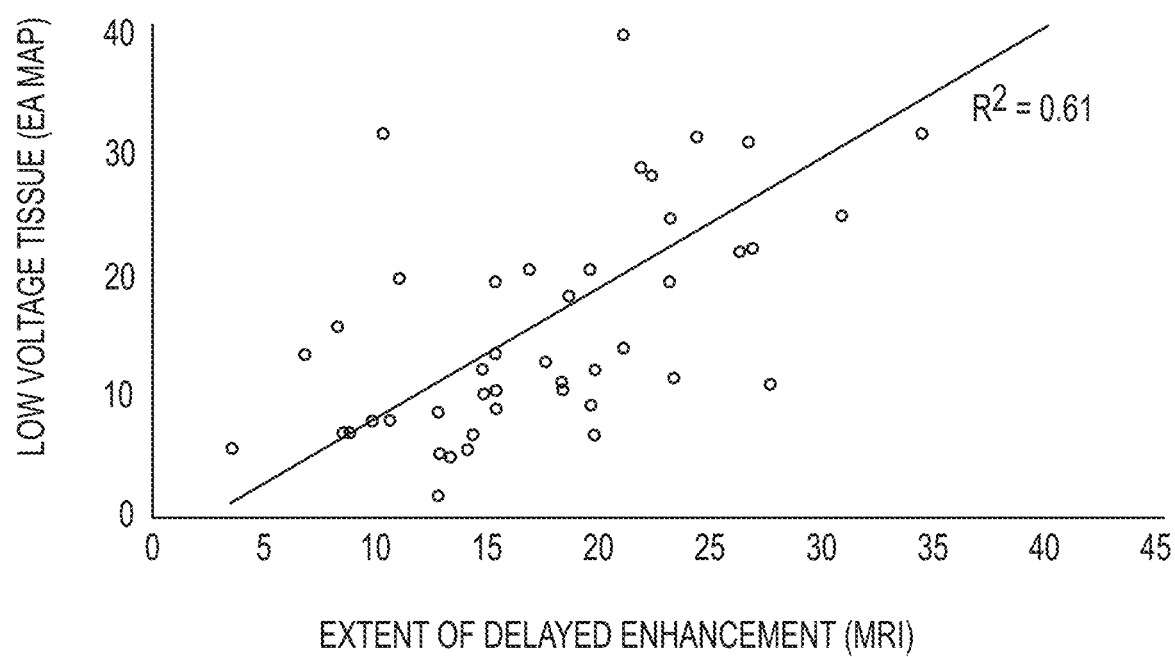
FIG. 15 provides a pairwise analysis for the enhanced DE-MRI LA tissue and the electroanatomical map of low voltage LA tissue of FIG. 14. A positive correlation of $R^2=0.61$ was noted.

Four blinded reviewers (two individuals experienced in cardiac MRI and two individuals experienced in ablative PVAI AF treatment) separately scored the DE-MRI models and EA maps. Two views, the posterior (PA) and right anterior oblique (RAO) which shows the anterior wall and septum, were chosen for scoring. The images were scored on a 0 to 3 scale. For MRI images, 0 was scored as no enhancement, 1 as mild enhancement, 2 as moderate, and 3 as extensive enhancement. For EA maps, 0 was considered healthy tissue (voltage>1 mV, purple on EA maps), 1 was considered as mild illness (some abnormal tissue where voltage was >0.1 mV and <0.5 mV), 2 as moderate illness (presence of low voltage tissue [voltage>0.1 mV and <0.5 mV] as well as fibrotic scar [voltage<0.1 mV]), and 3 as scar (voltage<0.1 mV, red on EA maps). The overall score was a sum of all nine regions for both the posterior wall and the septum. The reviewer scores were then averaged to determine the score used in quantitative analysis. The relationship between EA maps and MRI images was then analyzed using pairwise regression. FIG. 15 shows the analysis between the extent of enhancement on MRI and the amount of low voltage tissue. A positive correlation of $R^2=0.61$ was determined.

TABLE 1

Patient Population Characteristics

|  | Total | Mild Enhancement (n = 43) | Moderate Enhancement (n = 30) | Extensive Enhancement (n = 8) | P-Value * |
| --- | --- | --- | --- | --- | --- |
| Age (years) | 63.6 ± 12.0 | 63.3 ± 12.3 | 62.2 ± 12.5 | 70.1 ± 6.0 | 0.25 |
| Left Ventricle Ejection Fraction | 52.3 ± 9.8 | 53.3 ± 10.3 | 52.4 ± 8.8 | 46.4 ± 9.0 | 0.23 |
| Left Atrium Volume - Pre-procedure (cm$^3$) | 94.3 ± 41.3 | 83.7 ± 29.4 | 98.5 ± 48.3 | 142.1 ± 36.9 | <0.001 |
| Gender |  |  |  |  |  |
| Female | 29 (35.8%) | 13 (30.2%) | 12 (40.0%) | 4 (50.0%) | 0.49 |
| Male | 52 (64.2%) | 30 (69.8%) | 18 (60.0%) | 4 (50.0%) |  |
| Hypertension | 42 (51.9%) | 25 (58.1%) | 13 (43.3%) | 4 (50.0%) | 0.49 |
| Diabetes | 10 (12.3%) | 4 (9.3%) | 4 (13.3%) | 2 (25.0%) | 0.36 |
| Coronary Artery Disease | 9 (11.1%) | 5 (11.6%) | 3 (10.0%) | 1 (12.5%) | 1.00 |
| History of Smoking | 9 (11.1%) | 6 (14.0%) | 1 (3.3%) | 2 (25.0%) | 0.16 |
| Valve Surgery | 3 (3.7%) | — | 1 (3.3%) | 2 (25.0%) | 0.01 |
| Myocardial Infarct | 2 (2.5%) | 2 (4.7%) | — | — | 0.60 |
| Medications at the Time of Ablation ** |  |  |  |  |  |
| Antiarryhtmic Medications | 22 (27.2%) | 9 (20.9%) | 11 (36.6%) | 2 (25.0%) | 0.15 |
| Amiodarone | 15 (18.5%) | 8 (18.6%) | 4 (13.3%) | 3 (37.5%) | 0.31 |
| Digoxin | 12 (14.8%) | 6 (14.0%) | 5 (16.7%) | 1 (12.5%) | 0.90 |
| Beta Blockers | 42 (%) | 23 (53.4%) | 15 (50.0%) | 4 (50.0%) | 0.87 |
| Calcium Channel Blockers | 10 (12.3%) | 5 (11.6%) | 3 (10.0%) | 2 (25.0%) | 0.52 |
| Response to Antiarrhythmic Medications |  |  |  |  |  |
| Failed One or More Medications | 32 (39.5%) | 14 (32.6%) | 12 (40.0%) | 6 (75.0%) | 0.080 |

\* Continuous measurements are presented as mean ± standard deviation. Categorical measurements are presented as number positive for the condition and percentage of the total. Significance tests for demographic characteristics used One-Way ANOVA to detect statistically significant differences across continuous measurements. Fisher exact tests were used for categorical measurements.
\*\* Many patients were on multiple medications prior to ablative treatment. The reported numbers and percentages add to more than 100%. Patients being treated on Amiodarone had it discontinued at least one month prior to the ablation procedure.

TABLE 2

Results of DE-MRI Analysis and Patient Outcome

| | Total | Mild Enhancement (n = 43) | Moderate Enhancement (n = 30) | Extensive Enhancement (n = 8) | P-Value * |
|---|---|---|---|---|---|
| Extent of Structural Remodeling (% of LA Volume) | 17.1 ± 14.2 | 8.0 ± 4.3 | 21.3 ± 5.8 | 50.1 ± 15.4 | — |
| Location of Enhancement (>50% of Surface Enhanced) | | | | | |
| LA Posterior Wall | 51 (63.0%) | 18 (41.9%) | 25 (83.3%) | 8 (100.0%) | <0.001 |
| LA Anterior Wall | 13 (16.0%) | 3 (7.0%) | 2 (6.7%) | 8 (100.0%) | <0.001 |
| Atrial Septum | 24 (29.6%) | 7 (16.3%) | 9 (30.0%) | 8 (100.0%) | <0.001 |
| Type of Atrial Fibrillation - Baseline | | | | | |
| Paroxysmal | 41 (50.6%) | 28 (65.1%) | 13 (43.3%) | — | <0.001 |
| Persistent | 40 (49.4%) | 15 (25.6%) | 17 (56.7%) | 8 (100%) | |
| Recurrence | 25 (30.9%) | 6 (14.0%) | 13 (43.3%) | 6 (75.0%) | <0.001 |

TABLE 3

Results of Multivariate Analysis

| | Baseline AF Type* | | | Response to Antiarrhythmia Drug Therapy | | | Successful AF Ablation | | |
|---|---|---|---|---|---|---|---|---|---|
| Predictors | P-value | Adjusted Odds Ratio | 95% CI [OR] | P-Value | Adjusted Odds Ratio | 95% CI [OR] | P-Value | Adjusted Odds Ratio | 95% CI [OR] |
| Extent of LA Wall Enhancement ** | 0.007 | 4.3 | [1.50, 12.37] | 0.01 | 3.73 | [1.37, 10.13] | 0.001 | 17.8 | [3.40, 94.20] |
| LA Volume † | 0.011 | 2.06 | [1.18, 3.58] | 0.542 | 0.82 | [0.44, 1.54] | 0.093 | 1.7 | [0.91, 3.30] |
| Baseline Atrial Florilation Type †† | — | — | — | 0.8 | 0.85 | [0.24, 2.98] | 0.707 | 0.721 | [0.13, 3.97] |
| Age | 0.972 | 1.0 | [0.95, 1.05] | 0.988 | 1.00 | [0.96, 1.05] | 0.408 | 1.028 | [0.96, 1.10] |
| Myocandial infarction | 0.589 | 0.31 | [0.01, 20.82] | 0.943 | 1.18 | [0.13, 103.1] | 0.999 | — | — |
| Coronary Artery Disease | 0.537 | 2.22 | [0.18, 27.84] | 0.42 | 0.33 | [0.02, 4.95] | 0.851 | 0.585 | [0.001, 234.80] |
| Coronary Artery Bypass Surgery | 0.62 | 2.78 | [0.05, 158.45] | 0.309 | 6.18 | [0.19, 206.9] | 0.999 | — | — |
| Valve Surgery | 0.999 | — | — | 0.288 | 0.13 | [0.003, 5.59] | 0.999 | — | — |
| History of Smoking | 0.298 | 0.33 | [0.04, 2.68] | 0.694 | 1.43 | [0.24, 8.52] | 0.015 | 32.9 | [2.0, 553.60] |
| Hypertension | 0.376 | 1.75 | [0.51, 0.03] | 0.719 | 1.27 | [0.35, 4.56] | 0.8 | 1.242 | [0.23, 6.60] |
| Diabetes | 0.687 | 0.67 | [0.10, 4.63] | 0.94 | 1.07 | [0.20, 5.84] | 0.05 | 0.033 | [0.001, 1.0] |
| Congestive Heart Failure | 0.253 | 5.00 | [0.32, 79.01] | 0.533 | 2.88 | [0.14, 80.0] | 0.149 | 8.756 | [0.46, 166.5] |

*The baseline AF type was calculated considered as paroxysmal or persistent AF
** The extent of enhancement was entered into analysis as a categorical variable. Patients with mild enhancement showed abnormal enhancement in less than 15% of the LA wall. Moderate enhancement was considered to be between 15% and 25% abnormal enhancement. Extensive enhancement was considered to be greater than 35% LA wall enhancement.
† LA volume was entered into the predictive model as a categorical variable. Patients were divided into four separate groups by the quartiles. Quartile 1 included patients with LA volume < 59.87 mL, quartile 2 was from 59.9 to 86.9 mL, quartile 3 included patients from 85.91 to 115.12 mL, and quartile 4 included patients with LA volume > 116.13 mL.
†† The baseline atrial florilation type (Paroxysmal/Persistent) was only included in predictive models for response to ablation and medical therapy.

Example 3

Patients

After informed consent was obtained from 53 patients, each underwent, prior to receiving ablative PVAI AF treatment, MRI scanning to determine pulmonary vein location, esophagus location, LA anatomy, and health of LA wall tissues. MRI scanning of all patients was repeated 3 months after the ablative PVAI AF treatment to determine the outcome of the treatment. Following treatment, the patients continued warfarin anticoagulation therapy to maintain an international normalized ratio of 2.0 to 3.0 for a minimum of 3 months. Positive treatment outcome was defined as lack of AF recurrence while off antiarrhythmic medications. Negative treatment outcome was defined as AF recurrence, and AF recurrence was defined as a detected symptomatic or asymptomatic AF Episode lasting >15 seconds.

AF event monitors were in place for a minimum of two months following ablative PVAI AF treatment, and patients were instructed to activate the monitors any time they felt AF symptomatic. To determine the presence or absence of asymptomatic AF, all patients received a 48 hour Holter ECG recording three months after receiving ablative PVAI AF treatment. AF recurrence was therefore determined from patient reporting, event monitoring, Holter monitoring, and ECG data.

53 patients underwent ablative PVAI AF treatment. Seven of the 53 patients were excluded from statistical data analysis because of inadequate MR images. The excluded patients included six with poor image quality on the preablative or postablative PVAI AF treatment DE-MRI scans and one who received an insufficient dose of intravenous contrast agent. Poor image quality typically resulted from patient motion during DE-MRI scanning and/or significant cardiac arrhythmia. In one case, navigator signal interference precluded accurate analysis. Results from the remaining 46 patients were included in the analyzed data. Table 4 shows patient demographics for patients having positive and negative outcomes in response to ablative PVAI AF treatment. Statistically significant differences were seen among the patient populations for age, left ventricle ejection fraction, LA area, and LA volume.

Pulmonary Vein Isolation Procedure

The ablative PVAI AF treatment was performed under intracardiac echocardiogram guidance. A 10-F, 64-element, phased-array ultrasound catheter (AcuNav, Siemens, Mountain View, Calif.) was used to visualize the interatrial septum and to guide transseptal puncture. A circular mapping catheter (Lasso, BioSense Webster, Diamond Bar, Colo.) and an ablation catheter were inserted into the LA. An intracardiac echocardiogram was used to identify PV ostia and their antra, and to help position the circular mapping catheter and ablation catheter at the desired sites. Temperature and power were set to 50° C. and 50 W (pump flow rate at 30 ml/min), respectively. RF delivery was interrupted in the event of an increase in impedance or an increase in microbubble density during ablation. All patients underwent ablative PVAI AF treatment and LA posterior wall and septal debulking.

Delayed Enhancement MRI Acquisition Sequences 24 to 72 hours prior to receiving ablative PVAI AF treatment, all patients underwent DE-MRI scanning on a 1.5-T Avanto clinical scanner (Siemens Medical Solutions, Erlangen, Germany) using a phased-array receiver coil. The MRI protocol included sequences designed to identify LA and PV anatomy. The anatomy was evaluated using a contrast enhanced three-dimensional fast low angle shot (FLASH) sequence and cine true-fast imaging with a steady state precession sequence. Typical acquisition parameters for 3D FLASH scans were: breath-hold in expiration, a transverse (axial) imaging volume with voxel size=1.25× 1.25×2.5 mm, repetition time (TR)=3.1 ms, echo time (TE)= 1.0 ms, and parallel imaging using a generalized autocalibrating partially parallel acquisition (GRAPPA) technique with reduction factor R=2 and 32 reference lines, scan time=14 s. The 3D FLASH scan was acquired twice: precontrast and during a first pass of contrast agent comprising intravenous injection of a dose of 0.1 mmol/kg body weight, 2 ml/s injection rate, followed by a 15-ml saline flush. Timing of the first pass scan was defined using a MRI fluoroscopic scan.

Complete MRI scan coverage of the LA was achieved with 16 to 22 transverse 2-dimensional slices acquired during retrospective ECG gated, cine pulse sequencing. All images were acquired during breath-hold in expiration (1 or 2 slices per breath-hold, depending on patient heart rate and tolerance to breath-holding), and the obtained images were used to evaluate LA morphology during the cardiac cycle. Typical scan parameters included: 6 mm slice thickness, no gap between slices, pixel size=2.0×2.0 mm, TR/TE=2.56/ 1.03 ms, GRAPPA with R=2 and 44 reference lines, 15 views/segment.

DE-MRI scans were acquired 15 min after contrast agent injection using a 3D inversion recovery prepared, respiration-navigated, ECG gated, gradient echo pulse sequence. Typical acquisition parameters included: free breathing using navigator gating, a transverse imaging volume with voxel size=1.25×1.25×2.5 mm (reconstructed to 0.625× 0.625×1.25 mm), TR/TE=6.3/2.3 ms, inversion time (TI) =230 to 270 ms, and GRAPPA with R=2 and 32 reference lines. ECG gating was used to acquire a small subset of phase encoding views used during diastolic phase of the LA cardiac cycle. A time interval between the R-peak of the ECG and the start of DE-MRI scan data acquisition was defined using the cine images of the LA. Fat saturation was used to suppress fat signal. The TE of the scan (2.3 ms) was chosen so that fat and water were out of phase and the signal intensity of partial volume fat-tissue voxels were reduced, which provided improved delineation of the LA wall boundary. A TI value for DE-MRI scans was identified using a scout scan. Typical scan time for the DE-MRI study was 5 to 10 min, depending on subject respiration and heart rate. If the first DE-MRI scan acquisition did not have an optimal TI or had substantial motion artifacts, the scan was repeated.

Image Processing and Analysis

All MR images were evaluated and interpreted by two independent operators. Processing of DE-MRI digital imaging and communications in medicine (DICOM) formatted data sets was performed using OsiriX (open-source) for visualization, whereas quantification of images was performed using Matlab (Mathworks, Inc., Natick, Mass.). Data from three-dimensional DE-MRI scanning of LA tissue were evaluated slice by slice, using volume rendering tools. These images were segmented and rendered, which allowed for unique visualization of ablated LA tissue patterns resulting from ablative PVAI AF treatment using the entire data set and facilitated correlation with 3D CARTO images. Visualization was performed using smooth table opacity.

The extent of ablated (e.g., scarred) LA tissue resulting from ablative PVAI AF treatment was measured in patients using a threshold based ablation detection algorithm. In all DE-MRI model, the epicardial and endocardial borders were manually contoured using custom image display and analysis software written in MATLAB. Care was taken, in two-dimensional tracings of the endocardial and epicardial walls, to confine the imaged region of interest to LA wall tissues and to avoid the blood pool, particularly on the right side, where a navigator-induced artifact was present in some patient scans.

Healthy and unhealthy LA tissues were identified based on a bimodal distribution of pixel intensities of LA tissue image data. The first mode of lower pixel intensities identified healthy tissue. Unhealthy tissue was identified at 3 standard deviations above the normal tissue mean pixel intensity. Regions identified as ablated tissue were visualized independently to ensure accuracy of ablation induced lesion detection. Ablated LA tissue area for each slice was summed for the entire scan, and reported as a ratio of ablated tissue volume to total LA tissue volume. For selected patients with characteristic patterns of ablated LA tissue observed in the OsiriX 3D visualizations, image masks of ablated regions of LA tissue were reconstructed into three-dimensional volumes for comparison with the OsiriX visualizations. Operators were blinded during the analysis of all imaging and electrophysiology data.

Statistical Methods

Normal continuous variables are presented as mean SD. Continuous data were analyzed by the Student t test to test for significant differences. Chisquare tests were used to test for differences in categorical measurements. Differences were considered significant at $p<0.05$. Statistical analysis was performed using the SPSS 15.0 statistical package (SPSS Inc., Chicago, Ill.).

DE MRI Visualization and Quantification

Hyperenhancement indicative of ablated tissue resulting from ablative PVAI AF treatment in DE-MRI images of the LA was not seen in patients prior to ablative PVAI AF treatment. Mild enhancement indicative of unhealthy LA tissue was seen in 4 patient DE-MRI scan images prior to ablative PVAI AF treatment (8.7%); however, it was clearly lower intensity than DE-MRI scans images following ablative PVAI AF treatment. In addition, such pre-treatment enhancement in LA tissues did not meet the threshold for hyperenhancement determined by our quantification algorithm. Clear contrast enhancement was seen, for all 46 patients, in DE-MRI images following ablative PVAI AF treatment, most commonly in the posterior LA wall, interatrial septum, and areas surrounding the PVs (FIG. 16).

Two experienced, independent operators evaluated the presence or absence of contrast enhancement on DE-MRI with agreement in all cases. Artificial signal enhancement in DE-MRI scan images occurred within the right PVs for some patients, likely as a result of the navigator RF pulse located over the right hemidiaphragm, and did not reflect unhealthy or ablated LA tissue. This navigator-induced artifact was identifiable by its location and intensity. Modifications of the pulse sequence resulted in a complete removal of navigator interference (data not shown).

FIG. 16 shows MRI slices for 4 separate patients prior to and three months following ablative PVAI AF treatment. Ablative injury to the LA wall resulting from ablative PVAI AF treatment is largely localized to the posterior LA wall, PV ostia, and interatrial septum, but the degree of injury varied among patients. The anterior LA wall was consistently spared and free of ablated tissue in all patients, which is consistent with current strategies for ablative PVAI AF treatments. FIG. 16 also shows exemplary 3D visualization of the LA wall of a patient before and after ablative PVAI AF treatment in four different views: posterior, right, left, and superior.

FIG. 17 shows ablated LA tissue detection using a semi-automated computer algorithm. When ablated tissue, as identified by the computer algorithm, is overlaid with a 3D visualization, there is a strong correlation between the observed injury patterns and the region identified as ablated tissue (e.g., scar tissue) by the algorithm. FIG. 18 shows the overlay for a patient in 3D. An ablated LA tissue identified by the computer algorithm (blue) matches regions of hyperenhancement (white) in the DE-MRI visualization. Similar correlation between MRI visualization and algorithm detection were seen for all patients. This segmentation algorithm, in conjunction with the DE-MRI image data, allowed amounts of unhealthy (e.g., ablated) LA tissue to be quantified as a percentage of the total LA tissue volume.

Quantification of LA Wall Injury and Patient Outcome

Three months after receiving ablative PVAI AF treatment, 35 of 46 patients (76.1%) remained free of AF recurrence. All patients that experienced AF recurrence were placed back on antiarrhythmic drugs. A higher percentage of patients that had a negative outcome for ablative PVAI AF treatment, i.e., experienced AF recurrence, had persistent or permanent AF (8 of 11, 72.7%), as compared to patients that had a positive outcome for ablative PVAI AF treatment (16 of 35, 45.7%, p=0.118).

A substantial difference was observed between the percentage of ablated LA wall tissue resulting from ablative PVAI AF treatment (as determined by DE-MRI and semi-automated quantification) between patients having positive and negative ablative PVAI AF treatment outcome (FIG. 19). In patients having positive outcomes, the average amount of ablated LA tissue resulting from ablative PVAI AF treatment was 19.3+/−6.7%; whereas, in patients having negative outcomes, the average amount of unhealthy LA tissue resulting from ablative PVAI AF treatment was 12.4+/5.7% (p=0.004).

The strong correlation between average amount of ablated LA wall tissue resulting from ablative PVAI AF treatment and treatment outcome persisted when stratifying patients by the first and second quartiles. Using the first quartile (13% ablated LA tissue resulting from ablative PVAI AF treatment), patients with large ablated regions were 18.5× less likely to experience recurrence of AF (odds ratio [OR]:18.5, 95% confidence interval [CI]: 1.27 to 268, p=0.032). After controlling for age, gender, ablation time, and type of AF, relatively large areas of ablated LA tissue strongly predicted the absence of AF recurrence (adjusted OR: 83.7, 95% CI: 2.013 to 3,481.1, p=0.022). Using the second quartile (median) as the cutoff for large ablated areas, the protective association between large ablated areas and recurrences was smaller but still persisted (p equal 0.045).

LA Tissue Ablation Patterns in DE MRI

Visualization of the pulmonary veins and LA tissue using 3D image processing allows for the pattern of ablated LA tissue to be assessed and subsequent isolation procedures to be planned. FIG. 20 shows images of DE-MRI scans of two patients acquired three months after an ablative PVAI AF treatment having a negative outcome. These patients elected to undergo a second ablation procedure, and had a second DE-MRI scan acquired after that procedure. Three-dimensional segmentation of the LA was performed according to methods of the present invention. Incomplete scar formation can be seen near the antrum of the pulmonary veins after the failed ablative PVAI AF treatment. This gap in RF induced ablated areas at the PV antrum (purple) correlated with incomplete electrical isolation of the left superior vein (as determined by electrophysiology study at the time of the second procedure).

After the second ablative PVAI AF treatment, the DE-MRI shows complete scar formation around the ostia of the left superior vein (FIGS. 16, 17, and 20) in both patients. Three months after the second treatment, both patients were free of AF (as determined by 8-day Holter recordings and patient self-report). In such an application, 3D processing provides an advantage over traditional 2D visualization because it provides for the termination of spatial relationships and complex geometry of LA tissues and improved procedure planning and a lower recurrence rate of AF.

LA Wall Injury and MRI Predicted Procedural Outcome

Although all patients in this study had detectable amounts of ablated LA tissues resulting from PVAI AF treatment three months after the treatment, the extent of ablative tissue varied significantly. When we applied our automated algorithm to quantify such ablated LA tissue, the degree of ablated LA tissue resulting from PVAI AF treatment was significantly different between patients having positive and negative outcomes (Table 5). After controlling for patient age, gender, AF phenotype, LA size, and LA volume, patients with ablative tissue ratios>13% are 18.5 times more likely to have a positive outcome (OR: 18.5, 95% CI: 1.27 to 268, p=0.032). These data indicate that degree of the ablated LA tissue predicts ablative PVAI AF treatment success. The overall degree of ablated LA tissue therefore likely has important implications to the lesion type and subsequent interruption of PV to LA electrical conduction. Interruption of PV to LA conduction has been an important component of achieving positive outcome in ablative PVAI AF treatment. Closing conduction gaps in repeat ablative PVAI AF treatments frequently can result in positive treatment outcomes. These data indicate that overall ablation lesion permanence and complete PV isolation amount to important ablative PVAI AF treatment goals.

TABLE 4

Patient Demographics,
Summary by Response to Procedure

|  | Responders (n = 35) | Nonresponders (n = 11) | p Value* |
|---|---|---|---|
| Type of atrial fibrillation |  |  | 0.118 |
| Paroxysmal | 19 (54.3%) | 3 (27.3%) |  |
| Persistent | 16 (45.7%) | 8 (72.7%) |  |
| Gender |  |  |  |
| Female | 12 (34.3%) | 5 (45.5%) | 0.503 |
| Male | 23 (65.7%) | 6 (54.5%) |  |
| Hypertension | 18 (2.9%) | 3 (27.3%) | 0.161 |
| Diabetes | 5 (14.3%) | — | 0.184 |
| Coronary artery disease | 4 (11.4%) | 2 (18.2%) | 0.562 |
| History of smoking | 5 (17.1%) | 4 (36.4%) | 0.107 |
| Valve surgery | 1 (2.8%) | — | 0.571 |
| Myocardial infarction | 2 (5.7%) | 1 (9.1%) | 0.692 |
| Mitral stenosis | 4 (11.4%) | — | 0.241 |
| Age (yrs) | 63.1 ± 11.9 | 71.4 ± 11.4 | 0.048 |
| Left ventricular ejection fraction (%) | 57.1 ± 4.9 | 49.5 ± 9.6 | 0.002 |
| Left atrial area, pre-PVAI (cm$^2$) | 20.1 ± 8.5 | 20.1 ± 8.5 | 0.147 |
| Left atrial volume, pre-PVAI (cm$^3$) | 84.8 ± 24.5 | 84.8 ± 24.5 | <0.001 |
| Antiarrhythmic medications |  |  |  |
| None | 19 (54.3%) | 7 (63.6%) | 0.567 |
| One medication | 12 (34.3%) | 2 (18.2%) |  |
| Multiple medications | 4 (11.4%) | 2 (18.2%) |  |

TABLE 5

Patients at 3-Month Follow-Up

|  | Responders (n = 35) | Nonresponders (n = 11) | p Value* |
|---|---|---|---|
| Percent LA wall injury | 19.3 ± 6.7 | 12.4 ± 5.7 | 0.004 |
| Degree of scar formation |  |  |  |
| Minimal scar formation (>13% of volume enhancement) | 3 (8.6%) | 8 (72.7%) | <0.001 |
| Moderate scar formation (<13% of left atrial volume) | 32 (91.4%) | 3 (27.3%) | <0.001 |
| LA area (cm$^2$), 3-month follow-up | 18.0 ± 5.0 | 24.4 ± 4.6 | <0.001 |
| LA volume (cm$^3$), 3-month follow-up | 74.1 ± 26.4 | 110.3 ± 16.8 | <0.001 |

Stroke Risk Assessment

In an attempt to spare low-risk AF patients from the cost, inconvenience, and risk of warfarin therapy, risk stratification schemes have been developed to tailor anticoagulation therapy. Some risk stratification schemes have been validated and are clinically well established. In patients with AF, some markers for risk, including CHADS$_2$ score, base their higher predictive effect in previous stroke history. The CHADS$_2$ model was developed using stroke risk data from multiple clinical trials. It uses a point system based on individual clinical risk factors including congestive heart failure, hypertension, age, diabetes and prior stroke (CHADS). Although it has been shown to be highly predictive of high-risk patients, this model and other risk stratification schemes fail to adequately predict thromboembolic risk in a substantial portion of the AF population, particularly the moderate-risk subgroup. Identifying novel independent risk factors may aid in the predictive accuracy of such models and help guide clinicians to better allocate anticoagulation therapeutic strategies.

AF may result in structural remodeling of the left atrium, including fibrotic deposition that corresponds with low voltage regions and changes in the electrophsyiological properties of the substrate. However, most AF-thromboembolic risk factors may be based on clinical features and not individual LA pathophysiological properties. This is in part due to the fact that analyzing the LA substrate may be challenging. However, high temporal and spatial resolution magnetic resonance imaging (MRI) may allow for visualization of the thin AF wall. Using the novel MRI sequence of delayed-enhancement, LA structural remodeling may be detected and quantified. According to various embodiments of the subject disclosure, the relationship of the degree of structural remodeling seen in AF patients with stroke and risk stratification schemes may be provided.

In some embodiments, delayed-enhancement MRI (DE-MRI) based LA fibrosis may be independently associated with a previous history of strokes and may increase the predictive performance of a CHADS$_2$ score. In some embodiments, LA fibrosis may represent an early marker for stroke and a therapeutic target in patients with AF.

According to various embodiments of the subject disclosure, LA structural remodeling assessed with DE-MRI can be demonstrated to result in an increased risk of thromboembolism in AF patients. In some embodiments, the quantification of atrial remodeling may improve the predictive performance of the CHADS$_2$ index in stroke risk stratification. In some embodiments, a risk of thromboembolic stroke may be determined. In some embodiments, the risk may be based on at least one of an existence and degree of at least one clinical risk factor for stroke. In some embodiments, determining a risk of stroke, as used herein, does not imply precision. In some embodiments, determining a risk of stork involves estimating a risk of stroke, and this estimate may involve a range of values based on data acquired. For example, this range of values may be from about 5% to 10%, from about 10% to 20%, from about 20% to 40%, from about 40% to 60%, from about 60% to 80%, from about 80% to 90%, from about 90% to 95%, or other suitable ranges.

EXAMPLES

Method
Study Design

A cross-sectional analysis was performed addressing the association between strokes, the risk factors for stroke, and the amount of LA structural remodeling determined by DE-MRI in patients undergoing pulmonary vein isolation for AF.

Study Population

Patients undergoing catheter ablation for AF, who had DE-MRI of the LA prior to the catheter ablation procedure, were evaluated. Their risk factor profiles, including CHADS$_2$, score were catalogued. For example, their clinical, AF, and CHADS$_2$ score characteristics were determined by clinical interrogation and systematic chart review. Patients with cardiac rhythm devices, renal dysfunction, severe claustrophobia or other contraindications for MRI were excluded from the study. Furthermore, patients with an active history of cerebro-vascular disease were excluded from the analysis. 347 patients met these criteria and were included in the final analysis. Their clinical demographics are represented in Table 6. The degree of LA fibrosis was determined as a percent of the LA area. Any history of previous strokes, transient ischemic attacks, Coumadin use, or cerebro-vascular disease was recorded.

TABLE 6

Clinical characteristic according to stroke history

| | Stroke/TIA n = 36 | No Stroke/TIA n = 351 | p |
|---|---|---|---|
| Age (years) | 64 ± 12 | 70 ± 7 | <0.001 |
| AF type | | | |
| Paroxysmal | 15 (31.7%) | 172 (49%) | NS |
| Persistent | 21 (58.3%) | 179 (51%) | NS |
| Coumadin use | 25 (69.4%) | 208 (59%) | NS |
| Female Gender | 23 (63.8%) | 118 (33.6%) | <0.001 |
| Diabetes Mellitus | 3 (8.3%) | 47 (13.4%) | NS |
| Hypertension | 24 (66.7%) | 204 (58%) | NS |
| Congestive Heart Failure | 2 (5.5%) | 36 (10.2%) | NS |
| Age >75 years old | 8 (22.2%) | 65 (18.5%) | NS |
| Risk Score Excluding Strokes | 1.02 ± 0.65 | 1 ± 0.9 | NS |
| $CHADS_2$ Score | 3.02 ± 0.65 | 1 ± 0.9 | <0.001 |
| High Risk (≥2) | 36 (100%) | 90 (25.6%) | NS |
| Moderate Risk (1) | — | 146 (41.6%) | — |
| Low Risk (0) | — | 115 (32.8%) | — |
| LA structural remodeling | | | |
| Fibrosis (%) | 24.4 ± 12.4 | 16.1 ± 9.8 | <0.001 |
| Stage I (<8.5%) [Q1] | 1 (2.8%) | 96 (27.3%) | <0.001 |
| Stage II (8.6%-16%) [Q2] | 9 (25%) | 88 (25.1%) | NS |
| Stage III (16.1%-21%) [Q3] | 7 (19.4%) | 89 (25.3%) | NS |
| Stage IV (>21.1%) [Q4] | 19 (52.8%) | 78 (22.3%) | <0.001 |

AF = Atrial Fibrillation,
TIA = Transient Ischemic Attack,
LA = Left Atria,
Q = Quantile Patients were grouped into either paroxysmal, or persistent AF categories. Paroxysmal AF was defined as any episode that self-terminated within seven days. Persistent AF was defined as an episode of AF lasting longer than about seven days that needed medical or electrical cardioversion to end the AF.

Delayed-Enhancement MRI

A delayed-enhancement MRI was obtained to assess for the extent of LA fibrosis or nonviable tissue using methods previously described. The studies conducted were performed on a 1.5 Tesla Avanto clinical scanner (e.g., from Siemens Medical Solutions, Erlangen, Germany) using a TIM phased-array receiver coil. The scan was acquired about 15 minutes following contrast agent injection (0.1 mmol/kg, Multihance (e.g., from Bracco Diagnostic Inc., Princeton, N.J.)) using a 3D inversion recovery, respiration navigated, ECG-gated, gradient echo pulse sequence.

Acquisition parameters included free-breathing using navigator gating, a transverse imaging volume with voxel size being about 1.25×1.25×2.5 mm (reconstructed to about 0.625×0.625×1.25 mm), TR/TE being about 5.4/2.3 ms, inversion time (TI) being about 270-310 ms, and GRAPPA with R=2 and 46 reference lines. ECG gating was used to acquire a small subset of phase encoding views during the diastolic phase of the LA cardiac cycle. The time interval between the R-peak of the ECG and the start of data acquisition was defined using the cine images of the LA. Fat saturation was used to suppress fat signal. The TE of the scan (about 2.3 ms) was chosen such that fat and water are out of phase and the signal intensity of partial volume fat-tissue voxels was reduced, allowing improved delineation of the LA wall boundary. The TI value for the DE-MRI scan was identified using a scout scan. Scan time for the DE-MRI study was about 5-10 minutes depending on subject respiration and heart rate.

Quantitative Analysis of LA Remodeling

Quantification of LA remodeling was obtained using methods previously described. Following acquisition of the images, the epicardial and endocardial borders were manually contoured using image display and analysis software written in MATLAB (e.g., from The Mathworks Inc. Natick, Mass.). The relative extent of fibrosis was quantified within the LA wall using a threshold-based algorithm based on pixel intensity distribution of healthy myocardium and non-viable myocardium. This method has been shown to have limited inter and intra-observer variability.

Patients were assigned to one of four groups based on the DE-MRI LA structural remodeling distribution quantiles, and expressed as percentage of LA wall enhancement. Patients with Stage I (Q1) remodeling were defined as those with less than about 8.5% enhancement; patients with Stage II (Q2) remodeling were defined as those with about 8.6% to 16% enhancement; Stage III (Q3) remodeling were defined as those with about 16.1% to 21% enhancement; and Stage IV (Q4) remodeling were defined as those with greater than about 21.1%.

Qualitative Analysis of LA Remodeling

Three-dimensional visualization and segmentation of the MRI was performed using OsiriX 2.7.5. The LA and pulmonary tree were segmented manually in all patients and verified visually in the original image stack prior to rendering and visualization. Initial visualization was performed using a Maximum Intensity Projection (MIP) to assess contrast consistency, followed by raycast volume rendering with an opacity-weighted linear table. A Color Look-Up Table (CLUT) mask was applied to the rendered images to optimize differentiation between enhanced and non-enhanced tissue. Healthy tissue was depicted as blue, whereas any tissue with delayed enhancement was depicted as green/yellow.

Statistical Analysis

Normal continuous variables are presented as mean±standard deviations. A one-way analysis of variance (ANOVA) was used to test for statistical significance and was further addressed using the Tukey-Kramer method to correct for multiple comparisons. Categorical variables are presented as number and percentage of total. Pearson's $X^2$ was used to assess for statistical significance. Univariate and multivariate logistic regression analysis were performed to evaluate the association between clinical variables and strokes. Differences were considered significant at a p value of less than 0.05. Statistical analysis was performed using IMP Pro (e.g., from SAS Institute Inc, Car, NC, USA).

Results

A total of 347 patients were included. A history of previous stroke was present in 36 (9.3%) patients. Those patients with previous strokes had significantly higher LA fibrosis (24.4±12.4 vs. 16.2±9.9, p<0.001). A larger amount of LA fibrosis was also seen in those patients with higher $CHADS_2$ scores (≥2:18.7±11.4 vs. <2:14.7±9.2, P<0.01). A logistic regression analysis including all $CHADS_2$ variables except strokes showed that LA fibrosis independently predicted events (p=0.002) and significantly increased the predictive performance of the score (AUC=0.77).

Patient Population

The patients had a mean age of 65±12 years old and 36.8% of the patients were female. Five patients with a known history of stenotic cerebro-vascular disease were excluded from the study. A history of stroke or TIA was documented in 36 (9.3%) of the population. Patients with documented history of stroke were older, and predominantly female (63.8%). There were no significant differences between the two patient groups in regards to type of AF, diabetes, congestive heart failure and hypertension.

LA Structural Remodeling and Stroke

Delayed-enhancement MRI left atrial structural remodeling were shown according to the history of strokes (FIG. 21A) and risk profile (FIG. 21B). Patients who experienced a prior stroke had significantly higher percentage of LA structural remodeling compared to those without history of previous strokes or TIAs (24.4%±12.4 vs. 16.1%±9.8, p=<0.001). This is illustrated, for example, in FIG. 21A. FIGS. 21C, 21D, and 21E show delayed enhancement MRI images representing posteroanterior (PA) views of the left atrium in patients with mild (2.7% shown in FIG. 21C), moderate (17.3% shown in FIG. 21D), and severe (38.4% shown in FIG. 21E) enhancement (green). A Color Look-Up Table (CLUT) mask was applied to the rendered images of FIGS. 21C, 21D, and 21E to differentiate enhanced and non-enhanced tissue.

FIGS. 22A, 22B, and 22C demonstrate the incidence of stroke among the various levels of LA structural remodeling.

FIG. 22A shows a history of stroke according to the different DE-MRI left atrial structural remodeling stages (quantiles). FIG. 22B shows a risk score prevalence for stroke according to the different DE-MRI left atrial structural remodeling stages. As shown in FIG. 22C, the logistic regression odds ratios (OR) for stroke between a clinical (CHAD) and a clinical plus DE-MRI stage IV are compared. Patients with Stage I remodeling experienced very low rates of thromboembolism (2.8%). In comparison, 52.8% of patients with extensive remodeling (Stage IV) had experienced an ischemic event.

LA Structural Remodeling and $CHADS_2$ Index

Those AF patients with higher risk factor profiles for stroke (e.g., $CHADS_2 > 2$) had a significantly larger amount of LA structural remodeling compared to those with a moderate and low risk, for example as shown in Table 7.

TABLE 7

| Characteristics according to stroke risk profile | | | | |
|---|---|---|---|---|
| | Low Risk n = 115 | Moderate Risk n = 146 | High Risk n = 126 | p |
| Age (years) | 59.6 ± 11.3 | 63.7 ± 11.2 | 70.8 ± 11.1 | <0.001 |
| AF type | | | | |
| Paroxysmal | 60 (52.8%) | 77 (52.7%) | 50 (39.7%) | 0.06 |
| Persistent | 55 (47.8%) | 69 (47.3%) | 76 (60.3%) | 0.06 |
| Coumadin use | 57 (49.6%) | 89 (61%) | 87 (69%) | 0.008 |
| Female Gender | 34 (29.6%) | 41 (28.1%) | 66 (52.4%) | 0.04 |
| Diabetes Mellitus | 0 (0%) | 7 (4.8%) | 43 (34%) | <0.001 |
| Hypertension | 0 (0%) | 115 (78.8%) | 113 (89.7%) | <0.001 |
| Congestive Heart Failure | 0 (0%) | 7 (4.8%) | 31 (24.6%) | <0.001 |
| Age >75 years old | 0 (0%) | 17 (11.6%) | 56 (44.4%) | <0.001 |
| Risk Score Excluding Strokes | 0 ± 0 | 1 ± 0 | 1.93 ± 0.80 | <0.001 |
| Stroke/TIA | 0 ± 0 | 0 (0%) | 36 (23.4%) | NS |
| Risk Score Including Strokes | 0 ± 0 | 1 ± 0 | 2.50 ± 0.65 | <0.001 |
| LA structural remodeling | | | | |
| Fibrosis (%) | 13.91 ± 8.77 | 15.99 ± 9.71 | 20.74 ± 11.32 | <0.001 |
| Stage I (<8.5%) [Q1] | 44 (38.3%) | 38 (26%) | 15 (11.9%) | <0.001 |
| Stage II (8.6%-16%) [Q2] | 27 (23.5%) | 38 (26%) | 32 (25.4%) | <0.001 |
| Stage III (16.1%-21%) [Q3] | 25 (21.7%) | 43 (29.5%) | 28 (22.2%) | <0.001 |
| Stage IV (>21.1%) [Q4] | 19 (16.5%) | 27 (18.5%) | 51 (40.5%) | <0.001 |

AF = Atrial Fibrillation,
TIA = Transient Ischemic Attack,
LA = Left Atria,
Q = Quantile When comparing the risk factor profile based on the pre-determined DE-MRI staging system, those with stage IV remodeling had significantly higher $CHADS_2$ scores, for example as shown in Table 8.

TABLE 8

| Characteristics according to DE-MRI LA structural remodeling stage | | | | | |
|---|---|---|---|---|---|
| | Stage I (Q1) [<8.5%] n = 97 | Stage II (Q2) [8.6%-16%] n = 97 | Stage III (Q3) [16.1%-21%] n = 96 | Stage IV (Q4) [>21.1%] n = 96 | p |
| Age (years) | 62.3 ± 12 | 66.2 ± 12 | 64.7 ± 11.2 | 65.9 ± 12.6 | NS |
| AF type | | | | | |
| Paroxysmal | 56 (57.7%) | 52 (53.6%) | 44 (45.8%) | 25 (36.1%) | 0.01 |
| Persistent | 41 (42.3%) | 45 (46.7%) | 52 (54.2%) | 62 (63.9%) | 0.01 |
| Coumadin use | 53 (54.7%) | 62 (63.9%) | 58 (60.4%) | 60 (61.9%) | NS |
| Female Gender | 29 (70.1%) | 34 (35%) | 32 (33.3%) | 46 (47.4%) | NS |
| Diabetes Mellitus | 6 (6.2%) | 11 (11.3%) | 16 (16.7%) | 17 (17.5%) | NS |
| Hypertension | 46 (47.4%) | 59 (60.8%) | 56 (58.3%) | 67 (69.1%) | 0.02 |
| Congestive Heart Failure | 3 (3.1%) | 8 (8.2%) | 9 (9.4%) | 18 (18.6%) | 0.003 |

TABLE 8-continued

Characteristics according to DE-MRI LA structural remodeling stage

|  | Stage I (Q1) [<8.5%] n = 97 | Stage II (Q2) [8.6%-16%] n = 97 | Stage III (Q3) [16.1%-21%] n = 96 | Stage IV (Q4) [>21.1%] n = 96 | p |
|---|---|---|---|---|---|
| Age >75 years old | 13 (13.4%) | 20 (20.6%) | 17 (17.7%) | 23 (23.7%) | NS |
| Strokes/TIA | 1 (1%) | 9 (9.3%) | 7 (7.3%) | 19 (19.6%) | <0.001 |
| Risk Score Excluding Strokes | 0.70 ± 0.73 | 1.01 ± 0.87 | 1.02 ± 0.88 | 1.28 ± 0.95 | <0.001 |
| $CHADS_2$ Score | 0.72 ± 0.77 | 1.19 ± 1.02 | 1.16 ± 1 | 1.68 ± 1.2 | <0.001 |
| High Risk (≥2) | 15 (11.9%) | 32 (25.4%) | 28 (22.2%) | 51 (40.5%) | <0.001 |
| Moderate Risk (1) | 38 (26%) | 38 (26%) | 43 (29.5%) | 27 (18.5%) | <0.001 |
| Low Risk (0) | 44 (38.3%) | 27 (23.5%) | 25 (21.7%) | 19 (16.5%) | <0.001 |
| LA structural remodeling |  |  |  |  |  |
| Fibrosis (%) | 6.1 ± 1.9 | 12.1 ± 2.4 | 18.5 ± 1.5 | 30.9 ± 8.8 | <0.001 |

AF = Atrial Fibrillation,
TIA = Transient Ischemic Attack,
LA = Left Atria,
Q = Quantile LA Structural Remodeling and Clinical Demographics AF patients with more pronounced structural remodeling tended to have more persistent rather than paroxysmal AF. Warfarin use was more frequent in the moderate and high-risk groups but was not associated with a lower prevalence of stroke. A total of 233 patients had documented persistent AF, 143 (71.5%) on warfarin. In the remaining 154 patients with paroxysmal AF, 90 (48.1%) were on warfarin. The large majority of patients who were not on Coumadin had documented use of a daily aspirin.

Age and LA remodeling did not appear to correlate linearly ($R^2$=1.88). However, those older than 75 years of age had significantly higher LA remodeling (19.6%±11.9 vs. 16.3%±9.8, p=0.029) compared to younger AF patients. Further analysis by age groups demonstrated a trend towards larger amounts of structural remodeling (ANOVA, p=0.09).

All patients completed the ablation procedure. Patients were followed up for 446±220 days. Only two strokes were documented prospectively, both of them within 24 hours following the procedure.

Multivariate Analysis

Utilizing univariate and multivariate regression analyses, and controlling for significantly different characteristics and known predictors (e.g., $CHADS_2$ score), excluding stroke, DE-MRI-based left atrial structural remodeling was independently associated with strokes, for example as shown in Table 9). Furthermore, patients with Stage I had a protective odds ratio for strokes and those patients with Stage IV had nearly four times the odds for strokes.

TABLE 9

Univariate and multivariate logistic regression analysis for strokes

| | Univariate | | | Multivariate | | |
|---|---|---|---|---|---|---|
| Variable | OR | p | Variable | OR | p |
| Persistent vs. Paroxysmal AF | 1.34 | 0.4 | Persistent vs. Paroxysmal AF | 1.02 | 0.98 |
| Coumadin Use | 0.64 | 0.22 | Coumadin Use | 0.58 | 0.14 |
| Female vs. Male | 3.49 | <0.001 | Female vs. Male | 3.11 | 0.003 |
| Diabetes Mellitus | 0.58 | 0.38 | Diabetes Mellitus | 0.43 | 0.21 |
| Hypertension | 1.44 | 0.32 | Hypertension | 1.35 | 0.51 |
| Congestive Heart Failure | 0.51 | 0.36 | Congestive Heart Failure | 0.36 | 0.19 |
| Age >75 years old | 1.26 | 0.59 | Age >75 years old | 1.18 | 0.58 |

TABLE 9-continued

Univariate and multivariate logistic regression analysis for strokes

| | Univariate | | | Multivariate | | |
|---|---|---|---|---|---|---|
| Variable | OR | p | Variable | OR | p |
| Left Atrial Remodeling | | | Left Atrial Remodeling | 1.06* | <0.001 |
| Stage I (Q1) | 0.07 | <0.001 | Stage I (Q1) | 0.11 | 0.005 |
| Stage II (Q2) | 0.99 | 0.99 | Stage II (Q2) | 0.90 | 0.81 |
| Stage III (Q3) | 0.71 | 0.42 | Stage III (Q3) | 0.70 | 0.45 |
| Stage IV (Q4) | 3.91 | <0.001 | Stage IV (Q4) | 2.63 | 0.01 |

AF = Atrial Fibrillation,
Q = Quantile,
*OR per unit change

When evaluating a standard clinical predictor of stroke (e.g., $CHADS_2$) along with atrial remodeling as a percentage of the LA, the predictive statistics of the score increased significantly (AUC from 0.58 to 0.72). A clinical prediction score was hypothesized for stroke utilizing numeric allocations for stage IV (+2) of LA structural remodeling, congestive heart failure (+1), hypertension (+1), age >75 (+1), and diabetes (+1). According to certain embodiments, this model's predictive statistics may improve diagnostic performance compared with only clinical variables [Log OR per unit 1.37, p<0.001 vs. 1.03, p=0.87], as shown for example in FIG. 22C.

It was found that AF patients who have suffered ischemic stroke have significantly higher levels of LA fibrosis when evaluated by DE-MRI. In some embodiments, LA structural remodeling, assessed by DE-MRI, may increase the predictive performance of the $CHADS_2$ index for anticoagulation risk stratification. This novel independent risk factor based on LA substrate analysis may improve current risk stratification schemes and increase the understanding of which AF patients are at risk for thromboembolic events.

Although the $CHADS_2$ index may be a validated model, this scheme may be a poor predictor for moderate risk patients, which compose the majority of AF patients. It has been speculated that additional independent risk factors for AF-related thromboembolism may not be included in current risk models. This has led to the evaluation of potential biomarkers as potential risk factors, including inflammatory markers and plasma markers for endothelial dysfunction. However, these additional markers have not been shown to improve the predictive power of common risk schemes.

Some clinical studies demonstrate that prior stroke/transient ischemic attack (TIA), advanced age, hypertension, and diabetes are consistent independent risk factors for stroke in AF patients. Embodiments of the subject disclosure provide direct examination of the LA substrate and individual tissue characteristics in AF patients that are associated with stroke. Structural and functional parameters in AF patients may be based on echocardiographic analysis of left ventricular function and LA size. LA volume index may be a biomarker for stroke. LA volume enlargement was present in most patients (e.g., 75% of patients) with first-ever ischemic strokes. Animal models have shown that an increased atrial size can be associated with a higher degree of interstitial fibrosis and LA enlargement, resulting in increased collagen and glycogen deposition within the LA wall. According to various embodiments, a correlation between LA structural remodeling and ischemic strokes may be demonstrated. LA enhancement using DE-MRI may be more indicative of LA structural remodeling than LA volume and may be a better surrogate marker of remodeling.

Patient age may be a consistent independent risk factor and may be associated with an incremental risk of 1.5% per decade. In some embodiments, risk factors in the elderly may be due in part to LA structural changes that occur over time, especially within the AF population. Advancing age may be independently associated with reduction of left atrial appendage velocities. Myocardial fibrosis may increase with age, and aging may be associated with increased LA enlargement and wall thickness. As shown in the above study, elderly AF patients have increased LA enhancement seen on DE-MRI as compared to younger AF patients, although this relationship may not be linear. In some embodiments, the correlation between high levels of fibrosis and stroke can demonstrate an adverse relationship seen in progressive LA structural remodeling. Therefore, the structural remodeling process accentuated in the elderly may lead to LA substrate and or functional changes resulting in a greater tendency for thromboembolism.

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

There may be many other ways to implement the invention. Various functions and elements described herein may be partitioned differently from those shown without departing from the scope of the invention. Various modifications to these configurations will be readily apparent to those skilled in the art, and generic principles defined herein may be applied to other configurations. Thus, many changes and modifications may be made to the invention, by one having ordinary skill in the art, without departing from the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only and do not limit the invention. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method of administering treatment of atrial fibrillation (AF) to a patient, the method comprising:

capturing MR image data of left atrium tissue of the patient by performing a delayed-enhancement magnetic resonance imaging (DE-MRI) procedure using an MRI system, wherein the MR image data is captured before performing a first ablative treatment procedure;

automatically determining, by an electronic processor, an amount of delayed intravascular contrast enhancement in the MR image data relative to a total LA tissue volume, wherein the amount of delayed intravascular contrast enhancement is positively proportional to an amount of unhealthy tissue in a wall of the left atrium of the patient, the amount being determined with the electronic processor by defining epicardial and endocardial borders of the left atrium in the MR image data to isolate the wall of the left atrium, determining the total tissue volume of the left atrium wall based on the isolated wall of the left atrium in the MR image data, identifying, in the MR image data, a number of voxels within the left atrium wall that exhibit delayed intravascular contrast enhancement indicative of unhealthy tissue based on a pixel intensity histogram, and determining the amount of delayed intravascular contrast enhancement relative to the total tissue volume of the left atrium wall based on the determined number of voxels that exhibit delayed intravascular contrast enhancement indicative of unhealthy tissue and the determined total tissue volume of the left atrium wall;

determining, by the electronic processor, a risk of recurrent atrial fibrillation after the first ablative treatment procedure
  wherein the electronic processor is configured to determine that the risk of recurrent atrial fibrillation after the first ablative treatment procedure is significant in response to a determination by the electronic processor that the amount of delayed intravascular contrast enhancement in the MR image data relative to the total tissue volume of the left atrium wall is greater than a threshold amount, and
  wherein the electronic processor is configured to determine that the risk of recurrent atrial fibrillation after the first ablative treatment procedure is not significant in response to a determination by the electronic processor that the amount of delayed intravascular contrast enhancement in the MR image data relative to the total tissue volume of the left atrium wall is less than the threshold amount;
performing the first ablative treatment procedure in response to a determination by the electronic processor that the risk of recurrent atrial fibrillation after the first ablative treatment procedure is not significant; and
treating the atrial fibrillation with a different treatment modality in response to a determination that the risk of recurrent atrial fibrillation after the first ablative treatment procedure is significant.

2. The method of claim 1, wherein the unhealthy tissue present in the LA wall comprises at least one of a fibrotic tissue, a necrotic tissue, a tissue comprising apoptotic cells, a scar tissue, a tissue having impaired electrical conduction, or an aberrantly electrically remodeled tissue.

3. The method of claim 1, wherein the first ablative treatment procedure comprises at least one of radiofrequency ablation, thermal ablation, laser ablation, surgical ablation, or cryoablation.

4. The method of claim 1, wherein the first ablative treatment procedure comprises pulmonary vein antrum isolation.

5. The method of claim 1, wherein treating the atrial fibrillation with a different treatment modality includes administration of a therapeutic substance.

6. The method of claim 5, wherein the administration of the therapeutic substance includes administration of an antiarrhythmic medication.

7. The method of claim 1, wherein the threshold amount is derived from left atrium tissue data of at least one other patient who experienced recurrent atrial fibrillation after treatment with an ablative treatment procedure.

8. The method of claim 1, further comprising:
capturing post-treatment MR image data of the left atrium of the patient by performing the delayed-enhancement magnetic resonance imaging (DE-MRI) procedure using the MRI system, wherein the post-treatment MR image data is captured after performing the first ablative treatment procedure;
  identifying, by the electronic processor, voxels in the post-treatment MR image data within the left atrium wall that exhibit hyperenhancement of the delayed intravascular contrast enhancement, wherein hyperenhancement is indicative of scarred tissue caused by the first ablative treatment procedure;
  determining, by the electronic processor, a ratio of an amount of voxels exhibiting the hyperenhancement relative to the total tissue volume of the left atrium wall;
  determining, by the electronic processor, a post-treatment risk of atrial fibrillation recurrence for the patient based on a comparison between the determined ratio and a threshold ratio, wherein the electronic processor is configured to determine that the post-treatment risk of atrial fibrillation recurrence is significant when the determined ratio for the patient is less than the threshold ratio; and
performing a second ablative treatment procedure in response to a determination by the electronic processor that the post-treatment risk of atrial fibrillation recurrence is significant.

9. The method of claim 8, further comprising generating, by the electronic processor, a map indicating a degree of electrical isolation of one or more pulmonary veins, wherein the map is generated based on a determined spatial distribution of the delayed intravascular contrast enhancement in the left atrium wall in the post-treatment MR image data,
  wherein performing the second ablative treatment procedure includes using the generated map to target tissue for ablation to close conductive gaps and increase electrical isolation of one or more pulmonary veins.

10. The method of claim 8, further comprising:
identifying, in the post-treatment MR image data, a number of voxels within the left atrium wall that exhibit delayed intravascular contrast enhancement indicative of unhealthy tissue based on a post-treatment pixel intensity histogram;
  determining a post-treatment amount of delayed intravascular contrast enhancement relative to the total tissue volume of the left atrium based on the determined number of voxels that exhibit delayed intravascular contrast enhancement in the post-treatment MR image data; and
  determining, by the electronic processor, a risk of further recurrent atrial fibrillation after the second ablative treatment procedure, wherein the electronic processor is configured to determine that the risk of further recurrent atrial fibrillation after the second ablative treatment procedure is not significant in response to a determination by the electronic processor that the post-treatment amount of delayed intravascular contrast enhancement in the post-treatment MR image data relative to the total tissue volume of the left atrium wall is less than the threshold amount, and
  wherein performing the second ablative treatment procedure includes performing the second ablative treatment procedure in response to the determination by the electronic processor both that the post-treatment risk of atrial fibrillation recurrence is significant and the risk of further recurrent atrial fibrillation after the second ablative treatment procedure is not significant.

11. The method of claim 1, wherein determining the level of risk of thromboembolic stroke in the patient based at least in part on the comparison includes determining that the risk of thromboembolic stroke is significantly increased in response to a determination by the electronic processor that the amount of delayed intravascular contrast enhancement in the MR image data relative to the total left atrium tissue volume in the patient is greater than about 8.5%.

12. A method of administering an ablative atrial fibrillation (AF) treatment modality to a patient, the treatment modality comprising pulmonary vein electrical isolation, the method comprising:

performing a first ablative treatment procedure on the patient;

capturing MR image data of left atrium tissue of the patient after performing the first ablative treatment procedure by performing a delayed-enhancement magnetic resonance imaging (DE-MRI) procedure using an MRI system;

identifying, by an electronic processor, epicardial and endocardial borders of the left atrium in the MR image data;

determining, by the electronic processor, a total LA tissue volume of a left atrium wall based on the identified epicardial and endocardial borders of the left atrium in the MR image data;

identifying, by the electronic processor, voxels in the MR image data within the left atrium wall that exhibit delayed intravascular contrast enhancement, wherein the identified delayed intravascular contrast enhancement is indicative of scarred tissue caused by the first ablative treatment procedure;

determining, by the electronic processor, a ratio of an amount of voxels exhibiting the delayed intravascular contrast enhancement relative to the total tissue volume of the left atrium wall;

generating, by the electronic processor, a map indicating a degree of electrical isolation of one or more pulmonary veins, wherein the map is generated based on a determined spatial distribution of the delayed intravascular contrast enhancement in the left atrium wall;

determining, by the electronic processor a risk of atrial fibrillation recurrence for the patient based on a comparison between (a) the determined ratio of ablated tissue volume to the total LA tissue volume and (b) a threshold ratio derived from LA tissue image data of at least one other patient who did not experience an AF recurrence for a significant period of time after treatment with the AF treatment modality, wherein the risk is determined to be significant when the determined ratio for the patient is less than the threshold ratio, wherein the risk is not determined to be significant when the determined ratio for the patient is greater than the threshold ratio; and performing a second ablative treatment procedure in response to a determination by the electronic processor that the risk of atrial fibrillation recurrence is significant, wherein performing the second ablative treatment procedure includes using the generated map to target tissue for ablation to close conductive gaps and increase electrical isolation of the one or more pulmonary veins.

13. The method of claim 12, wherein the first ablative treatment procedure is performed less than about six months and more than about two days prior to capturing the MR image data.

14. The method of claim 12, wherein the significant period of time comprises at least two months.

15. The method of claim 12, wherein the significant period of time comprises at least three months.

16. The method of claim 12, further comprising determining, by an electronic processor, from tissue image data of the subject patient, an amount of esophageal damage in the subject patient after the first ablative AF treatment.

17. The method of claim 12, wherein the first ablative treatment procedure comprises at least one of radio frequency ablation, thermal ablation, laser ablation, surgical ablation, or cryoablation.

18. The method of claim 12, wherein the first ablative treatment procedure comprises pulmonary vein antrum isolation.

19. The method of claim 12, wherein the risk of AF recurrence is determined, by the electronic processor, to be between about 15% and about 80% risk when the determined ratio for the patient is between about 1% and about 20%.

20. The method of claim 12, wherein the first ablative treatment procedure includes administration of a therapeutic substance.

21. The method of claim 20, wherein the therapeutic substance comprises an antiarrhythmic medication.

22. The method of claim 12, wherein performing the delayed-enhancement magnetic resonance imaging procedure includes providing a contrast agent including gadolinium and capturing the MR image data when a delay period has elapsed after providing the contrasting agent to the patient.

23. The method of claim 12, wherein the risk of atrial fibrillation recurrence is determined, by the electronic processor, to be 18.5 times lower when the determined ratio for the patient is greater than 13% than the risk determined by the electronic processor when the determined ratio is less than 13%.

24. The method of claim 12, wherein identifying, on the MR image, the voxels within the left atrium wall that exhibit the delayed intravascular contrast enhancement includes identifying, on the MR image, voxels that exhibit hyperenhancement.

25. The method of claim 12, further comprising:

receiving, from the MRI system, pre-treatment MR image data of the left atrium tissue of the patient captured before the patient has undergone the first ablative treatment procedure;

defining, on the pre-treatment MR image, epicardial and endocardial borders on the left atrium to isolate the wall of the left atrium;

determining, from the pre-treatment MR image, a total pre-treatment left atrium tissue volume based on the isolated wall of the left atrium;

identifying, on the pre-treatment MR image, voxels within the left atrium wall that exhibit the delayed intravascular contrast enhancement, wherein the delayed intravascular contrast enhancement in the pre-treatment MR image is indicative of unhealthy tissue;

comparing a pre-treatment ratio to a pre-treatment threshold ratio, wherein the pre-treatment ratio being indicative of the identified voxels within the left atrium wall that exhibit the second defined level of delayed intravascular contrast enhancement relative to the total pre-treatment left atrium tissue volume, and wherein the pre-treatment threshold ratio is derived from MR image data of at least one other patient who did not experience an atrial fibrillation recurrence for a significant period of time after treatment with the ablative atrial fibrillation treatment modality;

determining, by the electronic processor, a pre-treatment risk of atrial fibrillation recurrence, wherein the pre-treatment risk is determined, by the electronic processor, to be significant when the pre-treatment ratio for the patient is greater than the pre-treatment threshold ratio, and wherein the pre-treatment risk is determined, by the electronic processor, to not be significant when the pre-treatment ratio for the patient is less than the pre-treatment threshold ratio.

26. A method of providing anticoagulation therapy for a patient with atrial fibrillation (AF), the method comprising:
performing a delayed-enhancement magnetic resonance imaging (DE-MRI) procedure using an MRI system to capture MR image data of left atrium tissue of a patient, wherein performing the DE-MRI procedure includes administering a contrasting agent to the patient causing detectable delayed intravascular contrast enhancement in the captured MR image data;
determining, by an electronic processor, an amount of delayed intravascular contrast enhancement in the MR image data relative to a total left atrium tissue volume by:
defining, on the MR image, epicardial and endocardial borders on the left atrium to isolate the wall of the left atrium,
determining the total left atrium tissue volume based on the isolated wall of the left atrium in the MR image data,
identifying, on the MR image, voxels within the wall of the left atrium that exhibit delayed intravascular contrast enhancement indicative of left atrium fibrosis, and
determining the amount of delayed intravascular contrast enhancement relative to the total left atrium tissue volume based on a quantity of identified voxels that exhibit delayed intravascular contrast enhancement and the determined total left atrium tissue volume;
comparing, by the electronic processor, (i) the determined amount and (ii) a first threshold amount, the first threshold amount derived from left atrium tissue image data of at least one person, other than the patient, who has a history of atrial fibrillation, the first threshold amount statistically controlled for (i) age, (ii) presence of hypertension, and (iii) presence of diabetes;
determining, by the electronic processor, a level of risk of thromboembolic stroke in the patient based at least in part on the comparison,
wherein the electronic processor is configured to indicate a relatively higher level of risk of thromboembolic stroke in response to a determination by the electronic processor that the determined amount of delayed intravascular contrast enhancement relative to the total left atrium tissue volume is greater than the first threshold amount; and
administering an anticoagulation therapy based on the determined level of risk of thromboembolic stroke in the patient.

27. The method of claim 26, wherein determining the amount of delayed intravascular contrast enhancement in the MR image data relative to the total left atrium tissue volume occurs before the patient receives any treatment with an atrial fibrillation treatment modality.

28. The method of claim 26, further comprising:
determining at least one of an existence or a degree of at least one clinical risk factor for stroke for the patient other than the amount of delayed intravascular contrast enhancement by magnetic resonance imaging in the wall of the left atrium,
wherein determining the level of risk of thromboembolic stroke in the patient based at least in part on the comparison further includes estimating the risk of thromboembolic stroke based on the comparison and the at least one of the existence or the degree of the at least one clinical risk factor.

29. The method of claim 28, wherein the at least one clinical risk factor comprises at least one of congestive heart failure, hypertension, age, diabetes, or prior stroke.

30. The method of claim 26, wherein the first threshold amount is further controlled for (iv) warfarin use, (v) gender, (vi) presence of congestive heart failure, and (vii) persistent versus paroxysmal forms of atrial fibrillation.

31. The method of claim 26, wherein administering the anticoagulation therapy based on the determined level of risk of thromboembolic stroke in the patient includes treating the patient with an anticoagulation drug in response to a determination that the determined amount of delayed intravascular contrast enhancement relative to the total left atrium tissue volume is greater than the first threshold amount.

32. The method of claim 31, wherein treating the patient with the anticoagulation drug includes treating the patient with warfarin.

33. The method of claim 31, wherein administering the anticoagulation therapy based on the determined level of risk of thromboembolic stroke in the patient includes not treating the patient with the anticoagulation drug in response to a determination that the determined amount of delayed intravascular contrast enhancement relative to the total left atrium tissue volume is less than the first threshold amount.

34. The method of claim 26, wherein administering the anticoagulation therapy based on the determined level of risk of thromboembolic stroke in the patient includes determining a dosage of an anticoagulation drug for the patient based at least in part on the determined level of risk of thromboembolic stroke in the patient.

\* \* \* \* \*